(12) United States Patent
Cooper et al.

(10) Patent No.: US 8,044,182 B2
(45) Date of Patent: *Oct. 25, 2011

(54) ADIPONECTIN AND USES THEREOF

(75) Inventors: Garth Cooper, Auckland (NZ); Aimin Xu, Hong Kong (KH); Yu Wang, Hong Kong (HK)

(73) Assignee: Philera New Zealand Limited, Auckland (NZ)

( * ) Notice: Subject to any disclaimer, the term of this patent is extended or adjusted under 35 U.S.C. 154(b) by 463 days.

This patent is subject to a terminal disclaimer.

(21) Appl. No.: 12/077,040

(22) Filed: Mar. 14, 2008

(65) Prior Publication Data

US 2010/0016216 A1    Jan. 21, 2010

Related U.S. Application Data

(62) Division of application No. 10/349,326, filed on Jan. 21, 2003, now Pat. No. 7,365,170.

(60) Provisional application No. 60/349,885, filed on Jan. 18, 2002, provisional application No. 60/436,178, filed on Dec. 23, 2002, provisional application No. 60/436,148, filed on Dec. 23, 2002.

(30) Foreign Application Priority Data

| Jan. 18, 2002 | (NZ) | ................................. 516706 |
| Dec. 23, 2002 | (NZ) | ................................. 523410 |
| Dec. 23, 2002 | (NZ) | ................................. 523411 |
| Jan. 17, 2003 | (NZ) | ................. PCT/NZ03/00002 |

(51) Int. Cl.
*A61K 38/18* (2006.01)
*C07K 14/00* (2006.01)
(52) U.S. Cl. .................... 530/399; 424/198.1; 514/2
(58) Field of Classification Search .................... None
See application file for complete search history.

(56) References Cited

U.S. PATENT DOCUMENTS 7,365,170 B2 * 4/2008 Cooper et al. ................ 530/399
* cited by examiner

*Primary Examiner* — Anand Desai
(74) *Attorney, Agent, or Firm* — McDonnell Boehnen Hulbert & Berghoff LLP

(57) ABSTRACT

The invention provides methods and reagents for regulation of metabolic events, such as those mediated by adiponectin and adiponectin agonists. The invention also provides screening assays for identification of biologically active agents, diagnostic and therapeutic agents, and other methods and reagents.

18 Claims, 15 Drawing Sheets

| Peak | Amino acid sequence | Theoretical mass (Da) | Observed mass (Da) | Mass difference (ΔDa) |
|---|---|---|---|---|
| A | KGEPGEAAYVYR (104-115) (SEQ ID NO 8) | 1339.664 | 1679.9462 | 340 |
| B | DGTPGEKGEKGDAG LLGPKGETGDVGMT GAEGPR(62-95) (SEQ ID NO 9) | 3240.544 | 4276.8440 | 1036 |
| C | DGTPGEKGEKGDAG LLGPKGETGDVGMT GAEGPR(62-95) (SEQ ID NO 9) | 3240.544 | 4260.9057 | 1020 |

| | |
|---|---|
| Mouse | MLLLQALLFLLILPSHAEDDVTTTEELapaLVPPPKGTCAGWMAGIPGHPGHNGTPGRDG |
| Human | MLLLGAVLLLLALPGHDQETTTQGPGV---LLPLPKGACTGWMAGIPGHPGHNGVPGRDG |
| Bovine | MLLQGALLLLLALPSHGEDNM-EDP------PLPKGACTGWMAGIPGHPGHNGVPGRDG |
| Monkey | MLL-GAVLLLLALPSHGQDTTTQGPGV---LLPLPKGACTGWMAGIPGHPGHNGVPGRDG |
| Dog | ------------------GPGV---LLPLPKGACPGWMAGIPGHPGHNGTPGRDG |
| | |
| Mouse | RDGTPGEKGEKGDAGLLGPKGETGDVGMTGAEGPRGFPGTPGRKGEPGEAAYVYRSAFSV |
| Human | RDGTPGEKGEKGDPGLIGPKGDIGETGVPGAEGPRGFPGIQGRKGEPGEGAYVYRSAFSV |
| Bovine | RDGTPGEKGEKGDAGLLGPKGETGDVGMTGAEGPRGFPGTPGRKGEPGEAAYVYRSAFSV |
| Monkey | RDGTPGEKGEKGDPGLIGPKGDTGETGVTGAEGPRGFPGIQGRKGEPGEGAYVYRSAFSV |
| Dog | RDGTPGEKGEKGDPGLVGPKGDTGETGVTGVEGPRGFPGTPGRKGEPGESAYVHRSAFSV |
| | |
| Mouse | GLETRVTVPNVPIRFTKIFYNQQNHYDGSTGKFYCNIPGLYYFSYHITVYMKDVKVSLFK |
| Human | GLETYVTIPNMPIRFTKIFYNQQNHYDGSTGKFHCNIPGLYYFAYHITVYMKDVKVSLFK |
| Bovine | GLETRVTVPNVPIRFTKIFYNQQNHYDGSTGKFYCNIPGLYYFSYHITVYMKDVKVSLFK |
| Monkey | GLETYVTVPNMPIRFTKIFYNQQNHYDGSTGKFHCNIPGLYYFAYHITVYMKDVKVSLFK |
| Dog | GLESRVTVPNVPIRFTKIFYNQQNHYDGTTGKFHCNIPGLYYFSYHITVYLKDVKVSLYK |
| | |
| Mouse | KDKAVLFTYDQYQEKNVDQASGSVLLHLEVGDQVWLQVY-GDGDHNGLYADNVNDSTFTG |
| Human | KDKAMLFTYDQYQENNVDQASGSVLLHLEVGDQVWLQVY-GEGERNGLYADNDNDSTFTG |
| Bovine | KDKAVLFTYDQYQEKNVDQASGSVLLHLEVGDQVWLQVYeGE-NHNGVYADNVNDSTFTG |
| Monkey | KDKAMLFTYDQYQENNVDQASGSVLLHLEVGDQVWLQVY-GEGERNGLYADNDNDSTFTG |
| Dog | KDKAMLFTYDQYQEKNVDQASGSVLLHLEVGDQVWLQVY-G--------------- |
| | |
| Mouse | FLLYHD-TN (SEQ ID NO. 13) |
| Human | FLLYHD-TN (SEQ ID NO. 14) |
| Bovine | FLLYHNIVE (SEQ ID NO. 15) |
| SeqName4 | FLLYHD-TN (SEQ ID NO. 16) |
| SeqName5 | -------- (SEQ ID NO. 17) |

Figure 5

LC: liquid control diet; L E: Liquid ethanol diet;
LE+Ad: Liquid ethanol diet + adiponectin treatment LC: liquid control diet; LE: Liquid ethanol diet;
LE+Ad: Liquid ethanol + adiponectin treatment LC: liquid control diet; L E: Liquid ethanol diet;
LE+Ad: Liquid ethanol + adiponectin treatment

ADIPONECTIN AND USES THEREOF

RELATED APPLICATIONS

This application is a divisional application and claims the benefit of U.S. Ser. No. 10/349,326, filed on Jan. 21, 2003, now U.S. Pat. No. 7,365,170 which claims the benefit of U.S. provisional patent application Ser. Nos. 60/349,885 (filed Jan. 18, 2002), 60/436,178 (filed Dec. 23, 2002), and 60/436,148 (filed Dec. 23, 2002). The instant application and the parent application Ser. No. 10/349,326 also claim the benefit of International PCT Application No. PCT/NZ03/00002, filed Jan. 17, 2003, which in turn claims the benefit of New Zealand patent application nos, 516706 (filed Jan. 18, 2002), 523411 (filed Dec. 23, 2002), and 523410 (filed Dec. 23, 2002). Each of the aforementioned applications is incorporated herein by reference for all purposes.

TECHNICAL FIELD

This invention is generally in the field of metabolism and the regulation of various metabolic events by adiponectin and adiponectin agonists, including but not limited to glycoisoforms of adiponectin.

BACKGROUND OF THE INVENTION

Documents referred to by numbering in this specification correspond to the list at the end of the specification. All documents referred to herein are hereby incorporated by reference in their entirety.

Adiponectin (also called ACRP30, adipoQ or GBP28) is a protein secreted from adipocytes. The nucleotide sequence was originally identified by four research groups using different approaches. See, for example, Scherer, P. E., et al., *Journal of Biological Chemistry* 270(45): 26746-26749 (1995); Nakano, Y., et al., *Journal of Biochemistry* 120(4): 803-12 (1996); Hu, E., et al. *Journal of Biological Chemistry* 271(18): 10697-10703 (1996); and Maeda, K., et al., *Biochemical & Biophysical Research Communications*, c221(2): 286-9 (1996). The adiponectin gene is located at chromosome 3q27, a susceptibility locus for type 2 diabetes and other metabolic syndromes [12-14] Several recent studies have been said to support the idea that adiponectin may be a hormone that could link obesity, insulin resistance and type 2 diabetes [9-11].

SUMMARY OF THE INVENTION

In one aspect the present invention is an adiponectin polypeptide wherein the adiponectin polypeptide is glycosylated and wherein it is recombinant, isolated, purified, or synthesised. Preferably but not necessarily the said adiponectin polypeptide is human adiponectin.

Preferably but not necessarily the glycosylated adiponectin polypeptide is at least about 50% pure (more preferably is at least about 80% pure)(still more preferably is at least about 90% pure)(still even more preferably is at least about 95% pure) and (most preferably is at least about 99% pure).

The prolyl residue corresponding to proline residue 91 of human adiponectin is or is not hydroxylated. In one range of embodiments the prolyl residue corresponding to proline residue 91 of human adiponectin is hydroxylated. In another range of embodiments it is not. Other residues may be substituted for hydroxyproline at amino acid position 91 in adiponectin or an adiponectin polypeptide agonist wherein the substitution does not have an undesired effect on the activity of the adiponectin or an adiponectin polypeptide agonist.

Preferably at least one of the lysine residues corresponding to lysine residues 65, 68, 77, and 101 of adiponectin (including but not limited to human adiponectin) or a polypeptide adiponectin agonist is glycosylated.

Preferably but not necessarily the glycosylation of adiponectin or a polypeptide adiponectin agonist at one or more sites of glycosylation within the molecule is with any one or more of a glucosylgalactosyl moiety, a glucosylglucosyl moiety, a galactosylglucosyl moiety, or a galactosylgalactosyl moiety.

In some embodiments two or more of the lysine residues corresponding to lysine residues 65, 68, 77, and 101 or other glycosylation sites of adiponectin (including but not limited to human adiponectin) or a polypeptide adiponectin agonist are glycosylated. In others three or more of the lysine residues corresponding to lysine residues 65, 68, 77, and 101 or other glycosylation sites of adiponectin (including but not limited to human adiponectin) or a polypeptide adiponectin agonist are glycosylated. In still others all four of the lysine residues corresponding to lysine residues 65, 68, 77, and 101 or other glycosylation sites of adiponectin (including but not limited to human adiponectin) or a polypeptide adiponectin agonist are glycosylated.

Irrespective of the lysine or other residues glycosylated preferably but not necessarily the glycosylation is with any one or more of a glucosylgalactosyl moiety, a glucosylglucosyl moiety, a galactosylglucosyl moiety, or a galactosylgalactosyl moiety. Preferably the adiponectin or adiponectin agonist polypeptide is one having one or more of an α-1-2-glucosylgalactosyl-O-hydroxylysine residue at the position corresponding to lysine residue 65 of human adiponectin, an α-1-2-glucosylgalactosyl-O-hydroxylysine residue at the position corresponding to lysine residue 68 of human adiponectin, an α-1-2-glucosylgalactosyl-O-hydroxylysine residue at the position corresponding to lysine residue 77 of human adiponectin, and/or an α-1-2-glucosylgalactosyl-O-hydroxylysine residue at the position corresponding to lysine residue 101 of human adiponectin (ie all fifteen possibilities).

In some forms of the present invention the adiponectin or adiponectin agonist polypeptide has at least one sugar moiety at each of lysine residues 65, 68, 77, and 101.

Preferably the glycosylation is with a single sugar moiety. In other embodiments glycosylation is with multiple sugar moieties.

The present invention also includes an adiponectin or adiponectin agonist polypeptide as aforesaid formulated with one or more of the group consisting of pharmaceutically acceptable excipients, co-actives or diluents so as to be suitable for administration to a mammalian patient.

In still another aspect the present invention is an adiponectin or adiponectin agonist polypeptide having a hydroxyprolyl residue at the position corresponding to proline residue 91 of human adiponectin and wherein it is recombinant, isolated, purified, or synthesized.

In yet another aspect the present invention is, a pharmaceutical composition, an adiponectin or adiponectin agonist polypeptide wherein each of the residues corresponding to lysine residues 65, 68, 77 and 101 of human adiponectin, and/or other natural or synthetic glycosylation sites, is α-1-2-glucosylgalactosyl-O-hydroxylysine and wherein the residue corresponding to proline residue 91 of human adiponectin is hydroxyproline.

In another aspect the invention is, a pharmaceutical dosage unit, an adiponectin or adiponectin agonist polypeptide wherein each of the residues corresponding to lysine residues 65, 68, 77 and 101 of human adiponectin, and/or other natural or synthetic glycosylation sites, is α-1-2-glucosylgalactosyl-O-hydroxylysine and wherein the residue corresponding to proline residue 91 of human adiponectin is not hydroxyproline.

In another aspect the invention is a composition comprising an adiponectin or adiponectin agonist polypeptide wherein the adiponectin or adiponectin agonist polypeptide is glycosylated and wherein the adiponectin polypeptide (preferably human) is recombinant, isolated, purified, or synthesized.

Preferably the composition is formulated with other pharmaceutically acceptable excipients, co-actives, diluents or the like so as to be suitable for administration to mammalian patients.

Preferably the residue of the adiponectin or adiponectin agonist polypeptide corresponding to residue 91 of human adiponectin is hydroxyproline. Preferably at least one of the lysine residues corresponding to lysine residues 65, 68, 77, and 101 of human adiponectin is glycosylated. Preferably the glycosylation is with any one or more of a glucosylgalactosyl moiety, a glucosylglucosyl moiety, a galactosylglucosyl moiety, or a galactosylgalactosyl moiety.

In some forms two or more of the lysine residues corresponding to lysine residues 65, 68, 77, and 101 of human adiponectin are glycosylated, three or more of the lysine residues corresponding to lysine residues 65, 68, 77, and 101 of human adiponectin are glycosylated, or all four of the lysine residues corresponding to lysine residues 65, 68, 77, and 101 of human adiponectin are glycosylated.

Preferably the glycosylation is with any one or more of a glucosylgalactosyl moiety, a glucosylglucosyl moiety, a galactosylglucosyl moiety, or a galactosylgalactosyl moiety.

Preferably each of the residues corresponding to lysine residues 65, 68, 77 and 101 of human adiponectin is α-1-2-glucosylgalactosyl-O-hydroxylysine. The residue of the adiponectin polypeptide corresponding to residue 91 of human adiponectin need not necessarily be hydroxyproline but preferably is hydroxylated.

The glycosylation can be with a single sugar moiety or with multiple sugar moieties.

Preferably the adiponectin polypeptide has at least one glucosylgalactosyl moiety or galactosylglucosyl moiety at each of lysine residues 65, 68, 77, and 101.

The adiponectin polypeptide has the sequence of a naturally occurring mammalian adiponectin polypeptide or has been altered to maintain a desired level of activity as an adiponectin agonist.

Preferably adiponectin or adiponectin agonist polypeptide which is substantially free of at least one non-glycosylated adiponectin or adiponectin agonist polypeptide isoform.

Preferably the composition is substantially free from isoform 1.

Preferably the composition is substantially free from isoform 2.

Preferably the composition is substantially free of any non-glycosylated adiponectin polypeptide isoform.

Preferably the predominant adiponectin or adiponectin agonist polypeptide species is fully glycosylated.

Preferably Lys-65, 68, 77, and 101 are all glycosylated.

The composition may comprise more than one isoform of adiponectin polypeptide.

For example, isoform 3 may be the predominant adiponectin polypeptide in the composition or isoform 4 may be the predominant adiponectin polypeptide in the composition or isoform 5 may be the predominant adiponectin polypeptide in the composition, or isoform 6 may be the predominant adiponectin polypeptide in the composition.

The administration of the composition to a mammal may be used to enhance the effect of insulin. The composition may also be used to allow a subphysiological blood insulin concentration to elicit the biological effect of a normal physiological blood insulin concentration.

In another aspect the invention is a composition additionally including an insulin or insulin analog.

Preferably the insulin or insulin analog is present in an amount or concentration sufficient to elicit a blood insulin or analog concentration of between about 50 pM and about 400 pM.

Preferably the insulin or analog is present in an amount or concentration sufficient to elicit a blood insulin or insulin analog concentration of between about 100 pM and about 300 pM.

Preferably the insulin or insulin analog is present in an amount or concentration sufficient to elicit a blood insulin or analog concentration of about 200 pM.

The composition may be used to inhibit gluconeogenesis when administered to an individual.

The composition may be used, for example, to elicit a plasma adiponectin polypeptide concentration of between about 1 microg/mL and about 20 microg/mL (more preferably, for example, to elicit a plasma adiponectin polypeptide concentration of between about 1.9 microg/mL and about 17 microg/mL).

In another aspect the invention is a method of diagnosing in an individual the presence of, or pre-disposition towards developing, a disease state comprising determining the level of a specific adiponectin polypeptide isoform or expression profile of at least two glycosylated adiponectin polypeptide isoforms in the individual and comparing the expression profile with a expression profile characteristic of an individual who is not suffering from the disease state (or the extent of the disease state), wherein a difference in expression profiles is indicative of the presence of or propensity to develop the disease.

The adiponectin polypeptide isoforms utilized may be, for example, a glycosylated adiponectin polypeptide as previously defined and/or hereinafter defined by reference to the drawings.

Preferably but not necessarily the individual is a human.

The disease state may be, for example, hyperglycemia, insulin resistance, metabolic syndromes associated with insulin resistance, Type 2 diabetes mellitus, or obesity (e.g. including weight gain, reduction or control or weight gain prevention), metabolic syndromes including hypertension, artherosclerosis, coronary heart disease, ischemic heart disease, or polycystic ovary syndrome.

It may also be any of those elsewhere mentioned including those of the liver and TNF-α related.

The adiponectin polypeptide may have been obtained from a biological sample.

The levels or expression patterns may be obtained by quantitatively or qualitatively assessing the expression pattern of glycosylated adiponectin polypeptide isoforms. The assessment method preferably utilises electrophoresis, HLPC, or mass spectrometry. Alternatively or preferably the levels or expression patterns are quantitated or assessed using antibodies specific to glycosylated adiponectin polypeptide isoforms.

In another aspect the invention is a method of diagnosing in an individual the presence of, or pre-disposition towards developing, a disease state comprising determining the level of a specific adiponectin polypeptide isoform or expression profile of at least two glycosylated adiponectin polypeptide isoforms in the individual and comparing the expression profile with a expression profile characteristic of an individual who is suffering from the disease state, wherein a similarity in expression profiles is indicative of the presence of or propensity to develop the disease.

The adiponectin polypeptide isoforms utilized is preferably a glycosylated adiponectin polypeptide isoform as aforesaid.

Preferably any one or more of the adiponectin polypeptide isoforms utilized is a human adiponectin isoform.

Preferably the individual is a human.

The disease state may be, for example, hyperglycemia, insulin resistance, metabolic syndromes associated with insulin resistance, Type 2 diabetes mellitus, or obesity, metabolic syndromes including hypertension, artherosclerosis, coronary heart disease, ischemic heart disease, or polycystic ovary syndrome.

The adiponectin polypeptide can have been obtained from a biological sample.

The levels or expression patterns are preferably obtained by quantitatively or qualitatively assessing the expression pattern of glycosylated adiponectin polypeptide isoforms. The assessment method can utilise electrophoresis, HLPC, or mass spectrometry. The levels or expression patterns can be quantitated or assessed using antibodies specific to glycosylated adiponectin polypeptide isoforms.

In yet another aspect the invention is a method for treating a disease state associated with, for example, adiponectin polypeptide regulation or aberrant insulin sensitivity comprising administering with or without pharmaceutically acceptable excipients, co-actives, diluents or the like an effective amount of a glycosylated adiponectin polypeptide or polypeptide agonist.

The disease state can be, for example, hyperglycemia, insulin resistance, metabolic syndromes associated with insulin resistance, Type 2 diabetes mellitus, or obesity, metabolic syndromes including hypertension, artherosclerosis, coronary heart disease, ischemic heart disease, or polycystic ovary syndrome.

Preferably the glycosylated adiponectin polypeptide is a human adiponectin.

The adiponectin or adiponectin agonist polypeptide may be selected from one or more of the following, for example;

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated, iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated, vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated, viii) an adiponectin or adiponectin agonist polypeptide as defined in vii) wherein the glycosylation is with for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is hydroxyproline, x) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is not hydroxyproline, and xi) a glycosylated adiponectin polypeptide agonist having a desired level of adiponectin activity as compared against a naturally occurring adiponectin.

Preferably, for example, each of the residues of the adiponectin or adiponectin agonist polypeptide corresponding to lysine residues 65, 68, 77 and 101 of human adiponectin is $\alpha$-1-2-glucosylgalactosyl-O-hydroxylysine and the residue corresponding to proline residue 91 of human adiponectin is hydroxyproline.

Alternatively, for example, each of the residues of the adiponectin adiponectin or adiponectin agonist polypeptide corresponding to lysine residues 65, 68, 77 and 101 of human adiponectin is $\alpha$-1-2-glucosylgalactosyl-O-hydroxylysine and wherein the residue corresponding to proline residue 91 of human adiponectin is not hydroxyproline.

In another aspect the invention is a method for treating a disease state associated with adiponectin polypeptide regulation or aberrant insulin sensitivity comprising administering with or without pharmaceutically acceptable excipients, co-actives, diluents or the like an effective amount of one or more compositions of the present invention.

The disease state can be, for example, hyperglycemia, insulin resistance, metabolic syndromes associated with insulin resistance, Type 2 diabetes mellitus, or obesity, metabolic syndromes including hypertension, artherosclerosis, coronary heart disease, ischemic heart disease, or polycystic ovary syndrome.

In another aspect the invention provides a product produced by the process comprising insertion of the polynucleotide sequence encoding an adiponectin or adiponectin agonist polypeptide in a suitable expression vector, introduction of the expression vector incorporating the polynucleotide sequence in an appropriate eukaryotic host cell capable of expressing, and/or processing, and/or glycosylating said adiponectin or adiponectin agonist polypeptide to yield a desired biologically active product.

In one embodiment the polynucleotide sequence encodes a full length adiponectin that is the pro- or prepro- form of an adiponectin or adiponectin agonist or, for example, an adiponectin or adiponectin agonist encoding nucleotide sequence containing a signal or other sequence sufficient to yield a glycosylated molecule.

In another aspect the invention provides a method for reducing weight in a mammalian patient comprising administering with or without pharmaceutically accepted excipients, co-actives, diluents or the like an effective amount of a glycocylated adiponectin or adiponectin agonist polypeptide.

In a further aspect, the invention provides a method for the reduction of weight gain in a mammalian patient comprising administering with or without pharmaceutically accepted excipients, co-actives, diluents or the like an effective amount of a glycocylated adiponectin or adiponectin agonist polypeptide.

In a further aspect, the invention provides a method for the prevention or treatment of obesity in a mammalian patient comprising administering with or without pharmaceutically accepted excipients, co-actives, diluents or the like an effective amount of a glycocylated adiponectin or adiponectin agonist polypeptide.

In a further aspect, the invention provides a method for the prevention of weight gain in a mammalian patient comprising administering with or without pharmaceutically accepted excipients, co-actives, diluents or the like an effective amount of a glycocylated adiponectin or adiponectin agonist polypeptide.

In another aspect, the invention provides a method for treating a mammalian patient deficient in adiponectin or who would otherwise benefit from such treatment comprising administering with or without pharmaceutically accepted excipients, co-actives, diluents or the like an effective amount of glycocylated adiponectin or adiponectin agonist polypeptide.

In another aspect the invention is the use of a glycosylated adiponectin or adiponectin agonist polypeptide (optionally with pharmaceutically acceptable excipients, co-actives, diluents and containment vessels) in the preparation of a pharmaceutical composition or medicament or dosage unit useful in a mammalian patient, for example:

i) in the treatment of a disease state or condition associated with adiponectin polypeptide regulation or in whom administration of a glycosylated adiponectin or adiponectin agonist polypeptide would be desirable; or ii) to enhance the effects of insulin; or iii) inhibit gluconeogenesis.

The use may be with a said pharmaceutical composition or medicament or dosage unit additionally including an insulin or insulin analog. The insulin or analog may be a concentration sufficient to elicit a blood insulin or analog concentration of between about 50 pM and about 400 pM. The insulin or analog may be at a concentration sufficient to elicit a blood insulin or analog concentration of between about 100 pM and about 300 pM. The insulin or analog preferably is at a concentration (i.e. or pressure) sufficient to elicit a blood insulin or analog concentration of 200 pM.

The glycosylated adiponectin adiponectin or adiponectin agonist polypeptide is preferably, for example, a human adiponectin or an agonist thereof.

Preferably the adiponectin or adiponectin agonist polypeptide is selected from one or more of the following;

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated viii) an adiponectin or adiponectin agonist polypeptide as defined in vii) wherein the glycosylation is with, for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is hydroxyproline, x) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is not hydroxyproline, and xi) a glcosylated adiponectin polypeptide agonist having a desired level of adiponectin activity as compared against a naturally occurring adiponectin.

Preferably, for example, each of the residues of the adiponectin or adiponectin agonist polypeptide corresponding to lysine residues 65, 68, 77 and 101 of human adiponectin is $\alpha$-1-2-glucosylgalactosyl-O-hydroxylysine and the residue corresponding to proline residue 91 of human adiponectin is hydroxyproline.

Alternatively each of the residues of the adiponectin polypeptide corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is not hydroxyproline.

In another aspect the invention is an article of manufacture comprising or including a vessel or delivery unit containing at least glycosylated adiponectin or adiponectin agonist polypeptide and instructions for use of the or glycosylated adiponectin adiponectin or adiponectin agonist polypeptide effective for use in a mammalian patient, for example:

i) in the treatment of a disease state associated with adiponectin polypeptide regulation or in whom administration of a glycosylated adiponectin or adiponectin agonist polypeptide would be desirable; or ii) to enhance the effects of insulin; or iii) to inhibit gluconeogenesis.

Preferably the glycosylated adiponectin polypeptide is a human adiponectin or an agonist thereof.

Preferably the adiponectin or adiponectin agonist polypeptide is selected from one or more of the following;

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated, iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated, vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated, viii) an adiponectin or adiponectin agonist polypeptide as defined in vii) wherein the glycosylation is with, for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is hydroxyproline, and x) an adiponectin or adiponectin agonist polypeptide wherein the residues corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is not hydroxyproline, and xi) a glcosylated adiponectin polypeptide agonist having a desired level of adiponectin activity as compared against a naturally occurring adiponectin.

Preferably each of the residues of the adiponectin or adiponectin agonist polypeptide corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is hydroxyproline.

Alternatively each of the residues of the adiponectin or adiponectin agonist polypeptide corresponding to lysine residues 65, 68, 77 and 101 of human adiponectin is, for example, $\alpha$-1-2-glucosylgalactosyl-O-hydroxylysine and wherein the residue corresponding to proline residue 91 of human adiponectin is not hydroxyproline.

In another aspect the invention is a formulation or dosage form capable of delivery of an effective amount of glycosylated adiponectin or adiponectin agonist polypeptide when administered or self administered to a human being or other mammal sufficient to be effective for use in the treatment of a disease state or condition associated with adiponectin polypeptide regulation in a mammalian patient, or in whom administration of an adiponectin or adiponectin polypeptide would be desirable.

Preferably the formulation or dosage form additionally comprises an insulin or an insulin analog. The insulin or insulin analog may be at a concentration sufficient to elicit a blood insulin concentration of between about 50 pM and about 400 pM. The insulin or insulin analog preferably is at a concentration sufficient to elicit a blood insulin or analog concentration of between about 100 pM and about 300 pM.

Most preferably the insulin or insulin analog is at a concentration sufficient to elicit a blood insulin or analog concentration (i.e. presence) of about 200 pM.

Preferably the glycosylated adiponectin polypeptide is a human adiponectin or an agonist thereof.

Preferably the adiponectin or adiponectin agonist polypeptide is selected from one or more of the following;

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated, iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated, vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated, viii) an adiponectin or adiponectin agonist polypeptide as defined in vii) wherein the glycosylation is with, for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, α-1-2-glucosylgalactosyl-O-hydroxylysine and wherein the residue corresponding to proline residue 91 of human adiponectin is hydroxyproline, x) an adiponectin or adiponectin agonist polypeptide wherein the residues corresponding to lysine residues 65, 68, 77 and 101 of human adiponectin is, for example, α-1-2-glucosylgalactosyl-O-hydroxylysine and wherein the residue corresponding to proline residue 91 of human adiponectin is not hydroxyproline, and xi) a glcosylated adiponectin polypeptide agonist having a desired level of adiponectin activity as compared against a naturally occurring adiponectin.

In some forms of the article each of the residues of the adiponectin or adiponectin agonist polypeptide corresponding to lysine residues 65, 68, 77 and 101 of human adiponectin is, for example, α-1-2-glucosylgalactosyl-O-hydroxylysine and wherein the residue corresponding to proline residue 91 of human adiponectin is hydroxyproline.

In other forms of the article each of the residues of the adiponectin or adiponectin agonist polypeptide corresponding to lysine residues 65, 68, 77 and 101 of human adiponectin is, for example, α-1-2-glucosylgalactosyl-O-hydroxylysine and wherein the residue corresponding to proline residue 91 of human adiponectin is not hydroxyproline.

In another aspect of the invention is a formulation or dosage form capable of delivery of an effective amount of glycosylated adiponectin or adiponectin agonist polypeptide when administered or self administered to a human being or other mammal sufficient to enhance the effects of insulin.

Preferably the adiponectin polypeptide is human adiponectin or agonist thereof.

Preferably in the formulation or dosage form the adiponectin or adiponectin agonist polypeptide is selected from one or more of the following;

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated, iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated, vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated, viii) an adiponectin or adiponectin agonist polypeptide as defined in vii) wherein the glycosylation is with, for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, α-1-2-glucosylgalactosyl-O-hydroxylysine and wherein the residue corresponding to proline residue 91 of human adiponectin is hydroxyproline, x) an adiponectin or adiponectin agonist polypeptide wherein the residues corresponding to lysine residues 65, 68, 77 and 101 of human adiponectin is, for example, α-1-2-glucosylgalactosyl-O-hydroxylysine and wherein the residue corresponding to proline residue 91 of human adiponectin is not hydroxyproline, and xi) a glcosylated adiponectin polypeptide agonist having a desired level of adiponectin activity as compared against a naturally occurring adiponectin.

In another aspect the invention is a formulation or dosage form capable of delivery of an effective amount of glycosylated adiponectin or adiponectin agonist polypeptide when administered or self administered to a human being or other mammal sufficient to enhance the effects of insulin, wherein the adiponectin polypeptide or adiponectin agonist preferably as herein defined. Adiponectin agonists include peptide and nonpeptide agonists.

Preferably the formulation or dosage form additionally comprises insulin or an insulin analog (preferably at a presence as previously defined).

In another aspect the present invention is a formulation or dosage form capable of delivery of an effective amount of glycosylated adiponectin or adiponectin agonist polypeptide when administered or self administered to a human being or other mammal sufficient to inhibit gluconeogenesis.

Preferably the adiponectin or adiponectin agonist polypeptide is recombinant, isolated, purified, or synthesised.

Preferably the adiponectin polypeptide is a human adiponectin or agonist thereof.

Preferably at least one of the residues of the adiponectin polypeptide corresponding to lysine residues 65, 68, 77, and 101 of human adiponectin is glycosylated.

In another aspect the invention consists in a formulation or dosage form capable of delivery of an effective amount of glycosylated adiponectin or adiponectin agonist polypeptide when administered or self administered to a human being or other mammal sufficient to enhance the effects of insulin, wherein the adiponectin or adiponectin agonist polypeptide is as herein defined.

Preferably the formulation or dosage form additionally comprises an insulin or an insulin analog (e.g. to levels as previously disclosed).

In still another aspect the invention consists in a method of monitoring the therapy of a mammalian individual predisposed to or suffering from a condition
  a. associated with adiponectin polypeptide regulation or in whom administration of an adiponectin or adiponectin agonist would be desirable;
  b. requiring or benefiting from insulin enhancement, or
  c. requiring or benefiting from gluoneogenesis inhibition, said method comprising or including the step of monitoring the individual for enhancement of the presence of glycosylated adiponectin or adiponectin agonist polypeptide where the glycosylated adiponectin or adiponectin agonist polypeptide has one of the following (A) at least one of the residues of the adiponectin or adiponectin agonist polypeptide corresponding to lysine residues 65, 68, 77 and 101 of human adiponectin glycosylated,
(B) the prolyl residue corresponding to proline residue 91 of human adiponectin is hydroxylated, and
(C) both (A) and (B).

Preferably any adiponectin polypeptide isoforms utilized is a glycosylated adiponectin polypeptide, for example, as disclosed herein.

The condition may be, for example, one or more of hyperglycemia, insulin resistance, metabolic syndromes associated with insulin resistance, Type 2 diabetes mellitus, or obesity, metabolic syndromes including hypertension, artherosclerosis, coronary heart disease, ischemic heart disease, or polycystic ovary syndrome.

In yet another aspect the invention consists in a method of preparing a composition comprising glycosylated adiponectin polypeptide comprising the steps of;
(a) obtaining a first composition comprising at least two forms of an adiponectin or adiponectin agonist polypeptide that differ in their degree or type of glycosylation; and
(b) separating the forms of adiponectin or adiponectin agonist polypeptide at least to some extent such separation being based on the degree or type of glycosylation thereby producing a second composition that differs from the first composition in the adiponectin and/or adiponectin agonist polypeptide profile.

Preferably, for example, the method enriches or at least substantially isolates in the second composition an adiponectin or adiponectin agonist polypeptide of any of the kinds herein described.

Preferably, for example, said adiponectin polypeptide is obtained by the expression of a recombinant polynucleotide encoding an adiponectin or adiponectin agonist polypeptide in mammalian or other cell capable of glycosylating polypeptides.

The recombinant polynucleotide, for example, may encode a polypeptide having the sequence such as that described in FIG. 5 or a biologically active fragment thereof or a variant or a derivative thereof.

Alternatively, for example, the adiponectin polypeptide is purified from an animal tissue, e.g., that of a human, mouse, rat, dog, bovine, or another non-human primate.

Preferably the tissue is serum or adipocytes.

The separation may or may not involve a step of electrophoresis.

The separation may or may not involve a step of chromatography.

Preferably the second composition is a composition or polypeptide of the invention.

In another aspect, the invention provides an antibody specific for a particular glycoisoform of adiponectin.

In an aspect the invention consists in an antibody specific to the glycoisoforms of an adiponectin or adiponectin agonist polypeptide selected from the group consisting of:
(A) an adiponectin or adiponectin agonist in which at least one of the residues of the adiponectin or adiponectin agonist polypeptide corresponding to lysine resides 65, 68, 77 and 101 of human adiponectin is glycosylated,
(B) an adiponectin or adiponectin agonist in which the prolyl residue corresponding to proline residue 91 of human adiponectin is hydroxylated, and,
(C) both (A) and (B).

Preferably the antibody is a monoclonal antibody.
The antibody may be capable of two site capture.

In another aspect the invention consists in a composition of any such antibody.

In another aspect the invention consists in a hyridoma specific to the production of antibodies specific to the glycoisoforms of an adiponectin or adiponectin agonist, e.g., a polypeptide selected from the group consisting of
(A) an adiponectin or adiponectin agonist in which at least one of the residues of the adiponectin or adiponectin agonist polypeptide corresponding to lysine resides 65, 68, 77 and 101 of human adiponectin glycosylated,
(B) an adiponectin or adiponectin agonist in which the prolyl residue corresponding to proline residue 91 of human adiponectin is hydroxylated, and,
(C) both (A) and (B).

In another aspect the invention consists in a method of screening an agent or for an agent useful in a mammal for enhancing the level of glycosylated adiponectin polypeptide activity that has one of the following:
(A) an adiponectin or adiponectin agonist in which at least one of the residues of the adiponectin or adiponectin agonist polypeptide corresponding to lysine resides 65, 68, 77 and 101 of human adiponectin glycosylated,
(B) an adiponectin or adiponectin agonist in which the prolyl residue corresponding to proline residue 91 of human adiponectin is hydroxylated, and,
(C) both (A) and (B),
which method comprises administering to the mammal or tissue thereof or to a mammal any enhancement of such glycosylated adiponectin or adiponectin agonist polypeptide production by such mammal or mammalian tissue.

In another aspect the invention consists in an agent useful for enhancing the level of glycosylated adiponectin polypeptide activity in a subject by use of an agent that has one of the following
(A) an adiponectin or adiponectin agonist in which at least one of the residues of the adiponectin polypeptide corresponding to lysine resides 65, 68, 77 and 101 of human adiponectin glycosylated,
(B) an adiponectin or adiponectin agonist in which the prolyl residue corresponding to proline residue 91 of human adiponectin is hydroxylated, and,
(C) both (A) and (B),
identified by a method of screening which comprises administering to the mammal or tissue thereof or to a mammal any such molecule and identifying glycosylated adiponectin polypeptide activity or production by such mammal or mammalian tissue.

In another aspect the invention includes a mixture of isoforms of an adiponectin or adiponectin agonist polypeptide(s) by virtue of enrichment or removal, conversion or synthesis of isoforms in which at least one or more of the residues corresponding to lysine residues 65, 68, 77, and 101 of human adiponectin is glyscosylated and wherein the prolyl residue corresponding to proline residue 91 of human adiponectin is hydroxylated.

In another aspect the invention includes a mixture of isoforms of an adiponectin or adiponectin agonist polypeptide(s) by virtue of enrichment or removal, conversion or synthesis of isoforms in which at least one or more of the residues corresponding to lysine residues 65, 68, 77, and 101 of human adiponectin is glyscosylated and wherein the prolyl residue corresponding to proline residue 91 of human adiponectin is not hydroxylated.

In another aspect the invention includes an isoform of adiponectin or adiponectin agonist polypeptide(s) in which at least one or more of the residues corresponding to lysine residues 65, 68, 77, and 101 of human adiponectin is glyscosylated.

The invention also includes an isoform of adiponectin or adiponectin agonist polypeptide(s) in which at least one or more of the residues corresponding to lysine residues 65, 68, 77, and 101 of human adiponectin is glyscosylated and having a hydroxyprolyl residue at the position corresponding to proline residue 91 of human adiponectin, or an isoform of adiponectin or adiponectin agonist polypeptide(s) in which at least one or more of the residues corresponding to lysine residues 65, 68, 77, and 101 of human adiponectin is glyscosylated and not having a hydroxyprolyl residue at the position corresponding to proline residue 91 of human adiponectin.

In another aspect the invention is a method of screening for one or more cells capable of expressing a glycosylated adiponectin or adiponectin agonist polypeptide comprising identifying and/or determining the level of a specific adiponectin polypeptide isoform or expression profile of at least two glycosylated adiponectin or adiponectin agonist polypeptide isoforms expressed by said cell or cells and identifying and/or purifying and/or isolating said cell or cells.

Preferably, for example, the glycosylated adiponectin polypeptide is human adiponectin or agonist thereof.

Preferably the adiponectin polypeptide is selected from one or more of the following:

i) an adiponectin or adiponectin agonist polypeptide wherein at least one of the residues corresponding to lysine residues 65, 68, 77, and 101 of human adiponectin is glycosylated, ii) an adiponectin or adiponectin agonist polypeptide as defined in i) wherein glycosylation is with, for example, any one or more of a glucosylgalactosyl moiety, a glucosylglucosyl moiety, a galactosylglucosyl moiety, or a galactosylgalactosyl moiety, iii) an adiponectin or adiponectin agonist polypeptide wherein two or more of the residues corresponding to lysine residues 65, 68, 77, and 101 of human adiponectin is glycosylated, iv) an adiponectin or adiponectin agonist polypeptide as defined in iii) wherein the glycosylation is with, for example, any one or more of a glucosylgalactosyl moiety, a glucosylglucosyl moiety, a galactosylglucosyl moiety, or a galactosylgalactosyl moiety, v) an adiponectin or adiponectin agonist polypeptide wherein three or more of the residues corresponding to lysine residues 65, 68, 77, and 101 of human adiponectin are glycosylated, vi) an adiponectin or adiponectin agonist polypeptide as defined in v) wherein the glycosylation is with, for example, any one or more of a glucosylgalactosyl moiety, a glucosylglucosyl moiety, a galactosylglucosyl moiety, or a galactosylgalactosyl moiety, vii) an adiponectin or adiponectin agonist polypeptide wherein all four of the residues corresponding to lysine residues 65, 68, 77, and 101 of human adiponectin are glycosylated, viii) an adiponectin or adiponectin agonist polypeptide as defined in vii) wherein the glycosylation is with, for example, any one or more of a glucosylgalactosyl moiety, a glucosylglucosyl moiety, a galactosylglucosyl moiety, or a galactosylgalactosyl moiety, ix) an adiponectin or adiponectin agonist polypeptide wherein the residues corresponding to lysine residues 65, 68, 77 and 101 of human adiponectin is, for example, α-1-2-glucosylgalactosyl-O-hydroxylysine and wherein the residue corresponding to proline residue 91 of human adiponectin is hydroxyproline, x) an adiponectin or adiponectin agonist polypeptide wherein the residues corresponding to lysine residues 65, 68, 77 and 101 of human adiponectin is α-1-2-glucosylgalactosyl-O-hydroxylysine and wherein the residue corresponding to proline residue 91 of human adiponectin is not hydroxyproline, and xi) a glcosylated adiponectin polypeptide agonist having a desired level of adiponectin activity as compared against a naturally occurring adiponectin.

Preferably, for example, each of the residues of the adiponectin or adiponectin agonist polypeptide corresponding to lysine residues 65, 68, 77 and 101 of human adiponectin is α-1-2-glucosylgalactosyl-O-hydroxylysine and the residue corresponding to proline residue 91 of human adiponectin is hydroxyproline.

Additionally, for example, each of the residues of the adiponectin or adiponectin agonist polypeptide corresponding to lysine residues 65, 68, 77 and 101 of human adiponectin may be α-1-2-glucosylgalactosyl-O-hydroxylysine and the residue corresponding to proline residue 91 of human adiponectin is not hydroxyproline.

Preferably the identification and/or determination of any one or adiponectin or adiponectin agonist polypeptides utilises an antibody having desirable binding characteristics with regard to one or more glycoisoforms of the adiponectin or adiponectin agonist polypeptide selected from the group consisting of:

(A) an adiponectin or adiponectin agonist in which at least one of the residues of the adiponectin polypeptide corresponding to lysine resides 65, 68, 77 and 101 of human adiponectin is glycosylated, (B) an adiponectin or adiponectin agonist in which the prolyl residue corresponding to proline residue 91 of human adiponectin is hydroxylated, and, (C) both (A) and (B).

Preferably the antibody is a monoclonal antibody.

The antibody may be specific to or have desirable binding characteristics with regard to an adiponectin or adiponectin agonist polypeptide wherein each of the residues of the adiponectin or adiponectin agonist polypeptide corresponding to lysine residues 65, 68, 77 and 101 of human adiponectin is, for example, α-1-2-glucosylgalactosyl-O-hydroxylysine and the residue corresponding to proline residue 91 of human adiponectin is hydroxyproline.

The antibody may be specific to to or have desirable binding characteristics with regard to an adiponectin or adiponectin agonist polypeptide wherein each of the residues of the adiponectin or adiponectin agonist polypeptide corresponding to lysine residues 65, 68, 77 and 101 of human adiponectin is, for example, α-1-2-glucosylgalactosyl-O-hydroxylysine and the residue corresponding to proline residue 91 of human adiponectin is not hydroxyproline.

The invention also includes all of the subject matter of the claims hereto, including any one or more cells identified and/or isolated and/or purified by a method of screening for one or more cells capable of expressing a glycosylated adiponectin polypeptide comprising identifying and/or determining the level of a specific adiponectin polypeptide isoform or expression profile of at least two glycosylated adiponectin polypeptide isoforms expressed by said cell or cells and identifying and/or purifying and/or isolating said cell or cells.

Accordingly to another aspect the present invention includes a method of treating a mammalian patient subject to or for, for example, liver disease and/or having any of the characteristics of liver disease which comprises or includes administering to that patient an effective amount of an adiponectin and/or an agonist thereof.

The liver disease may be, for example, any one or more of acute liver disease, chronic liver disease, inflammation of the liver, dysfunction of the liver, fatty liver (hepatic steatosis), fibrosis of the liver, cirrhosis of the liver, necrosis of the liver, hepatocellular necrosis, alcoholic liver disease, alcoholic hepatic steatosis, alcoholic hepatitis, alcoholic hepatic necrosis, alcoholic hepatic cirrhosis, hepatic necrosis, hepatic steatosis, hepatic steatosis associated with diabetes, hepatic steatosis associated with a diet rich in lipids, hepatic steatosis associated with abnormalities of lipid metabolism, hepatitis caused by any condition, hepatic necrosis caused by any condition, acute hepatitis, chronic hepatitis, chronic active hepatitis, hepatitis secondary to viral infection or inflammation of the liver, hepatitis A, hepatitis B, hepatitis C, hepatitis D, hepatitis E, hepatitis G, hepatitis secondary to the action of any drug or toxin, hepatitis or hepatic dysfunction consequent upon cholestasis, primary biliary cirrhosis, hepatic granulomatosis, and/or conditions in which elevated tissue or blood concentrations of tumour necrosis factor a play a pathogenic role.

Preferably, for example, the mammal is human and the adiponectin is a human adiponectin or agonist thereof.

Preferably, for example, the adiponectin is full length.

Preferably, for example, the adiponectin is glycosylated at one or more sites.

More preferably, the adiponectin is a human adiponectin glycosylated at one or more of the residues corresponding to lysine residues 65, 68, 77, and 101. It will be appreciated when referring to adiponectin of non-human species, an adiponectin variant, an adiponectin agonist polypeptide, or a truncated adiponectin different from human adiponectin, the residues of the adiponectin can be referred to using the numbering of the corresponding human sequence residue, as determined by optimally aligning the two sequences.

The adiponectin or adiponectin agonist preparation may be formulated in a manner suitable for administration to a human, preferably, for example, in a form for parenteral administration via routes such as subcutaneous (s.c.), intradermal (i.d.), intravenous (i.v.), intraperitoneal (i.p.) or transdermal. Other preparations are also envisaged in which said adiponectin is administered via the oral, buccal, rectal, vaginal, intravesical, intrathecal, intraventricular, intracerebral or other routes known or desired to those skilled in the art.

The preferred routes of administration are parenteral. An adiponectin or adiponectin agonist suitable for parenteral administration is formulated, for example, in aqueous solution containing buffers for stabilization, is preferably at or near isotonic strength, and with suitable antiseptic, antifoaming, anti-precipitation and other stabilizing agents known to those skilled in the art to be suitable for pharmaceutical formulation of proteins suitable for administration to mammals, particularly humans for example, and particularly those suitable for stabilization in solution of therapeutic proteins for administration to mammals including humans.

In a further aspect the present invention consists in a method of treating a mammalian patient subject to or for alcoholic liver disease and/or having any of the characteristics of alcoholic liver disease which comprises or includes administering to that patient an adiponectin and/or an agonist thereof.

In a further aspect the present invention consists in a method of treating a mammalian patient to prevent and/or reverse liver disease and/or any of the characteristics of liver disease which comprises or includes administering to that patient an adiponectin and/or an agonist thereof.

In still a further aspect the present invention consists in a method of treating a human being subject to liver disease and/or having any of the characteristics of liver disease which comprises administering to that patient an effective amount of an adiponectin and/or an agonist thereof.

In a further aspect the present invention consists in a method of treating a mammalian patient to prevent and/or reverse alcoholic liver disease and/or any of the characteristics of alcoholic liver disease which comprises or includes administering to that patient an adiponectin and/or an agonist thereof.

In still a further aspect the present invention consists in a method of treating a human being subject to alcoholic liver disease and/or having any of the characteristics of alcoholic liver disease which comprises administering to that patient an effective amount of an adiponectin and/or an agonist thereof.

In a yet further aspect the present invention consists in a method of treating a mammalian patient subject to any one or more of hepatic steatosis (fatty infiltration), hepatic inflammation, hepatic necrosis, hepatic fibrosis, hepatic cirrhosis, and/or hepatic dysfunction which comprises or includes administering to that patient an adiponectin and/or an agonist thereof.

In still a further aspect the present invention consists in an article of manufacture comprising or including
a vessel containing an adiponectin, and/or an adiponectin agonist(s);
instructions for use of an adiponectin or an adiponectin agonist (for example, as contained within the vessel) for treating, preventing or reversing liver disease and/or any characteristic of liver disease.

In still a further aspect the present invention consists in an article of manufacture comprising or including
a vessel containing an adiponectin and/or an adiponectin agonist(s);
instructions for use of adiponectin, or an adiponectin agonist (for example, as contained within the vessel) for treating, preventing or reversing alcoholic liver disease and/or any characteristic of alcoholic liver disease.

In still a further aspect the present invention consists in an article of manufacture comprising or including
a packaging material containing an adiponectin and/or an adiponectin agonist;
instructions for use of an adiponectin and/or an adiponectin agonist (for example, as contained within the packaging material) for treating, preventing or reversing liver disease and/or any characteristic of liver disease.

In still a further aspect the present invention consists in an article of manufacture comprising or including
a packaging material containing an adiponectin and/or an adiponectin agonist;
instructions for use of an adiponectin and/or an adiponectin agonist (for example, as contained within the packaging material) for treating, preventing or reversing alcoholic liver disease and/or any characteristic of alcoholic liver disease.

In still a further aspect the present invention consists in the use of (preferably an effective amount of) an adiponectin and/or an adiponectin agonist in the manufacture with other material or materials (whether recipients, co-actives, diluents or the like and/or whether a dosage unit defining vessel) of a dosage unit or pharmaceutical composition effective for use in the treatment, prevention and/or reversal of disease and/or any characteristic of liver disease in a mammalian patient (whether human or otherwise).

In still a further aspect the present invention consists in the use of (preferably an effective amount of) an adiponectin and/or an adiponectin agonist in the manufacture with other material or materials (whether recipients, co-actives, diluents or the like and/or whether a dosage unit defining vessel) of a dosage unit or pharmaceutical composition effective for use in the treatment, prevention and/or reversal of alcoholic liver disease and/or any characteristic of alcoholic liver disease in a mammalian patient (whether human or otherwise).

In another aspect the present invention consists in a method of treatment of mammalian patient which includes or comprises, in any sequence, the monitoring of the adiponectin or agonist thereof in the mammalian patient and or the administration to the mammalian of adiponectin and or an agonist thereof, such treatment being for the purpose of treating, reversing, or preventing liver disease and or any characteristic of liver disease (and may include alcoholic liver disease). Preferably the mammalian patient is a human.

In another aspect the present invention consists in a method of treatment of mammalian patient which includes or comprises, in any sequence, the monitoring of the adiponectin mRNA in the mammalian patient and or the administration to the mammalian of an adiponectin and/or an agonist thereof for treating, reversing, or preventing liver disease and or any characteristic of liver disease (including alcoholic liver disease). Preferably the mammalian patient is a human.

In a further aspect the present invention consists in a method of measuring active adiponectin in a mammalian patient which comprises or includes, for example, assaying or assessing the concentration or amount of an active form or forms of adiponectin in blood or tissue(s).

The concentration of adiponectin may be determined by any method well known to those skilled in the art, including but not limited to immunological methods such as radioimmunoassay (RIA), ELISA, etc., as described in U.S. application 60/349,885, in which is described an active form of adiponectin and its composition of matter.

Preferably, for example, the tissue is adipose tissue.

In a further aspect the present invention includes a method of measuring adiponectin in a mammalian patient which comprises or includes, for example, assaying or assessing the concentration or amount of an adiponectin mRNA in blood or tissue(s).

The concentration of adiponectin mRNA may be determined by any method well known to those skilled in the art, including but not limited to RT-PCR, Northern analysis, in situ hybridisation, and radioimmunoassay (RIA).

Preferably, the tissue is adipose tissue.

In a further aspect the present invention includes an assay capable of measuring an adiponectin in a mammalian patient which comprises or includes isolating from the mammalian patient a blood or tissue(s) sample, preparing the sample, assaying the concentration of an adiponectin in blood or tissue(s) by any method known to those skilled in the art, including but not limited to immunological methods such as as radioimmunoassay (RIA), ELISA, etc. Methods for measurement of adiponectin are described in U.S. patent application No. 60/349,885, which describes an active form of adiponectin and its composition of matter.

In a yet further aspect the present invention includes a method of treating a mammalian patient subject to or for any of the conditions selected from, for example, acute liver disease, chronic liver disease, inflammation of the liver, dysfunction of the liver, fatty liver (hepatic steatosis), fibrosis of the liver, cirrhosis of the liver, necrosis of the liver, hepatocellular necrosis, alcoholic liver disease, alcoholic hepatic steatosis, alcoholic hepatitis, alcoholic hepatic necrosis, alcoholic hepatic cirrhosis, hepatic necrosis, hepatic steatosis, hepatic steatosis associated with diabetes, hepatic steatosis associated with a diet rich in lipids, hepatic steatosis associated with abnormalities of lipid metabolism, hepatitis caused by any condition, hepatic necrosis caused by any condition, acute hepatitis, chronic hepatitis, chronic active hepatitis, hepatitis secondary to viral infection or inflammation of the liver, hepatitis A, hepatitis B, hepatitis C, hepatitis D, hepatitis E, hepatitis G, hepatitis secondary to the action of any drug or toxin, hepatitis or hepatic dysfunction consequent upon cholestasis, primary biliary cirrhosis, hepatic granulomatosis, and/or conditions in which elevated tissue or blood concentrations of tumour necrosis factor a play a pathogenic role, which comprises or includes administering to that patient an adiponectin and/or an agonist thereof.

Preferably, the patient is a human and the adiponectin is a human adiponectin or agonist thereof.

Preferably the adiponectin or agonist thereof is full length.

Preferably the adiponectin or agonist thereof is glycosylated at one or more sites.

Adiponectin in respect of the treatment of human beings preferably includes an adiponectin, and/or an agonist(s) thereof that are related to human adiponectin such as may be derived by various molecular biology techniques (including recombinant techniques), as well as microbiology, cell biology, biochemistry, nucleic acid chemistry, and immunology techniques, which are within the skill of the art. Adiponectins and adiponectin agonist polypeptides may be produced recombinantly by inserting a polynucleotide (usually DNA) sequence that encodes the protein into an expression vector and expressing the peptide in an appropriate host. A polynucleotide encoding the desired polypeptide, whether in fused or mature form, and whether or not containing a signal sequence to permit secretion, may be ligated into expression vectors suitable for any convenient host. Any of a variety of expression vectors known to those of ordinary skill in the art may be employed, although eukaryotic expression systems are recommended because of the ability of eukaryotic cells to perform post-translational modifications, such as glycosylation. Expression may be achieved in any appropriate host cell that has been transformed or transfected with an expression vector containing a DNA molecule which encodes the recombinant peptides. Examples of eukaryotic host cells are known in the art and include yeast, avian, insect, plant, and animal cells such as COS7, HeLa, CHO and other mammalian cells. Cells derived from adipocytes may be particularly suitable for expression of the adiponectin polypeptides defined herein. It will be appreciated that eukaryotic host cells may differentially glycosolate expressed proteins, such that appropriate host cells may be identified by determing the manner in which the expressed protein is glycosolated. Host cells may thereby be selected that express the desired glycoisoforms of the adiponectin polypeptide. Standard techniques for recombinant production are described for example, in Sambrook, supra. The adiponectin or adiponectin agonist polypeptide can be obtained by expression of a recombinant polynucleotide encoding adiponectin or a biologically active fragment thereof or a variant or derivative thereof or isoform or a polypeptide agonist thereof in mammalian cells.

In another embodiment, adiponectins (including mixtures of isoforms and glycoisoforms) can also be purified from an animal tissue or other source such as, but not limited to, serum or adipocytes. Methods for purifying adiponectins from adipocytes are further described in U.S. patent application No. 60/349,885. The animals from which glycosylated adiponectins can be obtained include but are not limited to humans, mice, rats, dogs, bovines, and other non-human primates.

In accordance with the present invention reference to an "effective amount" is to any amount sufficient to effect beneficial or desired results including beneficial or desired clinical result.

We have demonstrated that a number of liver conditions, such as alcoholic liver disease, alcoholic hepatic steatosis, alcoholic hepatitis and alcoholic hepatic necrosis, diabetic steatosis and diabetes mellitus, insulin resistance secondary to a high fat diet±hepatic steatosis, are accompanied by lowered blood and adipose concentrations of adiponectin protein and adiponectin mRNA.

When adiponectin deficiency is present, ideally a sufficient amount of the active form of an adiponectin or adiponectin agonist is preferably administered to the human or other mammal under treatment to restore the circulating, blood or tissue levels of adiponectin activity to normal, or within ±5% of normal, or within ±10% of normal, or within ±25% of normal, or within ±50% of normal. Adiponectin therapy can also be effective when apparently normal circulating concentrations of adiponectin are present, however, and the presence of normal adiponectin levels is thus not necessarily a contraindication to adiponectin or adiponectin agonist therapy.

Such an effective amount can be administered in one or more administrations by various routes of administration.

Reference herein to "mammals" include, in addition to man and mice, any appropriate mammal but is not limited to farm animals, sport animals, pets, and primates.

Circumstances and characteristics of alcoholic liver disease may be predicated by, for example, any one or more of steatosis (fatty infiltration), inflammation, necrosis, fibrosis, cirrhosis, and/or dysfunction.

A preferred dosage unit suitable for use with man in accordance with the present invention is any form capable of providing desired adiponectin activity within a human and which does not lead to lack of stability thereof on storage nor unnecessary or undesired inactivation within the body prior to eliciting a beneficial effect.

As will be described hereinafter in its most simplistic forms and not dependant upon any vessel (whether a capsule or otherwise) the adiponectin and/or adiponectin agonist can also be administered by means of a surgically implanted delivery device such as an osmotic pump, as is well know in the are alternative dosage forms suitable for administration of therapeutic protein may also be used.

Accordingly, in another aspect of the invention there is provided a method of treating a mammalian patient itself still able to encode for adiponectin comprising administering to the patient an adiponectin and/or an agonist of the site of action of adiponectin in a sufficient amount(s) to suppress TNF-α levels below those that would have been or likely would have been present without such administration.

For example, such administration may be to treat, ameliorate, prevent and/or reverse a TNF-α disease or disorder and/or any of the characteristics of a TNF-α disease or disorder.

Preferably, the mammal is a human and the adiponectin is a human adiponectin or an agonist thereof.

Preferably, the adiponectin or adiponectin agonist is full length.

Preferably the adipoection or adiponectin agonist is glycosylated.

More preferably, the adiponectin is human adiponectin or adiponectin agonist glycosylated at one or more of the residues corresponding to lysine residues 65, 68, 77, and 101.

Preferably said TNF-αdisease or disorder is, for example, any one or more of the following:- inflammatory disease, circulatory disease, portal hypertension, pulmonary hypertension, allegic diseases, Crohn's disease, autoimmune haemolytic anemia, psoriasis, hepatic disease, pancreatic disease, neurodegenerative disease, central nerve failure, toxaemia, climacteric failure, gestosis, adiposis, hyperlipidemia, hypercholesteremia, abnormal glucose tolerance, solid tumor, tumor cancer and accompanying cachexia, endocrine disease, Creutzfeldt-Jakob disease, viral infection, post-percutaneous coronary arterioplasty, vascular hypertrophy or occlusion, post-PTCA/stenting/bypass surgery vascular reocclusion/restenosis, post-intervention vascular hypertrophy or occlusion, suppression of implantation-induced vascular failure and rejection, rejection episodes following organ or tissue transplant and automimmune disease, side effects associated with TNF generation during neoplastic therapy and also to eliminate or ameliorate shock related symptoms associated with the treatment or prevention of graft rejection, dialytic hypotension, glaucoma, high ocular tension, myasthenia gravis, chronic defatigation, bone disease, neurological disorders, TNF-☐ induced insulin resistance, aberrant apoptosis, complications of diabetes mellitus or stress hyperglycemia, chronic obstructive pulmonary disease, chronic bronchitis and emphysema.

Preferably said inflammatory response is, for example, any one of the following: diabetic complications such as retinopathy, nephropathy, neuropathy, major vascular and microvascular disorders; arthritis such as chronic rheumatoid arthritis, osteoarthritis, rheumatoid myelitis and periosteosis; postooperative/posttraumatic inflammation; remedy of swelling; pharyngitis; cystitis; pneumonia; myocarditis; cardiomyopathy; atopic dermatitis; inflammatory intestinal disease such as Crohn's disease and ulcerative colitis; meningitis; inflammatory ophthalmic disease; inflammatory pulmonary disease such as pneumonia, silicotuberculosis, pulmonary sarcoidosis, inflammatory bone disorders and pulmonary tuberculosis Preferably said circulatory disease includes, for example, any one of the following: chronic heart failure including arrhythmia, angina pectris, myocardial infarction, cardiac insufficiency and congestive heart failure, arteriosclerosis including atherosclerosis, hypertension, deep vein thrombosis, occlusive peripheral circulation failure, ischemic cerebral circulation failure, disseminated intravascular coagulation syndrome, Raynaud's disease, Buerger disease.

Preferably said allegic disease includes, for example, any one of the following: asthma, allergic rhinitis, conjunctivitis, digestive tract allergy, pollinosis and anaphylaxis, chronic occlusive pulmonary disease, collagenosis.

Preferably said neurodegenerative disease includes, for example, any one of the following: Alzheimer's disease, Parkinson's disease, amyotrophic lateral sclerosis, AIDS, encephalopathy.

Preferably said central nerve failure includes, for example, any one of the following: cerebrovascular failure such as cerebral hemorrhage and cerebral infarction and its sequela, cranial trauma, spinal damage, cerebral edema, dementia, memory failure, consciousness failure, multiple sclerosis.

Preferably said toxemia includes, for example, any one of the following: sepsis, septic shock, endotoxic shock, gram negative sepsis, toxin shock syndrome.

Preferably said cancerous tumor includes, for example, any one of the following: malignant melanoma, malignant lymphoma and cancer of the digestive organ.

Preferably said endocrine disease includes, for example, any one of the following: Addison disease, Cushing's syndrome, melanocytoma and primary aldosteronism.

Preferably said autoimmune disease includes, for example, any one of the following: organ specific diseases such as thyroiditis or non-specific organ diseases such as rheumatoid and osteo-arthritis.

Preferably said bone disease includes, for example, any one of the following: fracture, re-fracture, osteoporosis, osteomalacia, bone Behcet disease, ankylosing spondylitis, chronic rheumatoid arthritis and osteogonarthritis as well as articular tissue destruction in disease related thereto.

Preferably said neurological disorders include, for example, trauma, injury, compression to individual nerves, nerve roots, spinal cord and/or the brain, acute spinal cord and brain injure, demyelinating diseases, such as multiple sclerosis, spinal cord compression due to metastatic cancer, primary or metastatic brain tumors, chronic pain syndromes due to metastatic tumor, inflammatory CNS diseases, such as sub-acute sclerosing panenencephalitis, Huntington's disease, Guillain-Barre syndrome, Bell's palsy, diabetic neuropathy, optic neuritis, macular degeneration, retinitis pigmentosa, diabetic retinopathy, muscular dystrophy, and polymyositis-dermatomyositis.

Preferably said aberrant apoptosis includes, for example, any virally-induced inhibition of apoptosis.

Preferably said complications of diabetes mellitus or stress hyperglycemia include, for example, any one or more of the following: myocardia infarction, congestive heart failure and cardiogenic shock.

Preferably, the adiponectin is a human adiponectin or an agonist thereof.

Preferably the adiponection or adiponectin polypeptide agonist is glycosylated.

More preferably, the adiponectin is a human adiponectin or adiponectin polypeptide agonist and is glycosylated at one or more of the residues corresponding to lysine residues 65, 68, 77, and 101 of human adiponectin. It will be appreciated when referring to adiponectin of non-human species, an adiponectin variant, an adiponecting derivative or a truncated adiponectin or other adiponectin polypeptide agonist that is different from human adiponectin, the residues of the adiponectin can be referred to using the numbering of the corresponding human sequence residue, as determined by optimally aligning the two sequences.

The adiponectin preparation may be formulated in a manner suitable for administration to a human, preferably in a form for parenteral administration via routes such as subcutaneous (s.c.), intradermal (i.d.), intravenous (i.v.), intraperitoneal (i.p.) or transdermal. Other preparations are also envisaged in which said adiponectin is administered via the oral, buccal, rectal, vaginal, intravesical, intrathecal, intraventricular, intracerebral or other routes known to or desired by those skilled in the art.

The preferred routes of administration are parenteral. Adiponectin suitable for parenteral administration is formulated, for example, in aqueous solution containing buffers for stabilization, is preferably at or near isotonic strength, and with suitable antiseptic, antifoaming, anti-precipitation and other stabilizing agents known to those skilled in the art to be suitable for pharmaceutical formulation of proteins suitable for administration to mammals particularly humans, particularly those suitable for stabilization in solution of therapeutic proteins for administration to mammals preferably humans.

In a second aspect the present invention includes a method of treating a mammalian patient still able to encode for adiponectin comprising administering to the patient adiponectin and/or an agonist of the site of action of adiponectin in a sufficient amount(s) to suppress TNF-α levels below those that would have been or likely would have been present without such administration thereby to elicit a favourable response in reference to, for example, the symptoms of any one or more of the following: inflammatory disease, circulatory disease, portal hypertension, pulmonary hypertension, allegic diseases, Crohn's disease, autoimmune haemolytic anemia, psoriasis, hepatic disease, pancreatic disease, neuro-degenerative disease, central nerve failure, toxaemia, climacteric failure, gestosis, adiposis, hyperlipidemia, hypercholesteremia, abnormal glucose tolerance, solid tumor, tumor cancer and accompanying cachexia, endocrine disease, Creutzfeldt-Jakob disease, viral infection, post-percutaneous coronary arterioplasty, vascular hypertrophy or occlusion, post-PTCA/stenting/bypass surgery vascular reocclusion/restenosis, post-intervention vascular hypertrophy or occlusion, suppression of implantation-induced vascular failure and rejection, rejection episodes following organ or tissue transplant and automimmune disease, side effects associated with TNF generation during neoplastic therapy and also to eliminate or ameliorate shock related symptoms associated with the treatment or prevention of graft rejection, dialytic hypotension, glaucoma, high ocular tension, myasthenia gravis, chronic defatigation, bone disease, neurological disorders, TNF-α induced insulin resistance, aberrant apoptosis, complications of diabetes mellitus or stress hyperglycemia, chronic obstructive pulmonary disease, chronic bronchitis and emphysema.

Preferably said inflammatory response is any one of the following diabetic complication such as retinopathy, nephropathy, neuropathy, major vascular and microvascular disorders, diabetic nephropathy; arthritis such as chronic rheumatoid arthritis, osteoarthritis, rheumatoid myelitis and periosteosis; postoperative/posttraumatic inflammation; remedy of swelling; pharyngitis; cystitis; pneumonia; myocarditis; cardiomyopathy; atopic dermatitis; inflammatory intestinal disease such as Crohn's disease and ulcerative colitis; meningitis; inflammatory ophthalmic disease; inflammatory pulmonary disease such as pneumonia, silicotuberculosis, pulmonary sarcoidosis, inflammatory bone disorders and pulmonary tuberculosis Preferably said circulatory disease includes, for example, any one of the following: chronic heart failure including arrhythmia, angina pectris, myocardial infarction, cardiac insufficiency and congestive heart failure, arteriosclerosis including atherosclerosis, hypertension, deep vein thrombosis, occlusive peripheral circulation failure, ischemic cerebral circulation failure, disseminated intravascular coagulation syndrome, Raynaud's disease, Buerger disease.

Preferably said allegic disease includes, for example, any one of the following: asthma, allergic rhinitis, conjunctivitis, digestive tract allergy, pollinosis and anaphylaxis, chronic occlusive pulmonary disease, collagenosis.

Preferably said neurodegenerative disease includes, for example, any one of the following: Alzheimer's disease, Parkinson's disease, amyotrophic lateral sclerosis, AIDS, encephalopathy.

Preferably said central nerve failure includes, for example, any one of the following: cerebrovascular failure such as cerebral hemorrhage and cerebral infarction and its sequela, cranial trauma, spinal damage, cerebral edema, dementia, memory failure, consciousness failure, multiple sclerosis.

Preferably said toxemia includes, for example, any one of the following: sepsis, septic shock, endotoxic shock, gram negative sepsis, toxin shock syndrome.

Preferably said cancerous tumor includes, for example, any one of the following: malignant melanoma, malignant lymphoma and cancer of the digestive organ.

Preferably said endocrine disease includes, for example, any one of the following: Addison disease, Cushing's syndrome, melanocytoma and primary aldosteronism.

Preferably said autoimmune disease includes, for example, any one of the following organ specific diseases such as thyroiditis or non-specific organ diseases such as rheumatoid and osteo-arthritis.

Preferably said bone disease includes, for example, any one of the following: racture, re-fracture, osteoporosis, osteomalacia, bone Behcet disease, ankylosing spondylitis, chronic rheumatoid arthritis and osteogonarthritis as well as articular tissue destruction in disease related thereto.

Preferably said neurological disorders include, for example, trauma, injury, compression to individual nerves, nerve roots, spinal cord and/or the brain, acute spinal cord and brain injure, demyelinating diseases, such as multiple sclerosis, spinal cord compression due to metastatic cancer, primary or metastatic brain tumors, chronic pain syndromes due to metastatic tumor, inflammatory CNS diseases, such as sub-acute sclerosing panenencephalitis, Huntington's disease, Guillain-Barre syndrome, Bell's palsy, diabetic neuropathy, optic neuritis, macular degeneration, retinitis pigmentosa, diabetic retinopathy, muscular dystrophy, and polymyositis-dermatomyositis.

Preferably said aberrant apoptosis includes, for example, any virally-induced inhibition of apoptosis.

Preferably said complications of diabetes mellitus or stress hyperglycemia include, for example, any one or more of the following: myocardia infarction, congestive heart failure and cardiogenic shock.

Preferably, the mammal is a human and the adiponectin is a human adiponectin or an agonist thereof.

Preferably, the adiponectin or adiponectin agonist is full length.

Preferably the adiponection or adiponectin agonist is glycosylated at one or more sites.

More preferably, the adiponectin or adiponectin agonist is a human adiponectin or adiponectin agonist glycosylated at one or more of the residues corresponding to lysine residues 65, 68, 77, and 101 of human adiponectin. It will be appreciated when referring to adiponectin of non-human species, an adiponectin variant, an adiponectin derivative or a truncated adiponectin or polypeptide adiponectin agonist different from human adiponectin, the residues of the adiponectin can be referred to using the numbering of the corresponding human sequence residue, as determined by optimally aligning the two sequences.

The adiponectin preparation may be formulated in a manner suitable for administration to a human, preferably, for example, in a form for parenteral administration via routes such as subcutaneous (s.c.), intradermal (i.d.), intravenous (i.v.), intraperitoneal (i.p.) or transdermal. Other preparations are also envisaged in which said adiponectin is administered via the oral, buccal, rectal, vaginal, intravesical, intrathecal, intraventricular, intracerebral or other routes known to those skilled in the art.

The preferred routes of administration are parenteral. Adiponectin suitable for parenteral administration is formulated, for example, in aqueous solution containing buffers for stabilization, is preferably at or near isotonic strength, and with suitable antiseptic, antifoaming, anti-precipitation and other stabilizing agents known to those skilled in the art to be suitable for pharmaceutical formulation of proteins suitable for administration to mammals particularly humans, particularly those suitable for stabilization in solution of therapeutic proteins for administration to mammals preferably humans.

In another aspect of the present invention there is provided a method of treating a mammalian patient itself still able to encode for adiponectin comprising administering to the patient an adiponectin and/or an agonist of the site of action of adiponectin in a sufficient amount(s) to suppress TNF-α mRNA levels below those that would have been or likely would have been present without such administration.

Preferably, such administration is to treat, ameliorate, prevent and/or reverse a TNF-α disease or disorder and/or any of the characteristics of a TNF-α disease or disorder.

Preferably, the mammal is a human and the adiponectin is human adiponectin or an agonist thereof.

Preferably, the adiponectin or adiponectin agonist is full length.

Preferably the adiponection or adiponectin agonist is glycosylated at one or more sites.

More preferably, the adiponectin is a human adiponectin or adiponectin polypeptide agonist glycosylated at one or more of the residues corresponding to lysine residues 65, 68, 77, and 101 in human adiponectin.

In another aspect of the present invention there is provided a method of treating a mammalian patient itself still able to encode for adiponectin comprising administering to the patient an adiponectin and/or an agonist of the site of action of adiponectin in a sufficient amount(s) to treat, ameliorate, prevent and/or reverse a TNF-α disease or disorder and/or any of the characteristics of a TNF-α disease or disorder.

In another aspect of the present invention there is provided a method for ameliorating the harmful effects of TNF-α in a mammalian subject, comprising administering to the subject in need of such treatment a therapeutically effective amount of an adiponectin and/or an agonist of the site of action of adiponectin.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin agonist is a human adiponectin or adiponectin polypeptide agonist glycosylated at one or more of the residues corresponding to lysine residues 65, 68, 77, and 101 of human adiponectin.

In a further aspect of the invention, there is provided a method of treatment of a mammalian subject suffering from or at risk of a disease or disorder associated with an undesirably high level of TNF-α, the method comprising administering to the subject an effective amount of an adiponectin and/or an agonist of the site of action of adiponectin.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In a further aspect of the invention, there is provided a method for inhibiting and or antagonising the action of TNF-α for treating a disease or disorder involving TNF-α in a mammalian subject, the method comprising administering to the subject an effective amount of an adiponectin and/or an agonist of the site of action of adiponectin.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In another aspect the present invention includes a method of treatment of mammalian patient which includes or comprises, in any sequence, (directly or indirectly) monitoring of adiponectin in the mammalian patient, and/or the administration to the mammalian patient of an adiponectin and/or an agonist of the site of action of adiponectin, such treatment for the suppression of TNF-α levels or activity below those that would have been or likely would have been present without such administration.

Preferably, such administration is to treat, ameliorate, prevent and/or reverse a TNF-α disease or disorder and/or any of the characteristics of a TNF-α disease or disorder.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In another aspect the present invention includes a method of treatment of mammalian patient which includes or comprises, in any sequence, (directly or indirectly) monitoring of the adiponectin mRNA in the mammalian patient, and/or the administration to the mammalian patient of an adiponectin and/or an agonist of the site of action of adiponectin, such treatment being for the suppression TNF-α levels or activity below those that would have been or likely would have been present without such administration.

Preferably, such administration is to treat, ameliorate, prevent and/or reverse a TNF-α disease or disorder and/or any of the characteristics of a TNF-α disease or disorder.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In another aspect the present invention includes a method of treatment of mammalian patient which includes or comprises, in any sequence, (directly or indirectly) monitoring of adiponectin in the mammalian patient, and/or the administration to the mammalian patient of an adiponectin and/or an agonist of the site of action of adiponectin, such treatment being for the purpose of treating, reversing, or preventing a TNF-α disease or disorder and/or having the characteristics of a TNF-α disease or disorder.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is human adiponectin or adiponectin polypeptide agonist glycosylated at one or more of the residues corresponding to lysine residues 65, 68, 77, and 101 of human adiponectin.

In another aspect the present invention includes a method of treatment of mammalian patient which includes or comprises, in any sequence, (directly or indirectly) monitoring of adiponectin mRNA in the mammalian patient, and/or the administration to the mammalian patient of an adiponectin and/or an agonist of the site of action of adiponectin, such treatment being for the purpose of treating, reversing, or preventing a TNF-α disease or disorder and/or having the characteristics of a TNF-α disease or disorder.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated at one or more sites.

More preferably, the adiponectin or adiponectin polypeptide agonist is a human adiponectin or adiponectin polypeptide agonist glycosylated at one or more of the residues corresponding to lysine residues 65, 68, 77, and 101.

In still a further aspect the present invention includes the use of (preferably an effective amount of) an adiponectin and/or an agonist of the site of action of adiponectin, in the manufacture with other material or materials (whether recipients, co-actives, diluents or the like and/or whether a dosage unit defining vessel) of a dosage unit or pharmaceutical composition effective for use to suppress TNF-α levels or activity below those that would have been or likely would have been present without such administration.

Preferably, such dosage unit or pharmaceutical composition is to treat, ameliorate, prevent and/or reverse a TNF-α disease or disorder and/or any of the characteristics of a TNF-α disease or disorder.

Preferably, the mammal is a human and the adiponectin is a human adiponectin or an agonist thereof.

Preferably, the adiponectin or adiponectin polypeptide agonist is full length.

Preferably the adiponection or adiponectin polypeptide agonist is glycosylated.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In still a further aspect the present invention includes the use of (preferably an effective amount of) an adiponectin and/or an agonist of the site of action of adiponectin, in the manufacture with other material or materials (whether recipients, co-actives, diluents or the like and/or whether a dosage unit defining vessel) of a dosage unit or pharmaceutical composition effective for use in the treatment, prevention and/or reversal of a TNF-α disease or disorder and/or having the characteristics of a TNF-α disease or disorder.

Preferably, the mammal is a human and the adiponectin is a human adiponectin or agonist thereof.

Preferably, the adiponectin or adiponectin polypeptide agonist is full length.

Preferably the adiponection or adiponectin polypeptide agonist is glycosylated.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

In still a further aspect the present invention includes an article of manufacture comprising or including
  a vessel containing an adiponectin and/or an agonist of the site of action of adiponectin;
  instructions for use of adiponectin and/or an agonist of the site of action of adiponectin, (for example, as contained within the vessel) effective for use to suppress TNF-α levels below those that would have been or likely would have been present without such administration.

In still a further aspect the present invention includes an article of manufacture comprising or including
  a vessel containing an adiponectin and/or an agonist of the site of action of adiponectin;
  instructions for use of adiponectin and/or an agonist of the site of action of adiponectin, (for example, as contained within the vessel) for treating, preventing or reversing a TNF-α disease or disorder and/or any of the characteristics of a TNF-α disease or disorder.

In still a further aspect the present invention includes an article of manufacture comprising or including
  a packaging material containing an adiponectin and/or an agonist of the site of action of adiponectin;
  instructions for use of adiponectin and/or an agonist of the site of action of adiponectin, (for example, as contained within the packaging material) effective for use to suppress TNF-α levels below those that would have been or likely would have been present without such administration.

In still a further aspect the present invention includes an article of manufacture comprising or including
  a packaging material containing an adiponectin and/or an agonist of the site of action of adiponectin;
  instructions for use of adiponectin and/or an agonist of the site of action of adiponectin, (for example, as contained within the packaging material) for treating, preventing or reversing a TNF-α disease or disorder and/or any of the characteristics of a TNF-α disease or disorder.

In another aspect the present invention includes a method of treating a mammalian patient subject to or for liver disease and/or having any of the characteristics of liver disease which comprises or includes administering to that patient adiponectin and/or and/or an agonist of the site of action of adiponectin.

The liver disease may be, for example, any one or more of acute liver disease, chronic liver disease, inflammation of the liver, dysfunction of the liver, fatty liver (hepatic steatosis), fibrosis of the liver, cirrhosis of the liver, necrosis of the liver, hepatocellular necrosis, alcoholic liver disease, alcoholic hepatic steatosis, alcoholic hepatitis, alcoholic hepatic necrosis, alcoholic hepatic cirrhosis, hepatic necrosis, hepatic steatosis, hepatic steatosis associated with diabetes, hepatic steatosis associated with a diet rich in lipids, hepatic steatosis associated with abnormalities of lipid metabolism, hepatitis caused by any condition, hepatic necrosis caused by any condition, acute hepatitis, chronic hepatitis, chronic active hepatitis, hepatitis secondary to viral infection or inflammation of the liver, hepatitis A, hepatitis B, hepatitis C, hepatitis D, hepatitis E, hepatitis G, hepatitis secondary to the action of any drug or toxin, hepatitis or hepatic dysfunction consequent upon cholestasis, primary biliary cirrhosis, hepatic granulomatosis, and/or conditions in which elevated tissue or blood concentrations of tumour necrosis factor α play a pathogenic role.

Preferably, the mammal is a human and the adiponectin is human adiponectin or an agonist thereof.

Preferably, the adiponectin or adiponectin polypeptide agonist is full length.

Preferably the adiponection or adiponectin polypeptide agonist is glycosylated.

More preferably, the adiponectin or adiponectin polypeptide agonist is a human adiponectin or adiponectin polypeptide agonist glycosylated at one or more of the residues corresponding to lysine residues 65, 68, 77, and 101 of human adiponectin.

Adiponectin in respect of the treatment of human beings includes adiponectins and/or agonists thereof. Agonists are preferably related to human adiponectin such as those that may be derived by molecular biology (including recombinant techniques), microbiology, cell biology, biochemistry, nucleic acid chemistry, and immunology techniques. Adiponectins or adiponectin polypeptide agonists may be produced recombinantly by inserting a polynucleotide (usually DNA) sequence that encodes the protein into an expression vector and expressing the peptide in an appropriate host. A polynucleotide encoding the desired polypeptide, whether in fused or mature form, and whether or not containing a signal sequence to permit secretion, may be ligated into expression vectors suitable for any convenient host. Any of a variety of expression vectors known to those of ordinary skill in the art may be employed, although eukaryotic expression systems are recommended because of the ability of eukaryotic cells to perform post-translational modifications, such as glycosylation. Expression may be achieved in any appropriate host cell that has been transformed or transfected with an expression vector containing a DNA molecule which encodes the recombinant peptides. Examples of eukaryotic host cells are known in the art and include yeast, avian, insect, plant, and animal cells such as COS7, HeLa, CHO and other mammalian cells. Standard techniques for recombinant production are described for example, in Sambrook, supra. The adiponectin or adiponectin polypeptide agonist can be obtained by expression of a, for example, a recombinant polynucleotide encoding an adiponectin or a biologically active fragment thereof or a variant thereof or isoform thereof or other adiponectin polypeptide agonist in mammalian cells.

In another embodiment, an adiponectin (including mixtures of isoforms and glycoisoforms) can also be purified from an animal tissue or other source such as, but not limited to, serum or adipocytes. Methods for purifying adiponectin from adipocytes are described in U.S. patent application No. 60/349,885. The animals from which the composition of glycosylated adiponectin can be obtained include but are not limited to humans, mice, rats, dogs, bovines, and non-human primates.

In accordance with the present invention reference to an "effective amount" is to any amount alone or in concert with other such amount(s) sufficient to effect beneficial or desired results including a desired or beneficial clinical result.

We have demonstrated that a number of liver conditions, such as alcoholic liver disease, alcoholic hepatic steatosis, alcoholic hepatitis and alcoholic hepatic necrosis, diabetic steatosis and diabetes mellitus, insulin resistance secondary to a high fat diet±hepatic steatosis, are accompanied by lowered blood and adipose concentrations of adiponectin protein and adiponectin mRNA.

When adiponectin deficiency or adiponectin activity deficiency is present, ideally a sufficient amount of an active form or forms of adiponectin or an agonist(s) thereof is administered to the human or other mammal under treatment to restore the circulating, blood, tissue and/or activity levels of adiponectin to normal, or within ±5% of normal, or within ±10% of normal, or within ±25% of normal, or within ±50% of normal, or to any other desired level. Adiponectin therapy can also be effective, however, when apparently normal circulating concentrations of adiponectin or activity levels are present, so that the presence of normal adiponectin or adiponectin activity levels is not a contraindication to adiponectin or adiponectin agonist therapy.

Such an effective amount can be administered in one or more administrations by various routes of administration.

Reference herein to "mammals" include, in addition to man and mice, any appropriate mammal but is not limited to farm animals, sport animals, pets, and primates.

Such circumstances characteristics of alcoholic liver disease may be predicated by any one or more of steatosis (fatty infiltration), inflammation, necrosis, fibrosis, cirrhosis, and/or dysfunction.

A preferred dosage unit suitable for use with humans in accordance with the present invention is, for example, any form capable of providing a desired amount of adiponectin or adiponectin activity and which does not lead to lack of stability on storage nor unnecessary inactivation within the body prior to eliciting a beneficial effect.

As described an adiponectin or adiponectin agonist can also be administered by means of a surgically implanted delivery device such as an osmotic pump. As is well known in the art, alternative dosage forms suitable for administration of therapeutic protein(s) may also be used.

The invention provides glycosylated adiponectins and glycosylated polypeptide agonist thereof, and compositions of such glycosylated adiponectins adiponectins and glycosylated polypepide agonists. Such adiponectins and agonists are useful for therapeutic or pharmaceutical use (e.g., for any of the effects herein disclosed). In one aspect, the invention provides an adiponectin polypeptide or polypeptide agonist which is glycosylated and which is recombinant, isolated, purified, or synthesised. Preferably, the adiponectin polypeptide or agonist is a human adiponectin or agonist. Additionally, for example, at least one of the residues corresponding to human adiponectin lysine residues 65, 68, 77 and 101 (residues numbered according to the human peptide) is glycosylated. In one embodiment, the adiponectin or agonist is fully glycosylated. In another aspect of the invention, the sugar moieties which may be attached, for example, to the lysine residues are a glucosylgalactosyl moiety or galactosylglucosyl moiety. In another aspect, the adiponectin or adiponectin agonist polypeptide has at least one glucosylgalactosyl moiety or galactosylglucosyl moiety at each of the residues corresponding to, for example, lysine residues 68, 71, 80, and 104 (mouse) or residues 65, 68, 77, and 101 (human). In another embodiment, the adiponectin or adiponectin agonist polypeptide has a structure X1 at at least one of the residues corresponding to, for example, lysine residues 68, 71, 80, and 104 (mouse) or residues 65, 68, 77, and 101 (human) or at all of Lys-68, 71, 80, and 104 (mouse) or Lys-65, 68, 77, and 101 (human) wherein each X1 is independently selected from one or more of a glucosylgalactosyl moiety, a glucosylglucosyl moiety, a galactosylgalactosyl moiety, and galactosylglucosyl moiety. In one embodiment, all lysines in adiponectin or adiponectin agonist polypeptides are fully glycosylated.

In another aspect, the invention provides a composition containing an adiponectin or adiponectin agonist polypeptide which is glycosylated. In one embodiment, the adiponectin or adiponectin agonist polypeptide of the composition is recombinant, isolated, purified, or synthesized. In another embodiment, the adiponectin or adiponectin agonist polypeptide of the composition is a human adiponectin or adiponectin agonist. Preferably, at least one of the lysine residues corresponding, for example, to adiponectin lysine residues 65, 68, 77 and 101 (residues numbered according to the human peptide) is glycosylated. In another aspect, the composition contains a recombinant, isolated, purified, or synthesised adiponectin or adiponectin agonist polypeptide wherein at least one of the lysine residues corresponding to, for example, human adiponectin lysine residues 65, 68, 77, and 101 (or corresponding residues in other species or adiponectin variants) is glycosylated. In yet another aspect, the composition contains an adiponectin or adiponectin agonist polypeptide in which all the lysine residues (Lys-65, 68, 77, and 101) are glycosylated. In another aspect, the composition contains an adiponectin or adiponectin agonist polypeptide which has at least one sugar moiety at each of the lysine residues corresponding to lysine residues 65, 68, 77, and 101 in human adiponectin. In another embodiment, the composition contains an adiponectin which is glycosylated with a single sugar moiety. A single sugar moiety can be, for example, sialic acid, glucosyl, galactosyl, N-acetylgalactosyl, N-acetylglucosyl, sialyl Lewis X, and fucosyl. In another aspect, for example, the composition contains an adiponectin or adiponectin agonist which is glycosylated with multiple sugar moieties. In another embodiment, the composition contains an adiponectin or adiponectin agonist polypeptide which has at least one glucosylgalactosyl moiety or galactosylglucosyl moiety at each of the residues corresponding to the lysine residues 65, 68, 77, and 101 of human adiponectin. In another embodiment, the adiponectin or adiponectin agonist polypeptide has a structure X1 at at least one of, for example, the residues corresponding to the lysine residues 68, 71, 80, and 104 (mouse) or residues 65, 68, 77, and 101 (human) or at all of the residues corresponding to Lys-68, 71, 80, and 104 (mouse) or Lys-65, 68, 77, and 101 (human) wherein each X1 is independently selected from one or more of a glucosylgalactosyl moiety, a glucosylglucosyl moiety, a galactosylgalactosyl moiety, and galactosylglucosyl moiety. In another embodiment, the composition contains an adiponectin or adiponectin agonist polypeptide which has the structure X1 at all the residues corresponding to the the lysine residues 65, 68, 77, and 101 of human adiponectin. In another embodiment, the composition contains an adiponectin polypeptide which has the sequence of a naturally occurring mammalian adiponectin.

In another aspect, the invention provides a composition containing an adiponectin or adiponectin agonist polypeptide which is substantially free of at least one non-glycosylated adiponectin or adiponectin agonist isoform. In one embodiment, the composition is substantially free from adiponectin isoform 1. In another embodiment, the composition is substantially free from adiponectin isoform 2. In another embodiment, the composition is substantially free of any non-glycosylated adiponectin isoform.

In another aspect, the invention provides a composition containing an adiponectin or adiponectin agonist polypeptide wherein the predominant polypeptide species is fully glycosylated. In one embodiment, for example, the composition contains adiponectin or adiponectin agonist which has residues corresponding to residues Lys-68, 71, 80, and 104 of mouse adiponectin that are all glycosylated. In another embodiment, for example, the composition contains more than one isoform of an adiponectin or adiponectin agonist polypeptide. In another embodiment, for example, adiponectin isoform 3 is the predominant molecule in the composition. In another embodiment, adiponectin isoform 4 is the predominant molecule in the composition. In another embodiment, for example, adiponectin isoform 5 is the predominant molecule in the composition. In another embodiment, for example, adiponectin isoform 6 is the predominant molecule in the composition.

In another aspect, for example, the invention provides a composition wherein the administration of the composition to a mammal enhances the effect of insulin. In one embodiment, for example, an insulin and/or an insulin analog is included in the composition and the insulin and/or insulin analog is present in an amount or concentration sufficient to elicit a blood insulin and/or analog concentration of between about 50 pM and about 400 pM. In another embodiment, the insulin and/or insulin analog is present in an amount or concentration sufficient to elicit a blood insulin and/or insulin analog concentration of between about 100 pM and about 300 pM. In another embodiment, the insulin and/or an insulin analog is present in an amount or concentration sufficient to elicit a blood insulin and/or insulin analog concentration of at least about 200 pM.

In another aspect, the invention provides a composition of a glycosylated adiponectin or adiponectin agonist wherein the composition inhibits gluconeogenesis when administered to an individual.

In another aspect, the invention provides a method of preparing a composition comprising a glycosylated adiponectin or adiponectin agonist by obtaining a first composition containing at least two forms of adiponectin or adiponectin agonist that differ in their degree or type of glycosylation and then separating them based on the degree or type of glycosylation thereby producing a second composition that differs from the first composition in the adiponectin or adiponectin agonist profile. In one embodiment, the adiponectin or adiponectin agonist is obtained by expression of a recombinant polynucleotide encoding adiponectin or adiponectin agonist in mammalian cells. In another example, the recombinant polynucleotide encodes a polypeptide having the sequence described in FIG. 5 or a biologically active fragment thereof or a variant thereof. In another embodiment, the adiponectin is purified from an animal tissue. In another embodiment, the animal is a human, mouse, rat, dog, bovine, or a non-human primate. In another embodiment, the tissue is serum or adipocytes. In another embodiment, the separation involves a step of electrophoresis. In another embodiment, the separation does not involve a step of electrophoresis. In another embodiment, the separation comprises a step of chromatography. In another embodiment, the separation does not involve a step of chromatography. In another embodiment, the second composition is any one of the composition claims listed above.

In another aspect, the invention provides a composition made by any of the methods above.

In another aspect, the invention provides a method of diagnosing the presence or pre-disposition in an individual towards a disease state associated with adiponectin regulation by monitoring the level of a specific adiponectin isoform or expression profile of at least two glycosylated adiponectin isoforms. In one embodiment, the disease state is, for example, hyperglycemia, insulin resistance, metabolic syndromes associated with insulin resistance, Type 2 diabetes mellitus, metabolic syndromes including essential hypertension artherosclerosis, coronary heart disease, ischemic heart disease, polycystic ovary syndrome or other states associated with adiponectin deficiency or obesity. In another embodiment, the adiponectin is obtained from a biological sample. In another embodiment, at least one isoform is a fully glycosylated isoform. In another embodiment, the levels or expression patterns are obtained by determining the level or expression pattern of glycosylated adiponectin isoforms. In another embodiment, the assessment method is electrophoresis, HPLC, or mass spectrometry.

In another aspect, for example, the invention provides a method for diagnosing in an individual the presence of, or pre-disposition towards developing, a disease state by determining the level of a specific adiponectin isoform or expression profile of at least two glycosylated adiponectin isoforms in the individual and comparing the expression profile with a expression profile characteristic of an individual who is, for example, not suffering from the disease state, wherein a difference in expression profiles is indicative of the presence of or propensity to develop the disease.

In another aspect, the invention provides a method for diagnosing in an individual the presence of, or pre-disposition towards developing, a disease state by determining the level of a specific adiponectin isoform or expression profile of at least two glycosylated adiponectin isoforms in the individual and comparing the expression profile with a expression profile characteristic of an individual who is suffering from the disease state, wherein a similarity in expression profiles is indicative of the presence of or propensity to develop the disease.

In another aspect, the invention provides a method for treating a disease state associated with adiponectin or adiponectin regulation in an individual by administering an effective amount of any of the adiponectin or adiponetin agonist compositions described and claimed herein to the individual. In one embodiment, the disease state is, for example, hyperglycemia, insulin resistance, metabolic syndromes associated with insulin resistance, Type 2 diabetes mellitus, metabolic syndromes including hypertension, artherosclerosis, coronary heart disease, ischemic heart disease, polycystic ovary syndrome, or other states associated with adiponectin or obesity.

In another aspect, the invention provides the use of a glycosylated adiponectin or adiponectin agonist polypeptide in the preparation of a dosage unit or pharmaceutical composition or medicament useful, for example, i) in the treatment of a disease state associated with adiponectin regulation; or ii) to enhance the effects of insulin; or iii) to inhibit gluconeogenesis in a mammalian patient. Preferably said adiponectin or adiponectin agonist polypeptide is recombinant, isolated, purified, or synthesised. Preferably said adiponectin or adiponectin agonist is a human adiponectin or adiponectin agonist. Preferably said dosage unit or pharmaceutical composition or medicament additionally comprises an insulin or an insulin analog. Preferably the insulin or insulin analog is at a concentration sufficient to elicit a blood insulin or analog concentration of between about 50 pM and about 400 pM. Preferably the insulin or insulin analog is at a concentration sufficient to elicit a blood insulin or insulin analog concentration of between about 100 pM and about 300 pM. Preferably the insulin or insulin analog is at a concentration sufficient to elicit a blood insulin or insulin analog concentration of between about 100 pM and about 300 pM. Preferably the insulin or insulin analog is at a concentration sufficient to elicit a blood insulin or insulin analog concentration of about 200 pM.

BRIEF DESCRIPTION OF THE DRAWINGS

FIG. 5 shows that the four modified lysines (numbered 68, 71, 80 and 104 according to the murine numbering system) at the collagenous domain of adiponectin are conserved across all the species. The sequences of mouse, human, bovine, monkey and dog adiponectin are referenced to accession number BAB22597, NP_004788, AAK58902, AAK92202 and AAL09702 respectively. Four modified lysines and their surrounding motifs are highlighted.

DETAILED DESCRIPTION OF THE INVENTION

I. General Techniques

Figures 1A, 1B:
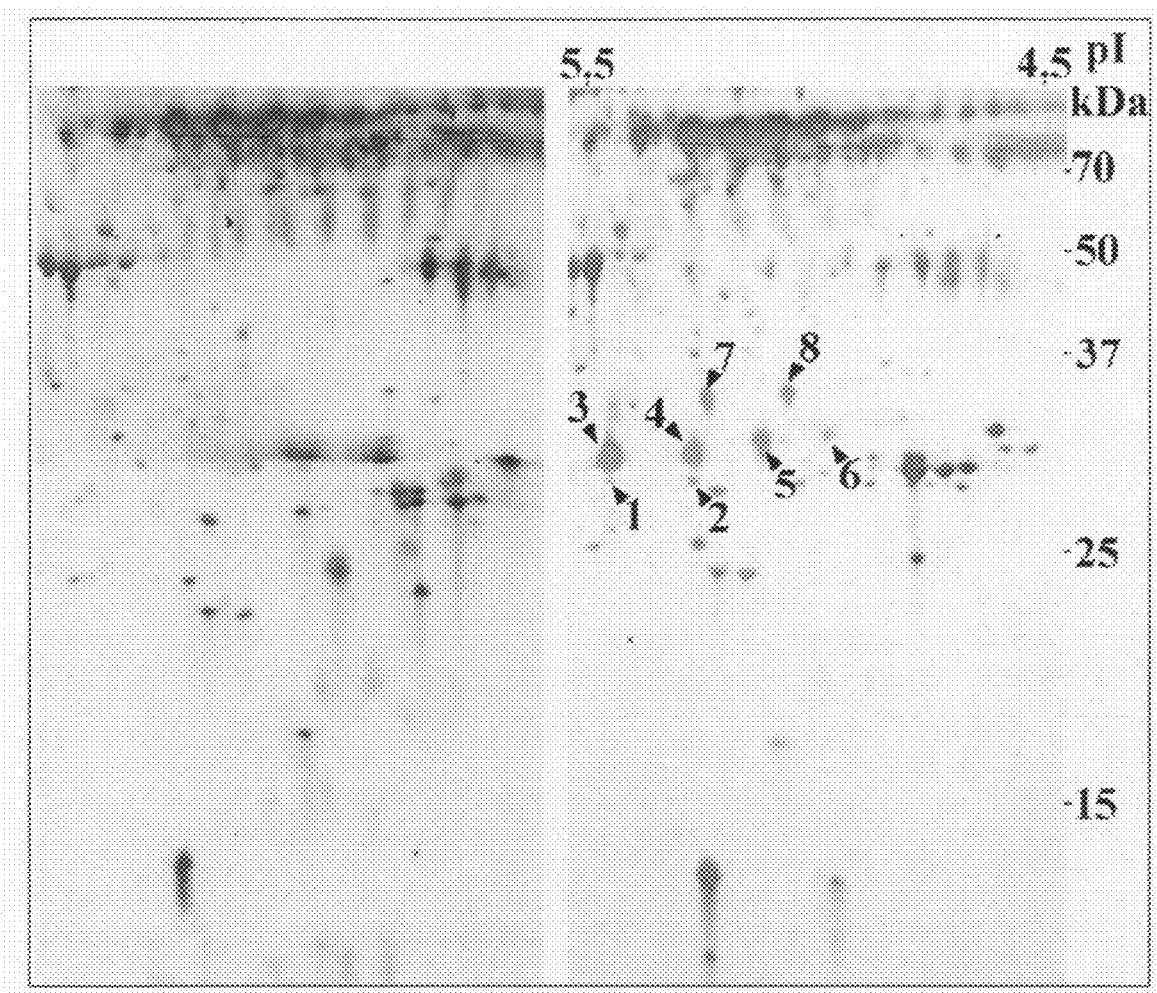
FIG. 1 shows the separation of the adipocyte-secreted proteins by 2-dimensional electrophoresis (2-DE) and multiple isoforms of adiponectin. Subconfluent 3T3-L1 preadipocytes (A) or adipocytes at 8 days after induction of differentiation (B) were rinsed with PBS for three times, and then incubated with serum free DMEM for 4 hr. The medium was collected, concentrated, and 50 μg of proteins from each sample were separated by 2-DE and visualized with silver staining as described in the experimental methods (Example 1). The proteins preferentially secreted in adipocytes were denoted by numbered arrows. In (C), secretory proteins from adipocytes were separated by 2-DE as above, transferred onto a nitrocellulose membrane, and detected by rabbit anti-adiponectin antibody at the dilution of 1:1000. Note that all the eight arrow-labeled proteins are immunoreactive to anti-adiponectin antibody.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York, and Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000).

II. Definitions

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e. g., bispecific antibodies) formed from at least two intact antibodies, single chain antibodies, diabodies, triabodies, tetrabodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (Zapata et al., *Protein Eng.*, 8 10: 1057-1062 [1995]); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 [1975], or maybe made by recombinant DNA methods (see, e. g., U.S. Pat. No. 4,816,567). The "monoclonal antibodies" may also be isolated from phage antibody libraries using techniques described, for example, in Clackson et al., Nature, 352: 624-628 [1991] and Marks et al., J. Mol. Biol., 222: 581-597 (1991).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. They also include "humanized" antibodies.

It is envisaged that monoclonal specific antibodies to each of the glycoisoforms of adiponectin as herein described can be used in the treatment or diagnosis of an adiponectin disease or disorder as herein described.

"Polyclonal Antibodies"

Methods of preparing polyclonal antibodies are known to the skilled artisan. Polyclonal antibodies can be raised in a mammal, for example, by one or more injections of an immunizing agent and, if desired, an adjuvant.

Typically, the immunising agent and/or adjuvant will be injected in the mammal by multiple subcutaneous or intraperitoneal injections. The immunizing agent may include the Adiponectin polypeptide of the present invention or a fusion protein thereof.

It may be useful to conjugate the immunising agent to a protein known to be immunogenic in the mammal being immunized. Examples of such immunogenic proteins include but are not limited to keyhole limpet hemocyanin, serum albumin, bovine thyroglobulin, and soybean trypsin inhibitor.

Examples of adjuvants which may be employed include Freund's complete adjuvant and MPL-TDM adjuvant (monophosphoryl Lipid A, synthetic trehalose dicorynomycolate). The immunisation protocol may be selected by one skilled in the art without undue experimentation.

"Monoclonal Antibodies"

Adiponectin polypeptide antibodies may, alternatively, be monoclonal antibodies. Monoclonal antibodies may be prepared using hybridoma methods, such as those described by Kohler and Milstein, Nature, 256: 495 (1975). In a hybridoma method, a mouse, hamster, or other appropriate host animal, is typically immunised with an immunising agent to elicit lymphocytes that produce or are capable of producing antibodies that will specifically bind to the immunising agent.

Alternatively, the lymphocytes may be immunised in vitro.

The immunizing agent will typically include adiponectin polypeptide, including fragments, or a fusion protein of such protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalised cell line using a suitable fusing agent, such as polyethylene glycol, to form a hybridoma cell [Goding, Monoclonal Antibodies: Principles and Practice, Academic Press, (1986) pp. 59-103]. Immortalised cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused immortalised cells.

Preferred immortalised cell lines are those that fuse efficiently, support stable high level expression of antibody by the selected antibody-producing cells, and are sensitive to a medium such as HAT medium. More preferred immortalised cell lines are murine myeloma lines, which can be obtained, for instance, from the Salk Institute Cell Distribution Center, San Diego, Calif. and the American Type Culture Collection (ATCC), Manassas, Va. Human myeloma and mouse-human heteromyeloma cell lines also have been described for the production of human monoclonal antibodies [Kozbor, J. Immunol., 133: 3001 (1984); Brodeur et al., Monoclonal Antibody Production Techniques and Applications, Marcel Dekker, Inc., New York, (1987) pp. 5163].

The culture medium in which the hybridoma cells are cultured can then be assayed for the presence of monoclonal antibodies. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107: 220 (1980).

After the desired hybridoma cells are identified, the clones may be subcloned by limiting dilution procedures and grown by standard methods. Suitable culture media for this purpose include, for example, Dulbecco's Modifie Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A Sepharose, hydroxylapatite chromatography, gel electrophoresis, dialysis, or affinity chromatography.

The monoclonal antibodies may also be made by recombinant DNA methods. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells to obtain the synthesis of monoclonal antibodies in the recombinant host cells. The DNA also may be modified.

The antibodies may be monovalent antibodies. Methods for preparing monovalent antibodies are well known in the art In vitro methods are also suitable for preparing monovalent antibodies. Digestion of antibodies to produce fragments thereof, particularly, Fab fragments, can be accomplished using routine techniques known in the art.

"Human and Humanised Antibodies"

Humanised forms of non-human (e. g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as a mouse, rat or rabbit having the desired specificity, affinity and capacity.

In some instances, Fv framework residues of the human immunoglobulin are replace by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human.

Methods for humanizing non-human antibodies are well known in the art. Generally, a humanized antibody has one or more amino acid residues introduced into it from a source which is non-human. These non human amino acid residues are often referred to as "import" residues, which are typically taken from an "import" variable domain. Humanization can be essentially performed following the method of Winter and co-workers [Jones et al., Nature, 321: 522-525 (1986); Riechmann et al., Nature, 332: 323-327 (1988); Verhoeyen et al., Science, 239: 1534-1536 (1988)], by substituting rodent CDRs or CDR sequences for the corresponding sequences of a human antibody.

Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [e.g., Hoogenboom and Winter, J. Mol. Biol., 227: 381 (1991); Marks et al., J. Mol. Biol., 222: 581 (1991)].

The techniques of Cole et al., and Berner et al., are also available for the preparation of human monoclonal antibodies (Cole et al., Monoclonal Antibodies and Cancer Therapy, Alan R. Liss, p. 77 (1985) and Berner et al., J. Immunol., 147 (1): 86-95 (1991)]. Similarly, human antibodies can be made by introducing of human immunoglobulin loci into transgenic animals, e. g., mice in which the endogenous immunoglobulin genes have been partially or completely inactivated. Upon challenge, human antibody production is observed which resembles that seen in humans in all respects, including gene rearrangement, assembly, and antibody repertoire.

"Bispecific Antibodies"

Bispecific antibodies are monoclonal, preferably human or humanized, antibodies that have binding specificities for at least two different antigens.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305: 537-539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps.

Antibody variable domains with the desired binding specificities (antibody-antigen combining sites) can be fused to immunoglobulin constant domain sequences. For further details of generating bispecific antibodies see, for example, Suresh et al., Methods in Enzymology, 121: 210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain.

In this method, one or more small amino acid side chains from the interface of the first antibody molecule are replace with larger side chains (e. g., tyrosine or tryptophan).

Compensatory "cavities" of identical or similar size to the large side chain(s) are created on the interface of the second antibody molecule by replacing large amino acid side chains with smaller ones (e. g., alanine or threonine). This provides a mechanism for increasing the yield of the heterodimer over other unwanted end-products such as homodimers.

Bispecific antibodies can be prepared as full length antibodies or antibody fragments (e. g., F(ab')2 bispecific antibodies). Techniques for generating bispecific antibodies from antibody fragments have been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med., 175: 217-225 (1992) describe the production of a fully humanized bispecific antibody F (ab') 2 molecule. Each Fab' fragment was separately secreted from E. coli and subjected to direct chemical coupling in vitro to form the bispecific antibody.

Various techniques for making and isolating bispecific antibody fragments directly from recombinant cell culture have also been described. For example, bispecific antibodies have been produced using leucine zippers.

Kostelny et al., J. Immunol., 148 (5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described, for example, by Hollinger et al., Proc. Natal. Acad. Sci. USA 90: 6444-6448 (1993) has provided an alternative mechanism for making bispecific antibody fragments. The fragments comprise a heavy-chain variable domain (VH) connect to a light-chain variable domain (VL) by a linker which is too short to allow pairing between the two domains on the same chain.

Accordingly, the VH and V, domains of one fragment are forced to pair with the complementary VL and VH domains of another fragment, thereby forcing two antigen-binding sites. Another strategy for making bispecific antibody fragments by the use of single-chain Fv (sFv) dimers has also been reported. See, Gruber et al., J. Immunol. 152: 5368 (1994).

Antibodies with more than two valences are contemplated. For example, trispecific antibodies can be prepared. Tutt et al., J. Immunol., 147: 60 (1991).

Exemplary bispecific antibodies may bind to two different epitopes on a given polypeptide herein.

Alternatively, an anti-polypeptide arm may be combine with an arm which binds to a triggering molecule on a leukocyte such as a T-cell receptor molecule (e. g., CD2, CD3, CD28, or B7), or Fc receptors for IgG (FcyR), such as FcyRI (CD64), FcyRII (CD32) and FcFyRIII (CD16) so as to focus cellular defense mechanisms to the cell expressing the particular polypeptide. Bispecific antibodies may also be used to localize cytotoxic agents to cells which express a particular polypeptide. These antibodies possess a polypeptide-binding arm and an arm which binds a cytotoxic agent or a radionuclide chelator, such as EOTUBE, DPTA, DOTA, or TETA. Another bispecific antibody of interest binds the polypeptide and further binds tissue factor (TF).

"Heteroconjugate Antibodies"

Heteroconjugate antibodies are composed of two covalently joined antibodies. It is contemplated that the antibodies may be prepared in vitro using known methods in synthetic protein chemistry, including those involving cross linking agents. For example, immunotoxins may be constructed using a disulfide exchange rection or by forming a thioether bond. Examples of suitable reagents for this purpose include iminothiolate and methyl-4mercaptobutyrimidate and those disclosed, for example, in U.S. Pat. No. 4,676,980.

"Screening assays" can be designed to find lead compounds, including but not limited to peptide compounds, that mimic to a desired level the biological activity of a native adiponectin or that interact to activate to a desired level a receptor for adiponectin. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art. The assays can be performed in a variety of formats, including protein-protein binding assays, biochemical screening assays, immunoassays, and cell-based assays, which are well characterized in the art.

"Immunoassays" include the enzyme linked immunosorbent assay (ELISA), the radioimmunoassay (RIA), Western-blot, etc. Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99M}$Tc), and fluorescent labels, such as fluorescein and rhodamine, and biotin, radioisotopes that are fluorescent, fluorescent proximity tags and all other tags known to those skilled in the art.

"Substantially homologous" or "substantially identical" refers to sequence homology wherein at least about 50% of the sequences are identical, preferably at least about 60%, preferably at least about 70%, preferably at least about 80%, and more preferably at least about 90% nucleotide or amino acid residue identity, when compared and aligned for maximum correspondence, as measured using one of the following sequence comparison algorithms or by visual inspection. Two sequences (amino acid or nucleotide) can be compared over their full-length (e.g., the length of the shorter of the two, if they are of substantially different lengths). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols In Molecular Biology, Greene Publishing and Wiley-Interscience, New York, supra). When using any of the aforementioned algorithms, the default parameters for Window length, gap penalty, etc., are used. A further indication that two nucleic acid sequences or polypeptides are substantially identical is that the first polypeptide (e.g., a polypeptide encoded by the first nucleic acid) is immunologically cross reactive with the second polypeptide (e.g., a polypeptide encoded by the second nucleic acid). Thus, a polypeptide is typically substantially identical to a second polypeptide, for example, where the two peptides differ only by conservative substitutions.

The terms "substantially pure" or "isolated," when referring to proteins and polypeptides, denote those polypeptides that are separated as desired from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least about 75%, more preferably, at least about 90%, of the total protein. Preferably, the protein will make up greater than about 90%, and more preferably, greater than about 95% of the total protein in the composition.

An "effective amount" is an amount sufficient to effect beneficial or desired results including beneficial or desired clinical results. Beneficial results can include but are not limited to an improvement in an individual's ability to be sensitized to insulin, decrease in insulin resistance, reduction in hyperglycemia, and an improvement in an individual's weight or obesity or other disease state or condition. An effective amount can be administered in one or more administrations by various routes of administration.

As used herein, "treatment" is an approach for obtaining beneficial or desired results including and preferably clinical results. Beneficial or desired clinical results include but are not limited to an improvement in an individual's ability to be sensitized to insulin, decrease in insulin resistance, reduction in hyperglycemia, and an improvement in an individual's weight or obesity or other disease state or condition. A treatment plan may occur over a period of time and may involve multiple dosages, multiple administrations, and/or different routes of administration. Generally, an effective amount of a composition comprising glycosylated adiponectin or adiponectin agonist, including a glycosylated adiponectin polypeptide agonist, is administered for treatment purposes. Adiponectin or adiponectin agonist therapy may also be effective when apparently normal circulating concentrations of adiponectin are present, so that the presence of normal adiponectin levels is not a contraindication to adiponectin therapy.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

As used herein, the terms "statistically significant," "statistically significant difference," and the like have the normal meaning in the art and means that the probability of the observed difference (or in the case of "statistically similar" measurements, the probability of a observed absence of difference) occurring by chance (the p-value) is less than some predetermined level, i.e., a p-value that is <0.05, preferably <0.01 and most preferably <0.001. A variety of suitable statistical methods are well known to those of skill can be used to measure statistical significance (e.g., standard statistical methods such as Student t-tests {for comparing two samples}, ANOVA {analysis of variance}, and confidence interval analysis; software such as the SAS System Version 8 (SAS Institute Inc., Cary, N.C., USA ) can be used for analysis).

An "individual" is a subject, for example a vertebrate, preferably a mammal, and more preferably a human, for example. Mammals include, but are not limited to, farm animals, sport animals, pets, primates, mice and rats.

As used herein the term "dosage forms" includes any appropriate dosage form well known in the art to be suitable for pharmaceutical formulation of proteins suitable for administration to mammals, and in particular to humans, particularly (although not solely) those suitable for stabilization in solution of therapeutic proteins for administration to mammals preferably humans. All this is irrespective of whether or not the adiponectin is in the form of a composition.

One example is oral delivery forms of tablet, capsule, lozenge, or the like form, or any liquid form such as syrups, aqueous solutions, emulsion and the like, capable of protecting the therapeutic protein from degradation prior to eliciting an effect, eg; in the alimentary canal if an oral dosage form.

Examples of dosage forms for transdermal delivery include transdermal patches, transdermal bandages, and the like.

Included within the topical dosage forms are any lotion, stick, spray, ointment, paste, cream, gel, etc. whether applied directly to the skin or via an intermediary such as a pad, patch or the like.

Examples of dosage forms for suppository delivery include any solid or other dosage form to be inserted into a bodily orifice (particularly those inserted rectally, vaginally and urethrally).

Examples of dosage units for transmucosal delivery include depositories, solutions for enemas, pessaries, tampons, creams, gels, pastes, foams, nebulised solutions, powders and similar formulations containing in addition to the active ingredients such carriers as are known in the art to be appropriate.

Examples of dosage units for depot administration include pellets or small cylinders of active agent or solid forms wherein the active agent is entrapped in a matrix of biodegradable polymers, microemulsions, liposomes or is microencapsulated.

Examples of implantable infusion devices include any solid form in which the active agent is encapsulated within or dispersed throughout a biodegradable polymer or synthetic, polymer such as silicone, silicone rubber, silastic or similar polymer.

Alternatively dosage forms for infusion devices may employ liposome delivery systems.

Examples of dosage units for delivery via bolus include single or multiple administrations by intravenous injection, subcutaneous, subdermal, and intramuscular administration or oral administration.

Examples of dosage units for inhalation or insulation include compositions comprising solutions and/or suspensions in pharmaceutically acceptable, aqueous, or organic solvents, or mixture thereof and/or powders.

A conservative substitution in a protein is a substitution of one amino acid with an amino acid with similar size and charge. Groups of amino acids known normally to be equivalent are understood in the art and include, for example: (a) Ala, Ser, Thr, Pro, and Gly; (b) Asn, Asp, Glu, and Gln; (c) His, Arg, and Lys; (d) Met, Glu, Ile, and Val; and (e) Phe, Tyr, and Trp.

III. Adiponectin and Adiponectin Compositions

The invention relates generally to biologically active adiponectins, adiponectin agonists including polypeptide agonists, and compositions including one or more of the foregoing. It has been surprisingly discovered that the multiple adiponectin isoforms exist and have differential biological activities. The adiponectin, adiponectin agonist, and related compositions of the invention are useful, inter alia, for therapeutic, diagnostic, and other uses. In one aspect, the invention provides an adiponectin polypeptide which is glycosylated and wherein it is recombinant, isolated, purified, or synthesised. Preferably, the adiponectin polypeptide is a human adiponectin and, for example, at least one and preferably more that one of the residues corresponding to human adiponectin lysine residues 65, 68, 77 and 101 (residues numbered according to the human peptide) is glycosylated.

In another aspect, the invention provides a composition containing an adiponectin or adiponectin agonist polypeptide wherein the adiponectin or adiponectin agonist polypeptide is glycosylated. Preferably, the adiponectin or adiponectin agonist of the composition is recombinant, isolated, purified, or synthesised. More preferably, the adiponectin or adiponectin agonist polypeptide of the composition is a human adiponectin or adiponectin agonist. Preferably, at least one of the residues corresponding to human adiponectin lysine residues 65, 68, 77 and 101 (residues numbered according to the human peptide) is glycosylated.

In another aspect, the invention provides a composition containing a recombinant, isolated, purified, or synthesized adiponectin or adiponectin agonist polypeptide in which at least one of the residues corresponding to human adiponectin lysine residues 65, 68, 77 and 101 (residues numbered according to the human peptide) is glycosylated.

Adiponectin polypeptides that differ from one another by the glycosylation (or lack thereof) at lysine residues 65, 68, 77, and 101 are sometimes referred to herein as "glycoisoforms".

A. Adiponectin Polypeptides

As used herein, an "adiponectin polypeptide" can be recombinant, isolated, purified, or synthetic. In one embodiment, the adiponectin has the sequence of a naturally occurring animal adiponectin, e.g., from a mammal, such as human, non-human primate, mouse, rat, dog, or bovine. See, for example, FIG. 5. In another embodiment, the adiponectin polypeptide is the glycosylated mature form lacking the signal sequence of the pre-pro form. In another embodiment, the adiponectin polypeptide differs from a naturally occurring adiponectin by additions to or truncations (natural or recombinant) of the native adiponectin protein and/or conservative substitutions, as well as by derivitazation. In one embodiment, the adiponectin has a sequence that is substantially similar (i.e., substantially identical) to that of a naturally occurring adiponectin, e.g., such as a sequence of FIG. 5. In one embodiment, truncated adiponectin polypeptides and conservative substitutions are substantially homologous to native adiponectin and still retain its biological activity as disclosed herein. Adiponectin polypeptides useful in the compositions of the invention include, in various embodiments, allelic variants of the adiponectins of FIG. 5, differential splice variants, alternative splice variations and other naturally occurring adiponectin variants which share substantial or desired homology to an adiponectin of FIG. 5. Other useful adiponectin variants are fragments of a full-length adiponectin, such as may be obtained by deletion of one or more amino acid residues of full-length adiponectin or truncation of full-length adiponectin. Active fragments or portions of adiponectin may be ascertained by stepwise deletions of amino acid residues, from the N-terminal end or the C-terminal end or from within the adiponectin peptide. If an amino acid is deleted and the biological activity of adiponectin is not substantially reduced, then the amino acid may not comprise a portion (or may comprise an unneeded portion) of the active fragment.

Such active fragments or portions of adiponectin may be fused with other polypeptides by methods well known in the art to yield a chimeric polypeptide. Any such chimeric polypeptides that retain the biological activity of native adiponectin are also considered to be adiponectin polypeptides of the invention.

A functional variant of adiponectin can be characterised by its biological function, wherein a functional variant of adiponectin is an agonist of the site of action of adiponectin capable of eliciting the same biological response as adiponectin. Such a functional variant is considered to be an adiponectin polypeptide as defined herein.

Whilst reference is made herein specifically to glycoclyation by a sugar or mix of sugars or more specifically to various entities such as glucosylglactosyl moieties the term includes within its scope any expansion or variation of that glycosylating moiety that elicits a similar biological activity to that more specifically identified.

Whilst reference is made herein specifically to hydroxylation the term includes within its compass any expansion or variation of that hydroxylating moiety including other modifications that elicits a similar biological activity to that more specifically identified.

Whilst reference is made herein specifically to hydroxyproline the term includes within its scope any amino acid including modified amino acids that elicits a similar biological activity to that more specifically identified.

The adiponectin preparation may be formulated in a manner suitable for administration to a human, preferably in a form for parenteral administration via routes such as subcutaneous (s.c.), intradermal (i.d.), intravenous (i.v.), intraperitoneal (i.p.) or transdermal. Other preparations are also envisaged in which said adiponectin is administered via the oral, rectal, vaginal, intravesical, intrathecal, intraventricular, intracerebral or other routes known to those skilled in the art.

The preferred routes of administration are parenteral. Adiponectins or agonists thereof suitable for parenteral administration are formulated in aqueous solution containing buffers for stabilization, preferably at or near isotonic strength, and optionally with suitable antiseptic, antifoaming, anti-precipitation and other stabilizing agents known to or learned by those skilled in the art to be suitable for pharmaceutical formulation of proteins suitable for administration to mammals particularly humans, particularly those suitable for stabilization in solution of therapeutic proteins for administration to mammals preferably humans.

In one embodiment of the invention, the composition contains an adiponectin or adiopnectin agonist polypeptide, for example, with a biological activity detectable in an in vitro assay, for example, measuring the ability of hepatocytes to respond to insulin, as shown in the Examples. In another embodiment, the adiponectin or adiopnectin agonist polypeptide has at least biological activity that is enhancement of the effect of insulin, decrease in insulin resistance in an individual, inhibition of gluconeogenesis, reduction in hyperglycemia, or improvement in the health of an individual subject to obesity, for example. In various embodiments, the biological activity of a adiponectin or adiopnectin agonist polypeptide of a composition of the invention is at least about 50%, and often at least about 95% of the an adiponectin polypeptide with a sequence shown in FIG. 5, e.g. the human adiponectin polypeptide of FIG. 5.

B. Adiponectin Isoforms

Figure 1C:
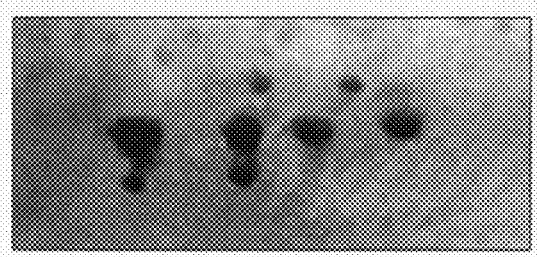
Figures 2A, 2B:
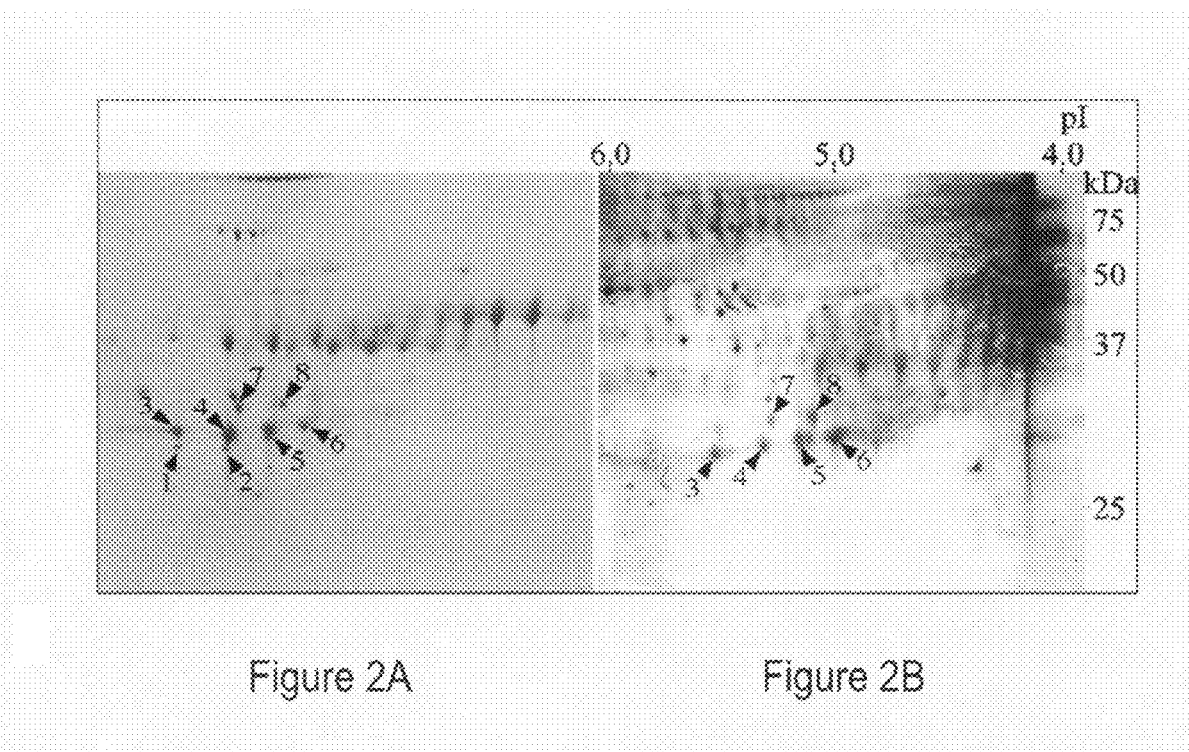
FIG. 2 shows glycoprotein detection of adipocyte-secreted products following 2-DE separation. 200 μg of the proteins harvested from the culture medium of adipocytes was separated by 2-DE as in FIG. 1, transferred onto nitrocellulose membranes and detected using an Immu-blot kit for glycoprotein detection. Eight different isoforms of adiponectin were denoted with numbered arrows as in FIG. 1.
Figure 3A:
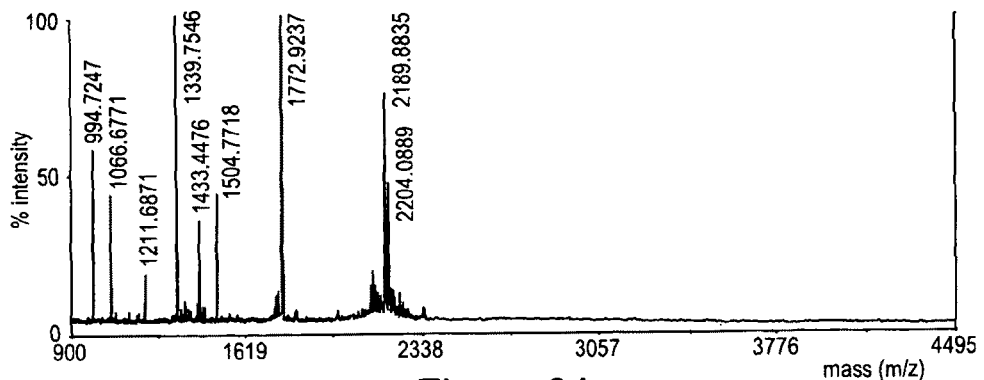
FIG. 3 shows MALDI-TOF mass spectra of the tryptic peptide mixtures derived from different isoforms of adiponectin. Bacterially produced adiponectin (A), isoform 1 (B) and isoform 3 (C) of adiponectin secreted from adipocytes, and isoform 3 of adiponectin expressed in COS-7 cells (D) were in-gel digested by trypsin, and the tryptic mixtures were analyzed by MALDI-TOF MS. Note that the three peptides (with the masses of 1679, 4260 and 4276 Da) denoted with arrows were reproducibly observed in all the glycosylated isoforms (3 to 8) produced from both adipocytes and COS-7 cells, and not in the two unglycosylated isoforms (1 and 2) or bacterially produced adiponectin.
Figure 3B:
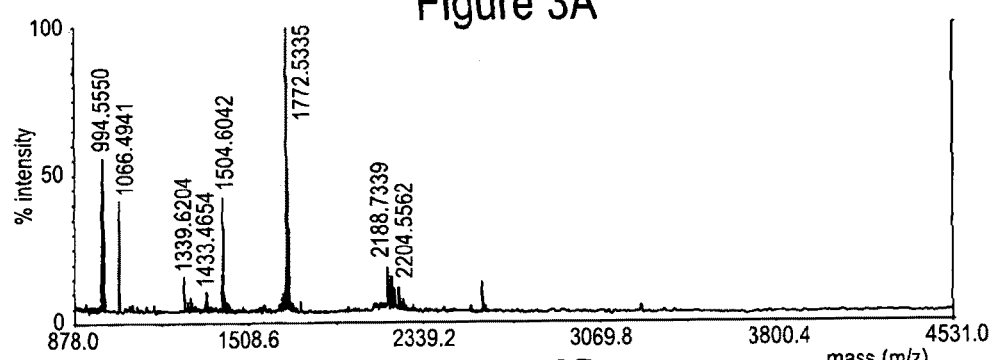
Figure 3C:
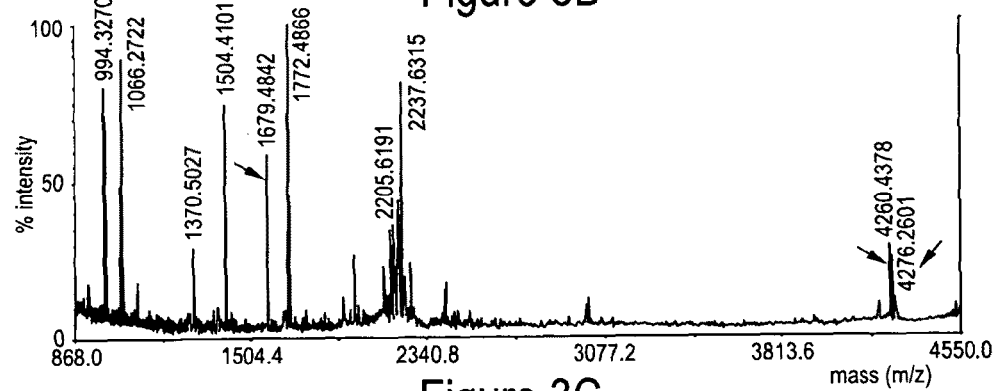
Figure 3D:
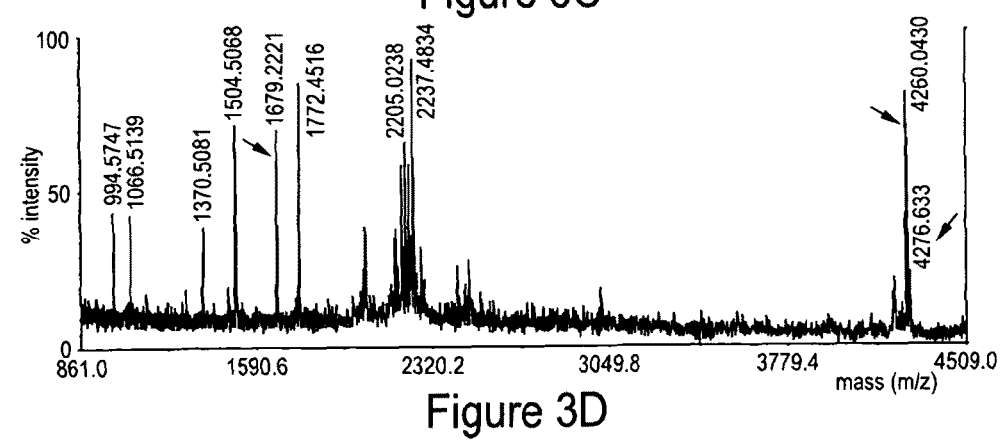

In one aspect, the invention relates to compositions containing one or more isoforms of an adiponectin. As used herein, adiponectin "isoforms" are adiponectin polypeptide forms which are distinguished on the basis of pI and apparent molecular weight. The different isoforms can be identified by standard methods such as electrophoresis. As shown in FIG. 1, adiponectin isolated from adipocytes exists in at least 8 different isoforms, which can be defined according to isoelectric point (pI) and electrophoretic mobility (apparent molecular weight) as shown in FIGS. 1 and 2. Some isoforms are glycosylated (e.g., isoforms 3, 4, 5, and 6) and others are not (e.g. isoforms 1 and 2).

C. Glycoisoforms of Adiponectin

As described below, an adiponectin made in mammalian cells can undergo post-translational modifications such as glycosylation. We have discovered that mouse adiponectin lysine residues 68, 71, 80, and 104 and correspondingly, human adiponectin lysine residues 65, 68, 77, and 101, are targets for glycosylation. In one aspect, the invention provides compositions containing, for example, human adiponectin, adiponectin from non-human species, and adiopnectin polypeptide agonist glycosylated at one or more of the residues corresponding to lysine residues 65, 68, 77, and 101 of human adiponectin. It will be appreciated when referring to adiponectin of non-human species, an adiponectin variant, or a truncated adiponectin different from the human adiponectin shown in FIG. 5, the residues of the adiponectin can be referred to using the numbering of the corresponding human sequence residue, as determined by optimally aligning the two sequences. FIG. 5 shows a sequence alignment of adiponectin for different animals. For example, in naturally occurring mouse adiponectin, the corresponding lysine residues are 68, 71, 80, and 104. It will be appreciated that, when discussing numbering in one species (e.g., human or mouse), the discussion is intended to refer also to the equivalent numbering in other species.

In one aspect, the invention provides an adiponectin or adiopnectin agonist polypeptide which is glycosylated and wherein it is recombinant, isolated, purified, or synthesised. In another embodiment, the adiponectin polypeptide is human adiponectin. In another embodiment, at least one of the lysine residues corresponding to lysine residues 68, 71, 80, and 104 (mouse) or residues 65, 68, 77, and 101 (human) is glycosylated. In one embodiment, the adiponectin is fully glycosylated. "Fully glycosylated" refers to a state of glycosylation on adiponectin polypeptide wherein all lysine residues within the adiponectin polypeptide are glycosylated with at least one sugar moiety (e.g. all four of the lysine residues corresponding to lysine residues 68, 71, 80, and 104 (mouse) or residues 65, 68, 77, and 101 (human) are glycosylated). Additional glycosylatoin may be added and/or existing glycosylation sites moved as desired for biological activity.

The glycosylation at lysine residues is typically O-linked and can result in one or more sugar moieties being added to each lysine residues. In one aspect of the invention, the sugar moieties which are added to the lysine residues are a glucosylgalactosyl moiety or galactosylglucosyl moiety. In another aspect, the adiponectin polypeptide has at least one glucosylgalactosyl moiety or galactosylglucosyl moiety at each of lysine residues 68, 71, 80, and 104 (mouse) or residues 65, 68, 77, and 101 (human), for example. In another embodiment, the adiponectin polypeptide has a structure X1 at at least one of lysine residues 68, 71, 80, and 104 (mouse) or residues 65, 68, 77, and 101 (human) or at all of Lys-68, 71, 80, and 104 (mouse) or Lys-65, 68, 77, and 101 (human) wherein each X1 is independently selected from one or more of a glucosylgalactosyl moiety, a glucosylglucosyl moiety, a galactosylgalactosyl moiety, and galactosylglucosyl moiety. In one embodiment, all lysines in adiponectin polypeptides are fully glycosylated.

The glycosylated adiponectin or adiopnectin agonist polypeptide can also be characterized by its biological effects. In one embodiment, the administration of the glycosylated adiponectin or adiopnectin agonist polypeptide to a mammal is useful to treat a disease state as herein described associated with adiponectin regulation. In another embodiment, the administration of the glycosylated adiponectin or adiopnectin agonist polypeptide to a mammal enhances the effect of insulin as described, for example, in the Examples. In another embodiment, the glycosylated adiponectin or adiopnectin agonist polypeptide inhibits gluconeogenesis when administered to an animal.

In another aspect, the invention provides a composition comprising a adiponectin or adiponectin agonist polypeptide wherein the adiponectin or adiopnectin agonist polypeptide is glycosylated. In one embodiment, the adiponectin or adiopnectin agonist polypeptide is recombinant, isolated, purified, or synthesised. In another embodiment, the adiponectin or adiopnectin agonist polypeptide is human adiponectin. In another embodiment, the composition may be formulated with or without other pharmaceutically acceptable excipients, co-actives, diluents or the like so as to be suitable for administration to mammalian patients. In another embodiment, the composition additionally comprises an insulin or an insulin analog. Preferably, the insulin or analog is at a concentration or amount sufficient to elicit a blood insulin or analog concentration of between about 50 pM and about 400 pM. Preferably, the insulin or analog is at a concentration or amount sufficient to elicit a blood insulin or analog concentration of between about 100 pM and about 300 pM. More preferably, the insulin or analog is at a concentration or amount sufficient to elicit a blood insulin concentration of about 200 pM.

In another aspect, the invention provides a composition of adiponectin or adiopnectin agonist polypeptides wherein at least one of the lysine residues corresponding to lysine residues 68, 71, 80, and 104 (mouse) or residues 65, 68, 77, and 101 (human) is glycosylated. In one embodiment, the adiponectin or adiopnectin agonist is fully glycosylated. "Fully glycosylated" refers to a state of glycosylation on an adiponectin or adiopnectin agonist polypeptide wherein all lysine or other relevant residues within the adiponectin or adiopnectin agonist polypeptide are glycosylated with at least one sugar moiety.

The glycosylation at lysine residues is typically O-linked and can result in one or more sugar moieties being added to each lysine residues. In one aspect of the invention, the sugar moieties which are added to the lysine residues are a glucosylgalactosyl moiety or galactosylglucosyl moiety. In another aspect, the adiponectin or adiopnectin agonist polypeptide has at least one glucosylgalactosyl moiety or galactosylglucosyl moiety at each of lysine residues 68, 71, 80, and 104 (mouse) or residues 65, 68, 77, and 101 (human). In another embodiment, the adiponectin or adiopnectin agonist polypeptide has a structure X1 at at least one of lysine residues 68, 71, 80, and 104 (mouse) or residues 65, 68, 77, and 101 (human) or at all of Lys-68, 71, 80, and 104 (mouse) or Lys-65, 68, 77, and 101 (human) wherein each X1 is independently selected from one or more of a glucosylgalactosyl moiety, a glucosylglucosyl moiety, a galactosylgalactosyl moiety, and galactosylglucosyl moiety. In one embodiment, all lysines in adiponectin or adiopnectin agonist polypeptides are fully glycosylated. In further embodiments, the adiponectin may be selected from any one of adiponectin isoforms 3, 4, 5, or 6.

The composition of glycosylated adiponectin or adiopnectin agonist polypeptide can also be characterized by its biological effects. In one embodiment, the administration of the composition to a mammal enhances the effect of insulin as described in the Examples. In another embodiment, the composition of glycosylated adiponectin polypeptide inhibits gluconeogenesis when administered to an animal.

In one aspect, the invention provides a composition of adiponectin that is substantially free of at least one non-glycosylated adiponectin isoform. In one aspect, the composition is substantially free from isoform 1 and/or isoform 2. In another aspect, the composition is substantially free of any non-glycosylated adiponectin isoform. As used herein, a composition is "substantially free" from an isoform when that form is less than about about 20%, preferably less than about 10%, preferably less than about 5%, most preferably less than about 1% or about 0.1% by weight of the adiponectin protein in the composition. Methods for obtaining such compositions include those disclosed in the Examples as well as methods well known in the protein purification and chromatography arts.

In yet another aspect, the invention provides a composition containing an adiponectin or agonist wherein the only or predominant adiponectin species is fully glycosylated. In one embodiment, for example, the composition contains more than one isoform of adiponectin and/or adiponectin in more than one glycosylation state. The composition can be such that any one of isoforms 3, 4, 5, or 6 is the predominant adiponectin in the composition. In this context, "predominant" refers to the composition in which at least about 50% of the adiponectin pQlypeptide in the composition is in the specified glycosylation state or of the specified isoform, preferably at least about 60%, at least about 70%, at least about 80%, at least about 90%, at least about 95%, and at least about 98% glycosylated adiponectin polypeptide.

The composition of a glycosylated adiponectin or adiponectin agonist polypeptide can also be characterized by its biological effects. In one embodiment, the administration of the composition to a mammal enhances the effect of insulin as described in the Examples. In another embodiment, the composition of glycosylated adiponectin polypeptide inhibits gluconeogenesis when administered to an animal.

D. Method of Obtaining Glycosylated Adiponectin

Several methods can be used to obtain an adiponectin composition of the invention. It will be appreciated that adiponectin or adiponectin agonist polypeptides can be produced by recombinant or synthetic means, or, as appropriate, isolated or purified from naturally occurring sources.

In one embodiment, one or more adiponectin isoforms or glycoisoforms or adiponectin agonist polypeptides is prepared by recombinant methods. Adiponectin or adiponectin agonist polypeptides may be produced recombinantly by inserting a polynucleotide (usually DNA) sequence that encodes the protein into an expression vector and expressing the peptide in an appropriate host. A polynucleotide encoding the desired polypeptide, whether in fused or mature form, and whether or not containing a signal sequence to permit secretion, may be ligated into expression vectors suitable for any convenient host. Any of a variety of expression vectors known to those of ordinary skill in the art may be employed, although eukaryotic expression systems are recommended because of the ability of eukaryotic cells to perform post-translational modifications, such as glycosylation. Expression may be achieved in any appropriate host cell that has been transformed or transfected with an expression vector containing a DNA molecule which encodes the recombinant peptides. Examples of eukaryotic host cells are known in the art and include yeast, avian, insect, plant, and animal cells such as COS7, HeLa, CHO and other mammalian cells. Standard techniques for recombinant production are described for example, in Sambrook supra. Adiponectin or adiponectin agonist polypeptides can be obtained by expression of a recombinant polynucleotide encoding adiponectin or a polypeptide having the sequence of any of those animals (e.g., human, mouse, etc.) described in FIG. 5 or a biologically active fragment or addition thereof, or other variant or agonist thereof in mammalian cells.

In another embodiment, adiponectin (including mixtures of isoforms and glycoisoforms) can also be purified from an animal tissue such as, but not limited to, serum or adipocytes. Methods for purifying adiponectin from adipocytes are well-known in the art and further described in the Examples. The animals from which the composition of glycosylated adiponectin can be obtained include but are not limited to humans, mice, rats, dogs, bovines, and non-human primates.

Adiponectin, obtained either recombinantly or from animal tissues, can be separated on the basis of molecular weight, pI, and/or the amount of glycosylation present within the adiponectin polypeptide by routine methods, e.g., electrophoresis or chromatography as disclosed in the Examples. In one aspect of the invention, adiponectin compositions containing specified isoforms or glycoisoforms of adiponectin, e.g. as described above, are prepared by differential purification. For example, according to a method of the invention, this involves obtaining a first composition containing at least two forms of adiponectin that differ in their degree or type of glycosylation and then separating the adiponectin forms based on the degree or type of glycosylation. This method produces a second composition that differs from the first composition in the adiponectin profile.

Glycosylated adiponectin polypeptide can be separated from other polypeptides by several methods known in the protein purification art. In one embodiment, the separation is effected by two-dimensional electrophoresis and subsequent excision and elution of the protein from the gel. In another embodiment, the separation is effected by using an affinity column which selects on the basis of electrical charge. In another embodiment, the separation is effected by using an affinity column loaded with lectins. In other embodiments, alternate protein purification methods are used, e.g., immunoaffinity column, size-exclusion column, lectin affinity, hydrophobic interaction, reversed phase, anion and cation exchange chromatography, and the like (see, generally, R. Scopes, *Protein Purification*, Springer-Verlag, N.Y. (1982) and Deutscher, *Methods in Enzymology* Vol. 182: Guide to Protein Purification, Academic Press, Inc. N.Y. (1990)).

In one embodiment, compositions containing predominantly glycosylated adiponectin polypeptides are obtained by using a lectin column, for example, a concanavalin A or wheat germ agglutinin column, to bind glycosylated adiponectin polypeptides. Non-glycosylated adiponectin will not bind to the column and thus, will flow through the column. The glycosylated adiponectin polypeptides are then eluted from the column to obtain a composition containing predominantly glycosylated adiponectin polypeptides.

In another embodiment, various isoforms and/or glycoisoforms are obtained by running adiponectin, either obtained recombinantly or from animal tissues, on a two-dimensional gel, identifying the glycosylated species by an antibody (as shown in the Examples), excising the spot or band of the glycosylated adiponectin isoform, and eluting the glycosylated adiponectin isoform from the band to obtain a substantially pure composition of one glycosylated adiponectin isoform. It will be recognized that compositions of the invention can be made by routine techniques, such as those described above, and including separating and recombining specific isoforms and/or glycoisoforms to prepare desired embodiments.

IV. Methods

A. Monitoring Expression

Expression of adiponectin isoforms and glycoisoforms can be monitored. In one aspect of the invention, for example, expression is monitored or determined for diagnosis of an individual with a disease state or a propensity toward a disease state associated with adiponectin regulation. In various embodiments, for example, the disease state is hyperglycemia, insulin resistance, metabolic syndromes associated with insulin resistance, metabolic syndromes associated with insulin resistance, Type 2 diabetes mellitus, Metabolic syndromes including hypertension, artherosclerosis, coronary heart disease, ischemic heart disease, polycystic ovary syndrome, or other states associated with adiponectin or obesity. The adiponectin can be obtained for example, from biological fluid such as serum or blood and analyzed by electrophoresis, HLPC, or mass spectrometry. The expression profile can be monitored for example, by any of the methods disclosed herein or known in the art (e.g., two-dimensional electrophoresis).

The monitoring can be accomplished for example, by monitoring the level of a specific adiponectin isoform, the expression profile of at least two adiponectin isoforms or glycoisoforms. In one embodiment, for example, the level or expression profiles in an individual are compared with a reference profile, where a statistically significant correlation in comparison with a reference profile is diagnostic of a condition. The reference profile for example, can be from another individual with a family history of having hyperglycemia, insulin resistance, metabolic syndromes associated with insulin resistance, Type 2 diabetes mellitus, or obesity or an individual who is suffering from hyperglycemia, insulin resistance, metabolic syndromes associated with insulin resistance, Type 2 diabetes mellitus, or obesity. The reference profile can also for example, be from a population of individuals which have been grouped according to their medical history, e.g., suffering from hyperglycemia, insulin resistance, metabolic syndromes associated with insulin resistance, Type 2 diabetes mellitus, or obesity.

Levels of expression or expression pattern of certain glycosylated adiponectin isoforms may be used in a statistical analysis to determine a range of levels or a correlate of expression patterns for a given adiponectin-associated disease state as herein described. Statistically significant correlations can then be used to determine a level or pattern of glycosylated adiponectin isoforms that would correlate to favorable (or unfavorable) prognosis. The level of expression or expression pattern of glycosylated adiponectin isoforms from a biological sample (e.g., a patient sample) can then be determined and compared to the reference levels and expression patterns to predict a clinical outcome.

In a preferred embodiment, for example, any one or more of the adiponectin isoforms utilized in the monitoring method is a human adiponectin. In another preferred embodiment, for example, the individual is a human.

B. Methods of Treatment and Preparation of Medicaments

The invention also provides a treatment, for example, of a disease state associated with adiponectin regulation in an individual. The disease state can include but is not limited to hyperglycemia, insulin resistance, metabolic syndromes associated with insulin resistance, Type 2 diabetes mellitus, metabolic syndromes including, for example, hypertension, artherosclerosis, coronary heart disease, ischemic heart disease, polycystic ovary syndrome, or other states associated with adiponectin or obesity.

A treatment plan generally includes the administration of an effective amount of a composition of glycosylated adiponectin to the individual being treated. An effective amount can be determined by assessing biological activity, for example, for insulin sensitization as disclosed in the Examples. A skilled artisan may determine the amount of a glycosylated composition by stepwise increments of dosage and assessing biological function at each step.

The composition of a glycosylated adiponectin or an adiponectin agonist may be administered in a pharmaceutically accepted excipient. Pharmaceutically acceptable excipients are known in the art, and are relatively inert substances that facilitate administration of a pharmacologically effective substance. In some embodiments, the adiponectin or adiponectin agonist compositions of the invention are formulated for administration by injection (e.g., intraperitoneally, intravenously, subcutaneously, intramuscularly, etc.).

Accordingly, a composition of glycosylated adiponectin or adiponectin agonist can be combined, for example, with pharmaceutically acceptable vehicles such as saline, Ringer's solution, dextrose solution, and the like. The particular dosage regimen, i.e., dose, timing and repetition, will depend on the particular individual and that individual's medical history. The treatment may include multiple administrations over a period of time. The treatment can be assessed for biological function using routine clinical measurements including but not limited to glucose level, glucose fasting test, and in vitro insulin sensitization test.

Antimicrobial agents in bacteriostatic or fungistatic concentrations may also be added to comply with the United States Pharmacopeia (USP). These agents must be added to preparations contained in multiple dose containers There must be an adequate concentration at the time of use to prevent the multiplication of microorganisms inadvertently introduced into the preparation while withdrawing a portion of the contents for example with a hypodermic needle.

Sodium chloride or other salt may be added to adjust the tonicity of the composition, especially for parenteral formulations that must be isotonic or substantially isotonic otherwise significant irritation and pain will occur at the site of administration.

It will be appreciated the invention also provides the use of the adiponectin and adiponectin agonist compositions disclosed herein in preparation of pharmaceutical compositions.

In yet a further aspect, the invention consists in the use of a glycosylated adiponectin or adiponectin agonist polypeptide in the preparation of a dosage unit or pharmaceutical composition or medicament useful in the treatment of a disease state associated with adiponectin regulation, or useful to enhance the effects of insulin, or useful to inhibit gluconeogenesis, in a mammalian patient. In one embodiment, the adiponectin or adiponectin agonist polypeptide is recombinant, isolated, purified, or synthesised. In another embodiment, the adiponectin or adiponectin agonist polypeptide is a human adiponectin or adiponectin agonist. In another embodiment, at least one of the residues, for example, lysine residues, corresponding to lysine residues 68, 71, 80, and 104 (mouse) or residues 65, 68, 77, and 101 (human) is glycosylated. In another embodiment, the dosage unit or pharmaceutical composition or medicament may additionally comprise an insulin or an insulin analog. Preferably, the insulin or analog is present in an amount sufficient to elicit a blood insulin concentration of between about 50 pM and about 400 pM. Preferably, the insulin or analog is at a concentration or amount sufficient to elicit a blood insulin or analog concentration of between about 100 pM and about 300 pM. More preferably, the insulin or analog is present in an amount sufficient to elicit a blood insulin or analog concentration of about 200 pM.

Suitable routes of administration of a parenteral formulation of the present invention include intramuscular, intravenous, subcutaneous, intradermal, intraarticular, intrathecal and the like. The subcutaneous route of administration is preferred. Mucosal delivery is also permissible.

It is envisaged the present invention can be co-administered or serially administered and/or mixed with an insulin or an insulin analog as a composition and/or formulation. This will depend on the situation and the patient. A suitable treatment regime may be best determined by a doctor or medical practitioner for each patient. Many insulins are available from a number of companies and include Eli Lilly & Company and Novo Nordisk. Types of insulin available are fast-, intermediate- and long-acting insulins. There are also various types of insulins within these categories. The ratio of insulin or analog and adiponectin polypeptide or adiponectin agonist will depend upon the individual needs of a particular patient. A suitable treatment regime may be best determined by a doctor or medical practitioner for each patient.

Compositions useful in the invention are prepared by mixing the ingredients following generally accepted procedures. For example, the selected components may be mixed in a blender or other standard device to produce a concentrated mixture which may then be adjusted to the final concentration and viscosity by the addition of water or thickening agent and possibly a buffer to control pH or an additional solute to control tonicity.

C. Screening

The compositions of the invention can also be used to screen for compounds which are associated with the regulation of adiponectin and more generally, with metabolism. In one embodiment, mammalian cells, e.g., cultured cells, which express adiponectin are contacted with a test compound and then changes in levels or expression pattern of adiponectin isoforms are monitored. In one embodiment, the adiponectin is expressed naturally. In another embodiment, the adiponectin is expressed recombinantly. In another embodiment, changes in the level of one or more adiponectin isoforms are detected by quantitating the amount of adiponectin isoform prior to contact with a test compound and comparing this amount to the amount detected after the cells have been contacted with the test compound. Protein quantitation is well-known in the protein chemistry art and can accomplished by, for example, Western blot. In another embodiment, adiponectin isoforms can be quantitated using a densitometer which detects relative levels of protein spots or bands. Examples of such equipment are the Laser Densitometer from Molecular Dynamics or GS-700 from Bio-Rad. In another embodiment, changes in expression pattern are detected by two-dimensional electrophoresis.

Test compounds can be of a variety of general types including, but not limited to, polypeptides; carbohydrates such as oligosaccharides and polysaccharides; polynucleotides; lipids or phospholipids; fatty acids; steroids; or amino acid analogs. The test compounds can also be of a variety of chemical types including, but not limited to, heterocyclic compounds, carbocyclic compounds, -lactams, polycarbamates, oligomeric-N-substituted glycines, benzodiazepines, thiazolidinones and imidizolidinones. Certain test agents are small molecules, including synthesized organic compounds. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642.

In one embodiment, for example, one biological function is the ability of adiponectin to sensitize hepatocytes to the effects of insulin, wherein the effect of insulin on hepatocytes is enhanced by an adiponectin polypeptide or agonist, as described in the Examples. The enhancement of the effect of insulin on hepatocytes ellicted by an adiponectin polypeptide or agonist may be determined by assays of insulin activity well known to those skilled in the art. Once such well known assay determines the effect of insulin on a cell or cells production of glucose, or gluconeogenesis. This assay can be used to determine the ability of an agent to exacerbate, enhance, or conversely attenuate, the effect of insulin. Compounds are analyzed in a step-wise manner to determine which compounds inhibit or enhance the activity of adiponectin, for example.

The following Examples are provided to illustrate but not to limit the invention in any manner.

EXAMPLES

Example 1

Experimental Procedures

Materials—Dexamethasone, 3-isobutyl-1-methylxanthine (IBMX), α-cyano-4-hydroxycinnamic acid (αCHC), collagenase, rat tail collagen type I, amino acid standards, FLAG peptide, anti-FLAG M2 affinity gel and glucose Trinder assay kit were purchased from Sigma. Human insulin (Actrapid) was obtained from Novo Nordisk. The total cellular RNA extraction reagent (TRIZOL), TEV protease, mammalian expression vectors PCDNA3.1 (+) and prokaryotic expression vector pPROEX HTb were from Invitrogen. QuikChange site-directed mutagenesis kit was from Stratagene. BCA protein assay reagent was from Pierce. Immu-Blot kit for glycoprotein detection was from Bio-Rad Laboratories. FuGENE 6 transfection reagent, trypsin and ASP-N ebdoproteinases, and the enhanced chemiluminescence (ECL) detection system were from Roche Molecular Biochemicals. The Ni-NTA agarose column was from QIAGEN. All the consumables for two-dimensional gel electrophoresis, 3H-1-galactose and 3H-1-glucose were the products of Amersham Pharmacia. All amino acid analysis reagents and Cal Mix 2 calibration standards for mass spectrometer were from Applied Biosystems.

Differentiation of 3T3-L1 cells and concentration of proteins from the cell culture medium—3T3-L1 cells were maintained as subconfluent cultures in DMEM supplemented with 10% fetal calf serum. For differentiation, cells were seeded onto 150 mm plates and allowed to reach 100% confluence, induced one-day post confluence with the above medium containing 0.25 µM dexamethasone, 0.5 mM IBMX and 10 µg/ml insulin for 2 days. This is followed by incubation with 10 µg/ml insulin for 2 days. The cells were then maintained in DMEM with 10% fetal calf serum for another 4 days.

To harvest proteins secreted from adipocytes, the cells at day 8 after differentiation were washed three times with PBS, and then incubated with serum-free medium for another 4 hr. The medium were collected, centrifuged at 3,000×g for 10 min, filtered through 0.20 µm filter, and then concentrated and desalted using a concentrator with MWCO of 5000 Da (Vivascience Ltd, Gloucestershire, UK). The proteins were then quantitated using BCA reagent, and stored at −80° C. until use.

Two-dimensional gel electrophoresis (2-DE), immunoblotting and carbohydrate detection—The proteins secreted from either adipocytes or 3T3 L1 preadipocytes were separated by 2-DE as described previously [24]. The separated proteins were stained with either silver or Coomassie Brilliant Blue R250 (CBB). For immunoblotting, proteins separated by 2-DE were transferred to nitrocellulose membranes using a Multiphor II Novablot electrophoretic transfer unit (Pharmacia). The membranes were blocked, and then incubated overnight at 4° C. with rabbit anti-adiponectin polyclonal antibody (1:1000). After incubation with horseradish-peroxidase conjugated secondary antibody for another hour at room temperature, the bound antibodies were detected by ECL detection kit. Glycoproteins were detected using a commercial Immun-Blot kit according to the manufacturer's instructions.

In-gel trypsin digestion and reversed-phase high performance liquid chromatography (RP-HPLC)—Proteins of interest separated by SDS-PAGE or 2-DE gels were excised, and gel pieces were subjected to in-gel trypsin digestion as described previously [25]. The extracted tryptic peptide mixtures were fractionated by RP HPLC on a Jupiter 5µ C18 column (250×2.00 mm, Phenomenex). The pre-warmed column (37° C.) was washed for 7 min with 0.1% trifluoroacetic acid (v/v) followed by elution using a 50 min linear gradient from 8% to 36% of acetonitrile at the flow rate of 200 µl/min. Each fraction was collected manually and subjected to ftur-ther analysis as described below. 3H-labelled glycopeptides were detected by liquid scintillation counting.

Amino acid sequencing and amino acid analysis—Protein spots separated by 2-DE were transferred to PVDF membrane, stained with CBB, excised, and subjected to amino acid sequencing using the Edman degradation method with a Perkin-Elmer (Procise, Model 492) protein sequencer. Internal amino acid sequences were obtained by sequencing the tryptic peptides following RP-HPLC fractionation.

For amino acid analysis, 5 µg of the tryptic peptides were vacuum dried and hydrolyzed in the gas phase with 6 N HCl, 1% phenol for 24 hr at 110° C. This treatment destroyed sugar residues but still permitted detection and quantitation of hydroxylysine and hydroxyproline [26]. Free amino acid residues were dissolved in 40 µl of 0.025% K3EDTA, derivatized with phenylisothiocyanate (PITC), separated on a Spheri-5 PTC 5µ column (220×2.1 mm) and analyzed by 421 amino acid analyzer (Applied Biosystems).

Matrix-assisted laser desorption ionization time of flight mass spectrometry (MALDI-TOF MS) analysis—0.5 µl of the tryptic peptide mixtures or RP-HPLC separated peptides was mixed with an equal amount of αCHC matrix (10 mg/ml in 60% acetonitril/0.3%TFA), spotted onto the sample plates and air-dried. Refelectron mass spectrometric analyses were performed on a Voyager DE PRO Biospectrometry Workstation (Applied Biosystems) using a pulsed laser beam (nitrogen laser, λ=337 nm). All ion spectra were recorded in the positive mode with the accelerating voltage of 20.0 kV. The spectrometer was externally calibrated using Cal Mix 2 standard mixture.

Cloning of mouse adiponectin-Total RNA was purified from 3T3-L1 adipocytes using TRIZOL reagent according to the manufacturer's instructions. The oligo-dT-primed cDNA from the total RNA was used as a template for PCR cloning based on mouse adiponectin nucleotide sequence (accession number: U37222). Full-length cDNA of adiponectin was then inserted into pGEMT-easy vector and its sequence was verified by DNA sequencing. The protein sequence was counted starting from the methionine residue.

Recombinant expression and purification of adiponectin and its variants—To prepare prokaryotic expression plasmid for mouse adiponectin, the DNA sequence was amplified using 5' ATCGGGATCCGAAGATGACGTTACTACAACT 3' (SEQ ID NO. 2) as the sense primer and 5' TACGAATTCT-CAGTTGGTATCATGGTAGAG 3' (SEQ ID NO. 3) as the antisense primer. The BamHI/SalI fragment of the amplified DNA product was subcloned into pPROEX HTh plasmid, resulting in an expression vector pPRO-His-Ad that encodes full-length adiponectin with 6×. His tagged at its N-terminus. A similar strategy was used for the construction of a prokaryotic expression vector pPRO-His-gAd, which expresses 6×.

His tagged globular region of adiponectin (amino acid residues between 110 and 247), except that the sense primer is 5' ATCGGGATCCGCCGCTTATATGTATCGCTC 3' (SEQ ID NO. 4). The expression of His-tagged full-length adiponectin or its globular region in BL 21 cells was induced by the addition of 1 mM of isopropyl beta-thiogalactopyranoside into the growth medium. Full-length adiponectin or its globular region was purified from the bacterial lysates using Ni-NTA agarose column according to the manufacturer's instructions. Following purification, the N-terminal tag was removed by cleavage with recombinant TEV protease. The purity of the protein was confirmed by SDS-PAGE and HPLC.

The vector for mammalian expression of adiponectin was generated by cDNA amplification using 5' GCCCGCG-GATCCATGCTACTGTTGCAAGCTCT 3' (SEQ ID NO. 5) as the sense primer and 5' GGCCGCGAATTCTCACTTGT-CATCGTCGTCCTTGTAGTCGTTGGTAT-CATGGTAGAG 3' (SEQ ID NO. 6) as the antisense primer. Following digestion with BamHI/EcoRI, the fragment was inserted into pcDNA3.1 vector to produce pcDNA-Ad-F, which encodes full-length adiponectin with FLAG epitope tagged at its C-terminus. This expression vector was then used as a template to construct the vectors encoding adiponectin variants in which the four lysines (68, 71, 80 and 104) were replaced by arginines, using a QuikChange site-directed mutagenesis kit. The mutagenic oligonucleotide primers were designed according to the criteria recommended by the manufacturer, with the codon changes from AAG to CGG (for 68 and 80) or from AAA to CGA (for 71 and 104). A plasmid (named as pcDNA-Ad (K.fwdarw.R)-F), which encodes FLAG-tagged adiponectin variant with all the four lysines substituted by arginines was obtained by sequential mutation of each site, and all the mutations were confirmed by DNA sequencing.

These mammalian expression vectors were transfected into COS-7 cells or HEK-293 cells using FuGENE 6 transfection reagent, and the cells were allowed to secrete adiponectin into serum free medium for 48 hr. The medium was then harvested and the cell debris removed by centrifugation at 3,000×g for 10 min followed by filtration through a 0.2 μm filter. The proteins were precipitated by adding 40% ammonium sulphate and stirring at 4° C. for overnight. After subsequent centrifugation at 8,000×g for 1 hr, the pellets were resuspended in TBS, dialysed against the same buffer using SnakeSkin tube with MWCO of 7000 Da. FLAG-tagged adiponectin was purified using anti-FLAG M2 affinity Gel, and eluted with 150 μg/ml of FLAG peptide.

Antibody production—The His-tagged recombinant adiponectin produced from *E. Coli* were mixed with Freund's complete adjuvant, and then intraperitoneally injected into female Wistar rats (50 μg/rat) or subcutaneously injected into female New Zealand rabbits (100 μg/rabbit). The animals were boosted twice with the same amount of protein mixed with Freund's incomplete adjuvant and the blood was collected 1 week after the last boost.

Isolation of primary rat hepatocytes and measurement of hepatic glucose production—Primary hepatocytes were prepared from male Wistar rats (200 g) using the two-step collagenase perfusion method, as described previously [27]. After isolation, the cells were washed three times in DMEM with 10% fetal bovine serum, 10 mM HEPES (pH 7.4), 2 mM L-glutamine, 100 nM dexamethasone and 1 mM insulin. The cells were centrifuged at 200 g for 2 min between each wash. Cell viability, as estimated by trypan blue exclusion, was routinely above 80% following this procedure. The cells were plated on collagen type I-coated plates in the above medium at 0.5 million cells/well in 12-well plates. The cells were allowed to adhere onto the cell culture dishes for 24 hr, and then incubated in DMEM with 5.5 mM glucose and no insulin or dexamethasone for overnight. Subsequently, the cells were stimulated with different concentration of insulin or/and adiponectin for another 24 hr. The medium was then replaced with 0.5 ml glucose-free DMEM without phenol red, supplemented with 5 mM each of alanine, valine, glycine, pyruvate and lactate. After incubation for 6 hr, the glucose level in the medium was measured using glucose Trinder assay kit.

Animals and diets—Male FVB/N mice, weighing 25 to 30 g, were housed in stainless steel, wire-bottomed cages on a 12-hour light/dark cycle under institutional guidelines for the humane treatment of laboratory animals. Mice were fed with a modified high fat/low carbohydrate liquid diet[21], containing 44% fat, 16% protein, 5.5% carbohydrate, plus 34.5% ethanol or isocaloric maltose dextrin as a control. Ethanol concentration was gradually increased from 17% to 34% during the first week of feeding, and then maintained at the same concentration for another 5 weeks.

Measurement of plasma adiponectin, TNF-α and ALT levels—Serum adiponectin levels were determined using an in-house RIA, using a rabbit polyclonal antibody against adiponectin[19]. Circulating TNF-α was quantified using a commercial ELISA kit (Chemico). Serum ALT acitivity was determined using commercial reagents from Sigma.

RNA extraction and Northern blotting—Total RNA was extracted from liver tissue using Trizol reagent (Invitrogen). 20 μg of total RNA from each sample was separated by denaturing agarose gels, transferred onto nylon membrane, and probed with $^{33}$P-labelled cDNA fragments encoding mouse TNF-α, FAS or CD36, respectively. These cDNA fragments were obtained by PCR amplification of cDNA derived from mouse liver tissues, using their specific primers. The relative mRNA abundance of each gene was quantified using phosphorimaging.

Histological analysis—Liver specimens were fixed overnight in buffered formaldehyde (10%) and embedded in paraffin. Hematoxylin-cosin stained sections were graded blindly for the degree of fatty change, inflammation and necrosis. Ten low-power fields were examined per liver. The degree of lipid infiltration was graded from 0 to 4, with 0 indicating no fat present and 4 that ≧75% of cells contain fat.

Statistical analysis—Experiments were performed routinely with five to six mice per group with values presented as mean±SE. All the studies were replicated with representative data shown. Statistical significance was determined by one-way ANOVA. In all statistical comparisons, a P value of <0.05 was used to indicate a significant difference.

Example 2

Adiponectin Secreted by Adipocytes Exists as Multiple Isoforms

2-DE analysis identified eight protein spots that were preferentially expressed and secreted from adipocytes, and not from undifferentiated 3T3-L1 preadipocytes (FIGS. 1, A and B). To identify the nature of these proteins, 500 μg of the secretory proteins harvested from adipocytes were separated by preparative 2-DE, blotted to PVDF membrane, and stained with Coomassie Brilliant Blue. N-terminal amino acid sequencing revealed that all these proteins (spot 1 to 8) share identical N-terminal sequence (EDDVTTTE), which unequivocally matches to amino acid residues between 18 and 25 of mouse adiponectin, a secretory protein expressed exclusively from adipocytes [5, 7]. This sequenced fragment (EDDVTTE) is located immediately after the hypothetical signal peptide cleavage site, suggesting that the heterogeneous isoforms of adiponectin were not caused by different protease cleavage during its secretion. The identities of these proteins as adiponectin were further confirmed by Western blotting analysis, which showed that all the eight proteins were immunoreactive to an antibody against mouse adiponectin (FIG. 1, panel C). 2-DE separation of recombinant adiponectin produced from E. coli detected only a single spot (data not shown), suggesting that the existence of multiple isoforms of adiponectin produced from adipocytes is due to post-translational modification occurred during its secretion. 2-DE analysis of recombinant adiponectin transiently expressed and secreted from COS-7 and HEK-293 cells also observed multiple isoforms of this protein, a pattern similar to those from adipocytes (data not shown).

Carbohydrate detection of proteins separated by 2-DE revealed that six isoforms of adiponectin (spot 3 to 8) derived from adipocytes are glycosylated (FIG. 2), whereas no carbohydrate was detected for adiponectin produced from E. coli (data not shown), suggesting that glycosylation may at least partly contribute to the heterogeneity of adiponectin. Although there are two consensus N-linked glycosylation sites (Asn 53 and 233), treatment with tunicamycin, an inhibitor of N-linked glycosylation [28], did not affect the glycosylation pattern (data not shown), thus excluding the possibility of N-linked glycosylation on adiponectin. A previous study using endo H treatment also suggested that no N-glycosylation occurred on adiponectin [5]. There were no potential serine and threonine residues predicted to be O-glycosylated using NetOGlyc 2.0 prediction server [29], which produces neutral network predictions of mucin type O-glycosylation sites in mammalian proteins.

Example 3

Glycosylation of Adiponectin Occurs on Several Conserved Lysine Residues at the Collagenous Domain To further characterize the nature of glycosylation and to map the glycosylation sites of adiponectin, the tryptic peptide mixtures from each isoforms of adiponectin derived from adipocytes or transiently-transfected COS-7 cells, or from E. Coli, were analyzed by MALDI-TOF MS. Comparison of the mass spectra for these samples detected three prominent peptide fragments (with the masses of 1679 Da, 4260 Da and 4276 Da respectively) which only existed in the six glycosylated isoforms, but not in the two unglycosylated isoforms or adiponectin produced from E. Coli (FIG. 3). Moreover, the masses for these three tryptic peptide fragments could not be matched to any of the unmodified tryptic fragments of adiponectin, indicating that glycosylation of adiponectin may occur within these three fragments.

Figure 4:
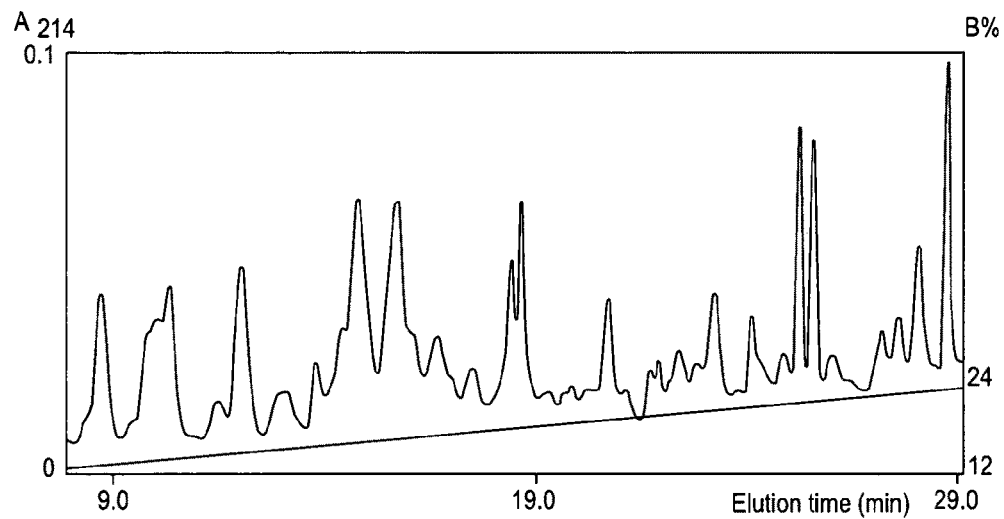
FIG. 4 shows fractionation and characterization of the tryptic peptides of adiponectin by RP-HPLC, MALDI-TOF MS and amino acid sequencing. All the glycosylated isoforms of adiponectin separated by 2-DE were excised from the gels, pooled, and digested by trypsin. The tryptic peptide mixture was separated by RP-HPLC. Each fraction was collected and analyzed by MALDI-TOF MS. The three fractions containing the peptides with masses of 1679, 4260, and 4276 Da were denoted as A, B and C respectively. The bottom table showed the amino acid sequences, the experimentally observed masses, the theoretical masses and the mass differences for these three peptides.

To isolate these three peptide fragments, the tryptic peptide mixtures from all the glycosylated isoforms were pooled, separated by RP-HPLC and each fraction was analyzed by MALDI-TOF MS (FIG. 4). This analysis found that fraction A, which was eluted at 16.4% of acetonitrile, contains the peptide with the mass of 1679 Da. The peptides with masses of 4276 Da and 4260 Da were detected in fraction B and fraction C, which were eluted at 18% and 18.4% of acetonitrile respectively. Amino acid sequence analysis identified the peptide with the mass of 1679 Da as KGEPGEAAYVYR, a fragment corresponding to amino acid residues between 104 and 115 of mouse adiponectin. The peptides with masses of 4260 Da and 4276 Da derive from the same fragment (DGTPGEKGEKGDAGLLGPKGETGDVGMTGAEGPR), which matches to amino acid residues between 62 and 95 of adiponectin. Notably, amino acid sequence analysis easily detected all the amino acid residues in these three peptide fragments, except for the four lysine residues (lysine 104 in the peptide with the mass of 1679 Da, and lysine 68, 71 and 80 in the peptides with mass of 4260 and 4276 respectively). This result indicates that these lysine residues might be modified by hydrophilic groups such as carbohydrates, and the hydrophilic amino acid derivatives could not be efficiently extracted in non-polar solvent by conventional liquid phase sequencing. The conclusion that these four lysine residues are modified was further supported by the observation that these four lysine residues were resistant to digestion by trypsin, a proteinase that specifically cleave at C-terminus of either arginine or lysine. Interestingly, all these four lysines (Lys 68, 71, 80 and 104) are located within the collagenous domain of adiponectin, with surrounding motif of GXKGE(D). Sequence alignment revealed that these four lysines and their surrounding motifs are very conserved across all the species of adiponectin (FIG. 5).

Figure 6:
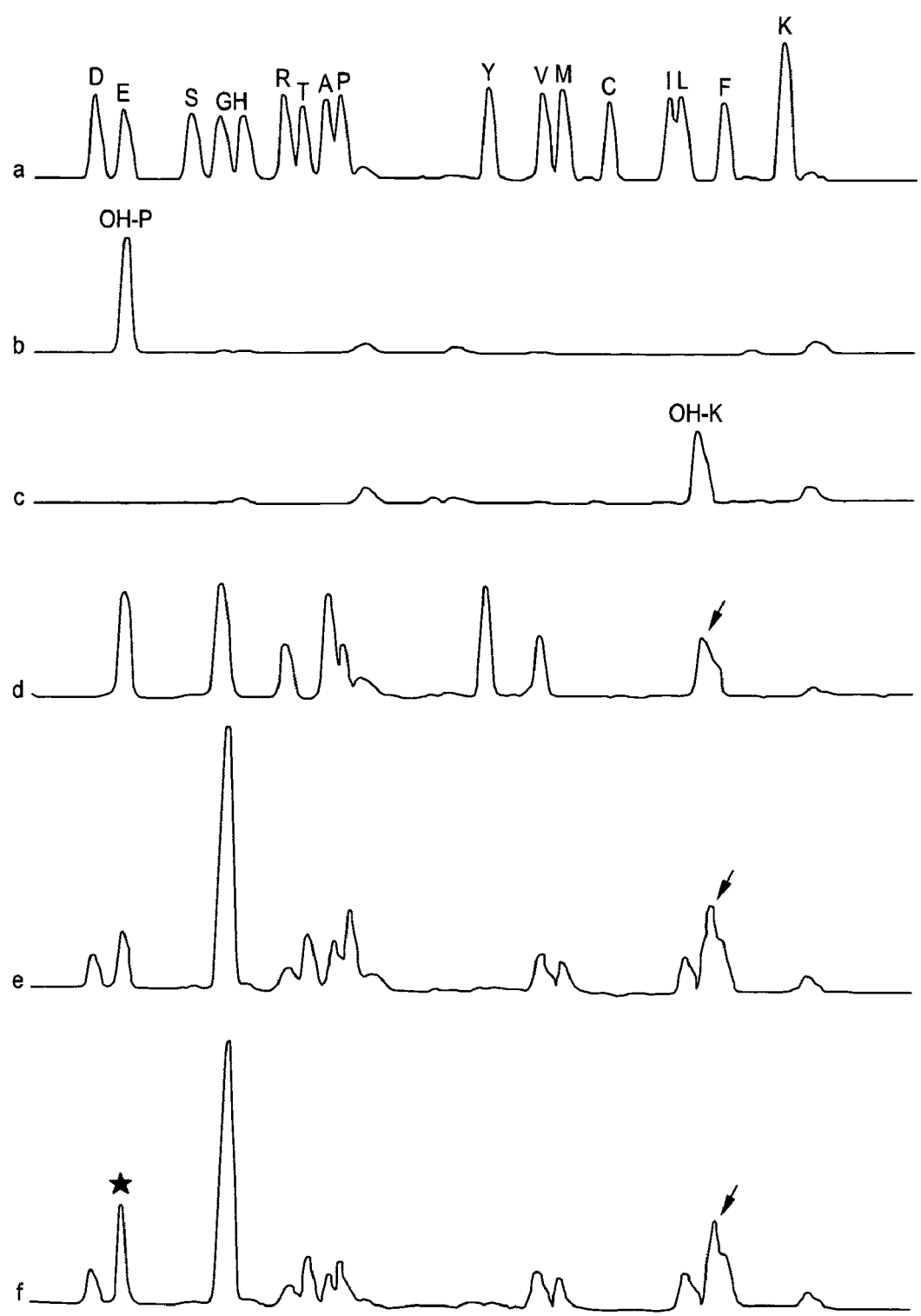
FIG. 6 shows amino acid analysis of the three tryptic peptides separated in FIG. 4. Peptide A (with the mass of 1679 Da), peptide B (with the mass of 4260 Da) and peptide C (with the mass of 4276 Da) were digested by 6N HCl at 110° C. for 24 hr (note that this treatment destroyed sugar residues but still permitted detection and quantitation of hydroxylysine and hydroxyproline [26]), the free amino acid residues were derivatized by PITC, and analyzed by 421 amino acid analyzer. a: spectrum for amino acid standard. b: spectrum for hydroxyproline standard. c: spectrum for hydroxylysine standard. d: spectrum for peptide A. e: spectrum for peptide C. f: spectrum for peptide B.

In order to verify modification of these four lysines, the three peptides purified above were further subjected to amino acid analysis, following hydrolysis with 6 N HCl for 24 hr at 110° C. The result showed the absence of lysine residues at the predicted position, although all the other amino acid residues are detected with the expected molar ratio (FIG. 6). Further analysis of these spectra revealed that all the lysine residues in these three peptides are hydroxylated. A hydroxylated proline residue was also detected within the peptide B. This hydroxyproline was subsequently assigned to Pro 94 (see below).

Hydroxylation and subsequent glycosylation of hydroxylysine to form α-1,2-glucosylgalactosyl-O-hydroxylysine (GG-Hyl) has previously been described in several secretory proteins with collagen-like domain [30, 31]. We determined that the same type of modification may occur on the four lysines (Lys 68, 71, 80 and 104) within the three tryptic peptides isolated above. This determination was supported by analysis of the MALDI-TOF MS data for these three peptides (FIG. 4). For peptide A, the difference between the experimentally observed mass (1679) and its theoretical mass (1339) is 340 Da, which is exactly the same mass for a glucosylgalactosyl hydroxyl (GG-Hyl) group. The experimentally observed mass for peptide C differs from its predicted mass by 1020 Da, an expected mass for three GG-Hyl groups that may attach to the three lysine residues (68, 71 and 80) within the peptide C. The experimentally observed mass of peptide B (4276 Da) differs from its theoretical mass by 1036 Da, which is the expected size for three GG-Hyl groups plus another hydroxyl group detected in FIG. 6.

Figure 7A:
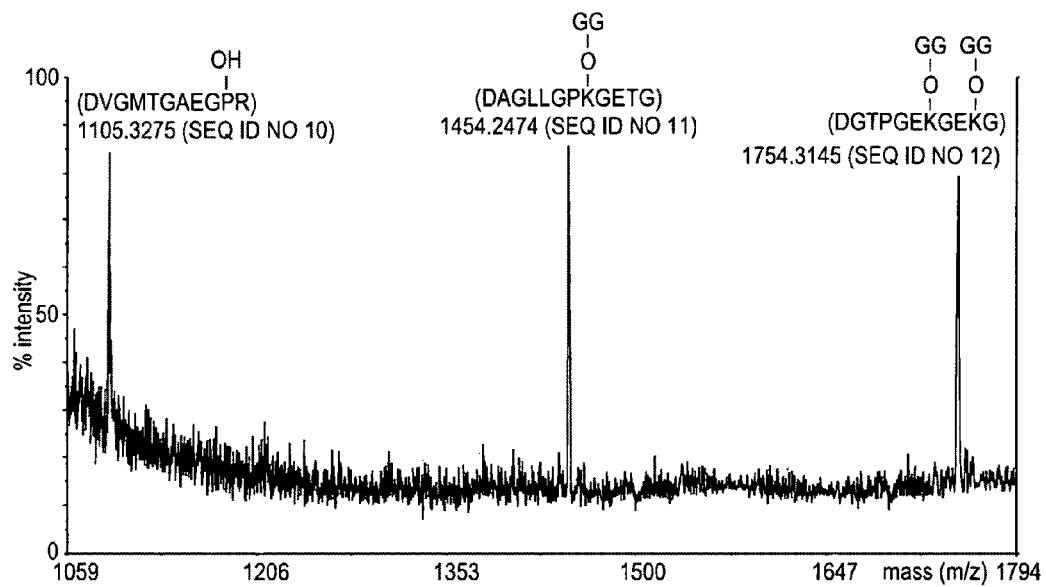
FIG. 7 shows MALDI-TOF MS spectra of peptide mixtures from Asp-N digested peptide B and C. Peptide C (I) and B (II) separated in FIG. 4 were further digested by Asp-N, and then analyzed by MALDI-TOF MS as in FIG. 3. The peptide sequences and the potential modifications assigned to each mass were indicated above each peak. Note that the assignment of Pro 94 as hydroxylated proline was also confirmed by amino acid analysis.
Figure 7B:
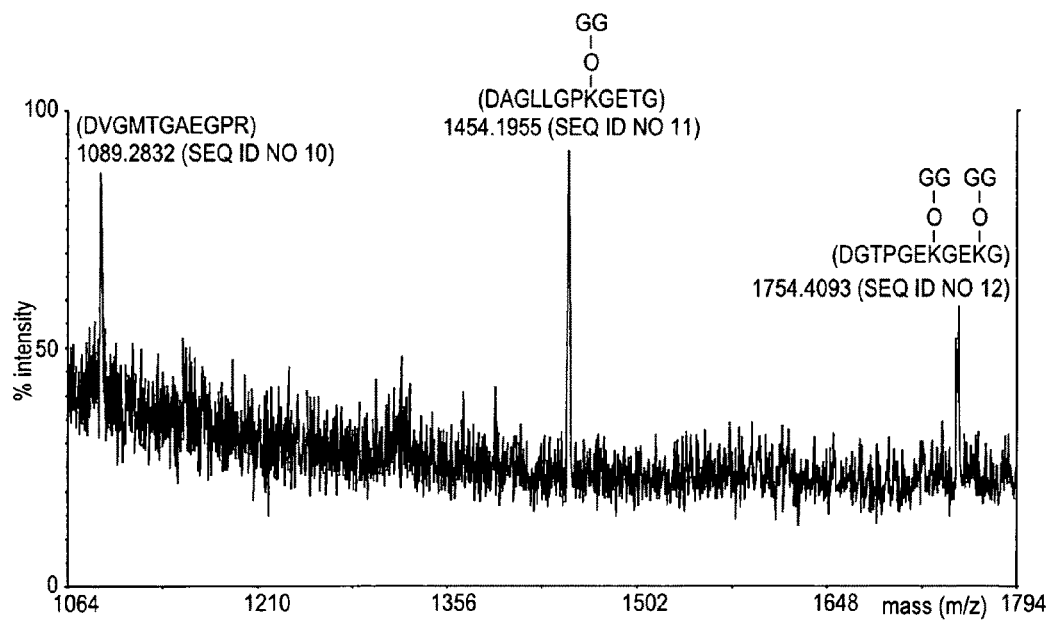

The discovery that each lysine in peptide B and C has an attached glycoside group with 340 Da was further supported by digestion of these two peptides with endoproteinase Asp-N, which specifically cleave at N-terminus of asparagine. MALDI-TOF analysis showed that the experimentally observed mass for the fragment containing Lys 80 is 340 Da larger than its theoretical mass, whereas the actual masses for the fragment containing Lys 68 and 71 differ from its theoretical mass by 680 Da (FIG. 7). This result also indicated that an extra hydroxylation within the peptide B occurred on proline 94. Hydroxylation of proline 94 was also verified by amino acid analysis and amino acid sequencing.

Figure 8:
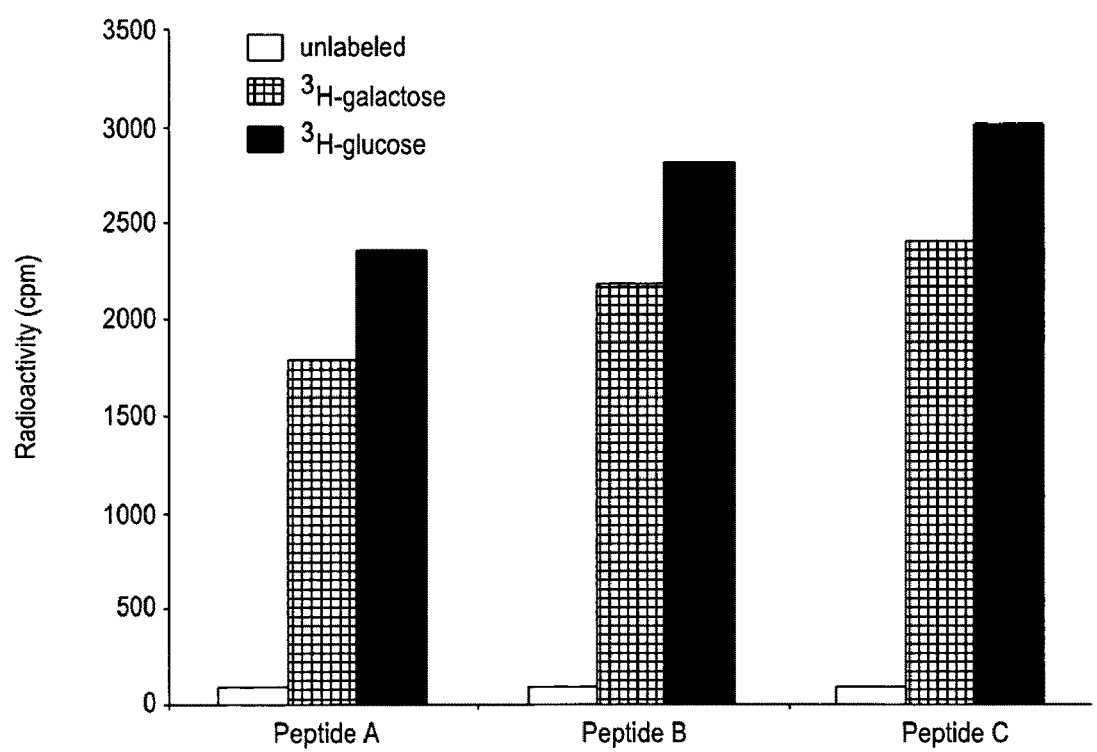
FIG. 8 shows that glycosides on the four hydroxylysines contain glucosyl and galactosyl groups. COS-7 cells were transfected with pcDNA-Ad-F, and then radiolabelled with 100 μCi/ml 3H-1-galactose in DMEM containing 2 mM glucose for 48 hr, or with 100 μCi/ml 3H-1-glucose in DMEM containing 2 mM galactose for 48 hr. FLAG-tagged adiponectin was purified from the cell culture media and tryptic peptide mixtures from unlabelled or radiolabelled adiponectin were separated by RP-HPLC as in FIG. 4 to obtain peptide A, B and C. For comparison of the radioactivity, aliquots of each peptide were subjected to liquid scintillation counting.

To confirm that the glycosides attached to the four lysine residues are glucosylgalactosyl groups, COS-7 cells transiently expressing FLAG-tagged adiponectin were radiolabelled with 3H-galactose or 3H-glucose. The tryptic mixtures of the radiolabelled adiponectin purified from these cell culture media were fractionated by RP-HPLC to isolate peptide A, B and C as in FIG. 4. Liquid scintillation counting revealed that both 3H-galactose and 3H-glucose were incorporated into these three peptides (FIG. 8).

Example 5

Figures 9A, 9B:
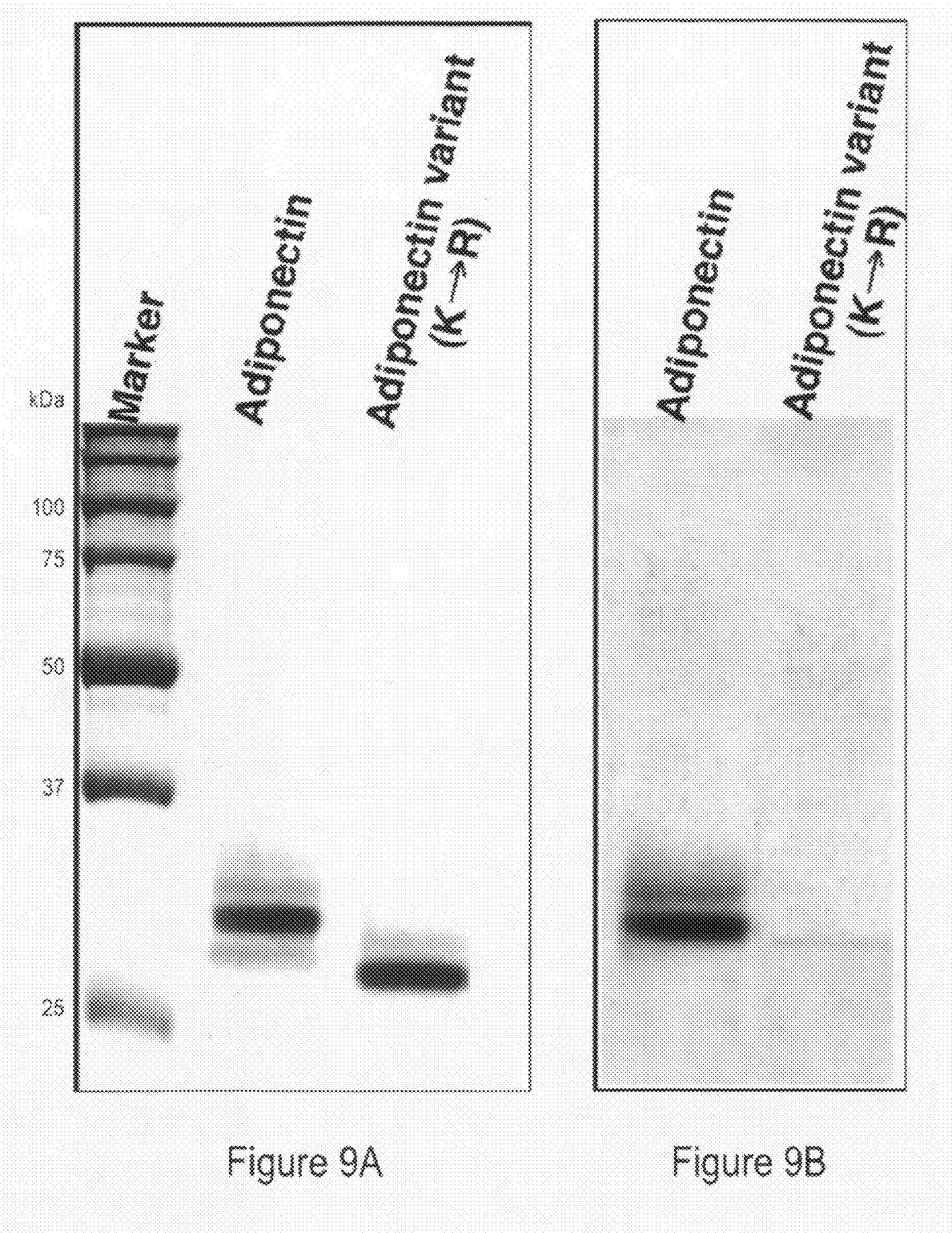
FIG. 9 shows expression and carbohydrate detection of FLAG-tagged adiponectin variant (K→R). COS-7 cells were transfected with pcDNA-Ad-F or pcDNA-Ad (K→R)-F. (Note: pcDNA-Ad-F is the pcDNA vector expressing FLAG-tagged wild-type murine adiponectin, and pcDNA-Ad (K→R)-F the equivalent vector expressing a variant of murine adiponectin in which the four lysine residues that are normally hydroxylated and glycosylated in the wild-type molecule have been mutated to arginine residues). 48 hr later, FLAG-tagged adiponectin or adiponectin variant (K→R) was purified from the cell culture media. 500 ng protein from each sample was separated by 15% SDS-PAGE, stained with Coomassie Brilliant Blue (CBB) (panel A) or detected with Immu-blot glycoprotein detection kit (panel B). Note that the majority of glycosylation was abolished in the adiponectin variant (K→R).

Substitution of the Four Lysines (68, 71, 80 and 104) at the Collagenous Domain of Adiponectin Attenuated its Insulin-Sensitizing Activity To investigate the effect of glycosylation of the four hydroxylated lysines on the biological activities of adiponectin, we generated a construct (pcDNA-Ad (K→R)-F) encoding an adiponectin variant in which the four lysines were replaced by arginines. Pulse-chase labelling of the transfected cells with 35S methionine revealed that the adiponectin variant (K→R) secreted into cell culture media at a similar rate as that of wild type adiponectin (data not shown). We thus also discovered that the modification on the four lysines at the collagenous domain is not required for its secretion. SDS-PAGE analysis revealed that wild type adiponectin secreted from COS-7 cells migrated as three bands with slightly different molecular masses (FIG. 9). The upper two bands, which account for ~85% of the total adiponectin, were glycosylated. In contrast, adiponectin variant (K→R) consisted mainly of a single unglycosylated band that migrated slightly faster than the two major glycosylated bands of wild type adiponectin. This result further confirmed our determination that glycosylation of adiponectin mainly occurs on the four lysine residues at the collagenous domain.

Figure 10:
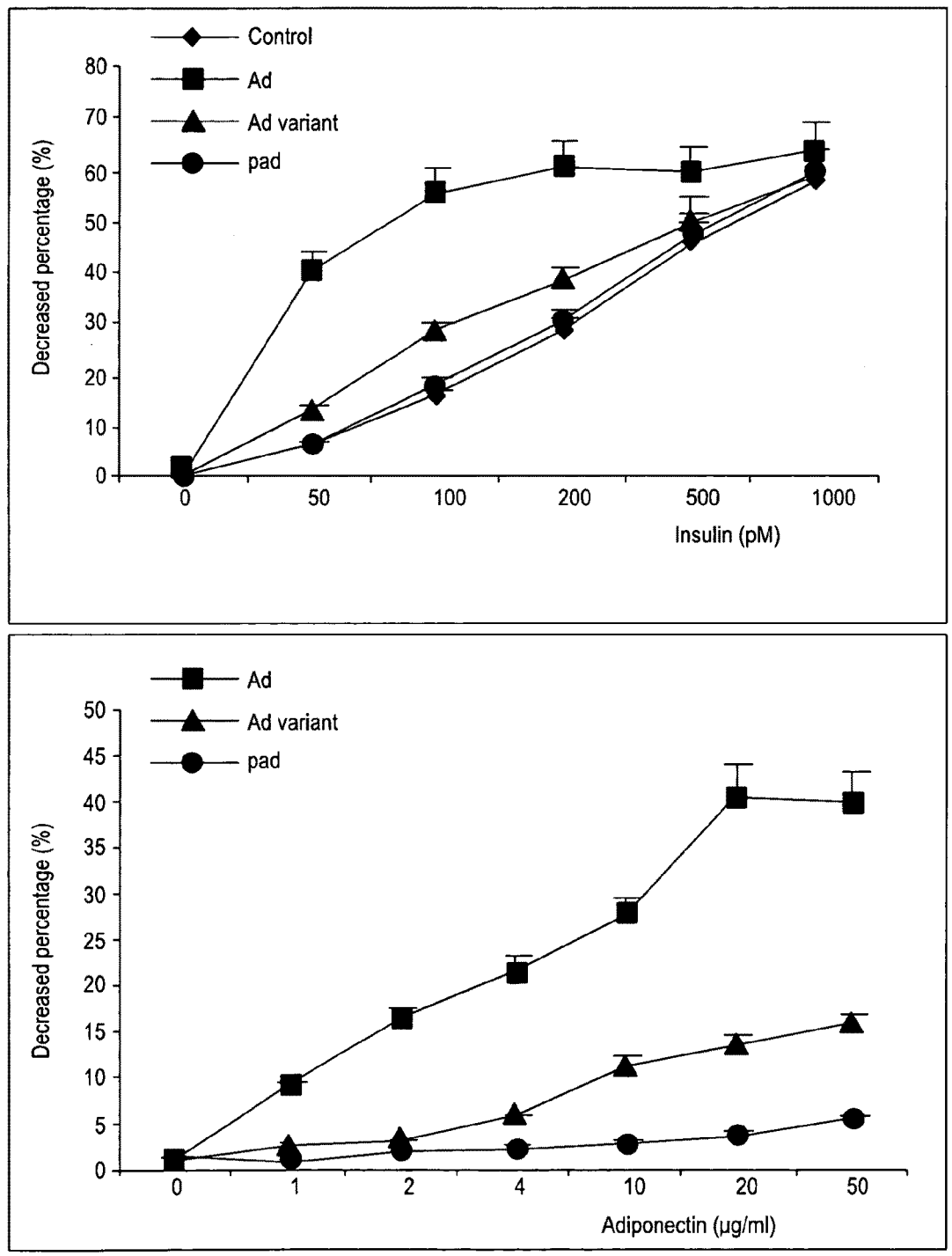
FIG. 10 shows the effect of adiponectin and adiponectin variants on insulin-evoked inhibition of glucose production in primary rat hepatocytes. Upper panel (panel A) shows the inhibition of hepatic glucose production following treatment with increasing amount of insulin in the absence or presence of 20 μg/ml of adiponectin or adiponectin variant (K→R) generated from COS-7 cells, or 20 μg/ml of bacterially produced adiponectin. Lower panel (panel B) shows the inhibition of hepatic glucose production following treatment with 50 pM insulin plus increasing amount of adiponectin or adiponectin variant (K→R) generated from COS-7 cells, or bacterially produced adiponectin. The results are represented as decreased percentage of glucose production relative to that in the untreated cells, and as mean values±standard deviation (n=4). Ad: adiponectin from COS-7 cells; Ad variant: adiponectin variant (K→R) from COS-7 cells. pAd: adiponectin from *E. Coli.*

A recent study has reported that adiponectin can enhance the action of insulin to inhibit glucose production in primary rat hepatocytes [9]. Consistent with this report, our results showed that insulin at the concentration of 50 pM, did not significantly affect the glucose production in primary rat hepatocytes (FIG. 10). The half-maximal suppression was observed at the concentration of 200 pM. The ability of sub-physiological concentration of insulin to suppress hepatic glucose production was significantly enhanced by adiponectin produced from mammalian cells. In the presence of 20 µg/ml of adiponectin, 50 pM of insulin dramatically decreased glucose production by ~40%. A concentration-dependent study revealed that the EC50 of adiponectin is at the level of ~4 µg/ml, a concentration within the physiological range of adiponectin [15, 16]. Compared to wild type adiponectin, the insulin-sensitizing ability of the adiponectin variant (K→R) on hepatic gluconeogenesis was significantly attenuated. In the presence of 4 µg/ml of the adiponectin variant, 50 pM insulin showed no significant effect on glucose production, and only caused a ∞13% decrease in the presence of 20 µg/ml of this protein. Bacterially generated full-length adiponectin (FIG. 10) and the globular region are biologically ineffective in enhancing the hepatic action of insulin to suppress gluconeogenesis.

Example 6

Biological Efficacy of Adiponectin In Vivo

We used a mouse alcohol-induced liver injury model in order to assess the efficacy when administered to a mammal of adiponectin isolated as described herein.

Mice fed with a modified high-fat liquid-control (HF/LC) diet and high-fat liquid-ethanol (HF/LE) diet[32], gained weight throughout the 6-week treatment period. Although the weight gain of HF/LC mice (7.2±0.6 g) was slightly higher, it was not significantly different from that of mice on HF/LE diet (6.8±0.5 g). Mice fed with the LE diet consumed ethanol at approximately 17-19 g/kg body weight/day. At necropsy, liver to body weight ratios in mice receiving ethanol (8.3±0.6%) were significantly higher than those in mice fed with the control diet (6.2±0.4%) (P<0.05).

Figure 11:
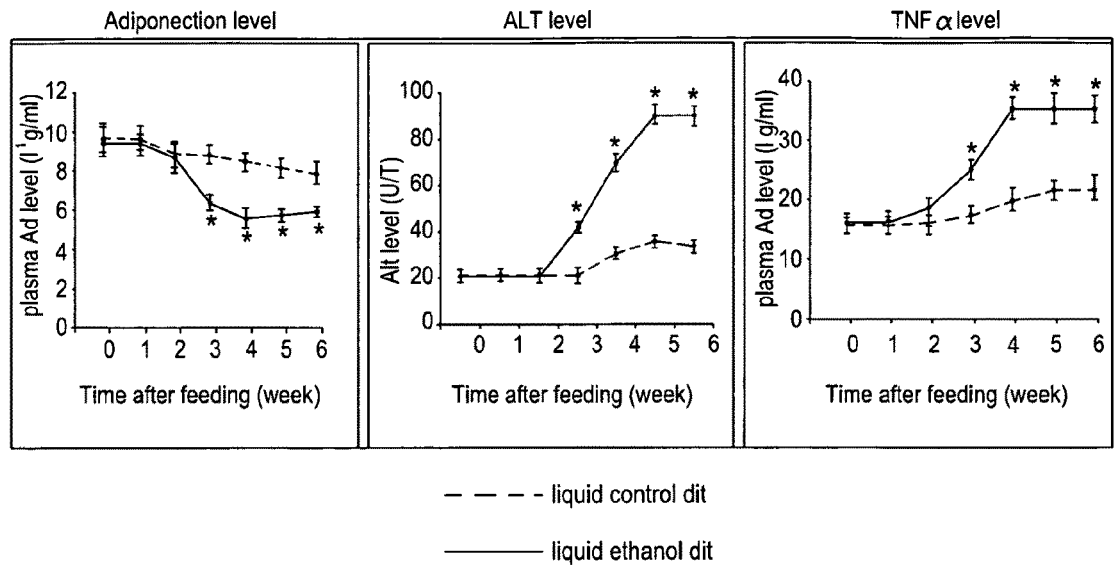
FIG. 11 shows that chronic alcohol consumption decreases plasma adiponectin, increases TNF-α and induces liver injury. Plasma samples were collected at different stages after mice had been fed with either high fat liquid control diet (dashed line) or high fat ethanol-containing diet (solid line), and were then quantified for the levels of plasma adiponectin (A), ALT (B) and TNF-α (C) as described in the text. *P<0.05 for ethanol diet vs control diet (n=6).

Chronic ethanol consumption caused a significant decrease in circulating concentrations of adiponectin. Plasma adiponectin decreased by 32.1±2.9% after three weeks, and by 40.3±4.6% after 4 weeks of feeding with the HF/LE diet (FIG. 11A). Decreased adiponectin correlates closely with the development of liver injury, as judged by the plasma level of alanine aminotransferase (ALT) activity (FIG. 11B). We discovered an inverse relationship between circulating concentrations of adiponectin and TNF-α levels following chronic consumption of the HF/LE diet (FIG. 11C). Incubation of adipocytes with TNF-α has been shown to cause a marked decrease in adiponectin expression in 3T3 L1 adipocytes[33]. We believe that TNF-α production at the early stage of alcoholic liver injury is at least partly responsible for the decreased adiponectin production during the pathogenesis of alcoholic liver injury.

Figure 12:
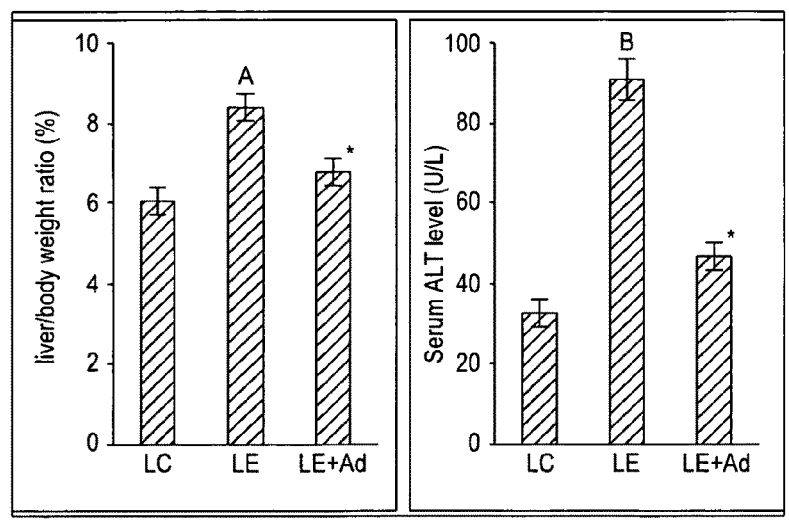
FIG. 12 shows adiponectin treatment abrogates alcohol-induced elevation of liver: body weight ratio (A) and plasma ALT concentrations (B) in mice. Plasma samples were collected after 5 weeks of liquid control diet (LC), liquid ethanol diet (LE) or liquid ethanol diet treated with adiponectin (LE+Ad) in the last two weeks, liver to body weight ratio (A) and serum ALT level (B) were determined at necropsy (n=5). *p<0.05 compared with mice receiving LE diet alone.

To investigate the effect of adiponectin on alcohol-induced liver injury, we expressed and purified full-length recombinant adiponectin from HEK293 cells transiently transfected with a vector that encodes FLAG epitope-tagged mouse adiponectin, as described by us elsewhere[34]. Three weeks after being fed with the HF/LE diet, the mice were surgically implanted with an osmotic pump (Alzet, Newark, Del.) which delivered 30 µg/day of recombinant adiponectin, or physiological saline (control). Delivery of adiponectin at this dosage caused a 2.7±0.3 fold increase in the circulating concentration of adiponectin over that of untreated LE mice. Adiponectin treatment did not significantly affect food intake, the mass of adipose tissue or weight gain. However, continuous administration of adiponectin for two weeks significantly decreased the ratio of liver to body weight (FIG. 12A). It also markedly alleviated ethanol-induced elevation of serum ALT activity (FIG. 12B).

Figure 13:
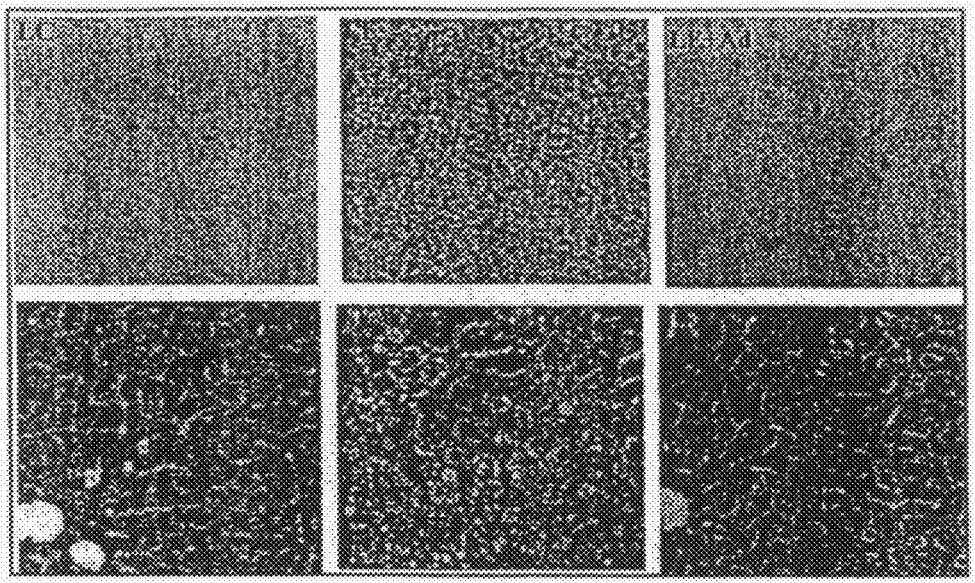
FIG. 13 shows the effects of adiponectin on alcohol-induced steatosis and inflammation. Liver specimens were taken from mouse livers after 5 weeks of liquid control diet (LC), liquid ethanol diet (LE) or liquid ethanol diet treated with adiponectin (LE+Ad) for the last two weeks, and were stained with either oil red O (upper panel) or hematoxylin and eosin (lower panel). The results are representative photomicrographs from six independent experiments.

Histological evaluation of liver specimens demonstrated massive panlobular microvesicular and macrovesicular steatosis, and occasional foci of inflammation in mice fed with HF/LE alone (FIG. 13). Administration of adiponectin dramatically decreased lipid accumulation to a background level, and largely diminished inflammation (as judged by the absence of inflammatory foci under microscopy). Our results demonstrated a protective role of adiponectin in alcohol-induced liver injury in mice.

Administration of adiponectin inhibited TNFα production and expression of fatty acid synthase and fatty acid transport protein CD36 in the liver.

Figures 14A, 14B:
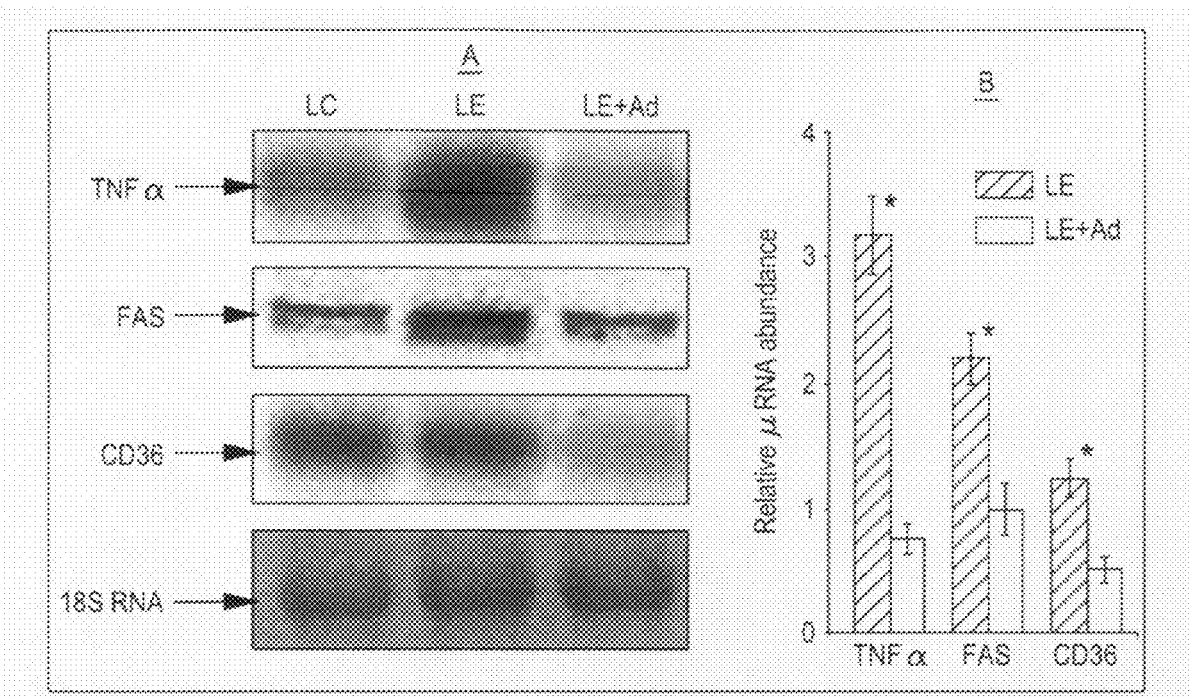
FIG. 14 shows adiponectin decreases mRNA expression of fatty acid synthase (FAS) and CD36, and suppresses TNF-α production in liver (A). Total RNA from livers of mice fed with liquid-control diet, liquid-alcohol or liquid-alcohol treated with adiponectin was extracted and subjected to Northern blot analysis using $^{33}$P-labelled TNF-α, FAS or CD36, respectively (B). The results from panel A were quantifies by phosphorimaging (n=5). All RNA levels are expressed relative to untreated HF/LC pair-fed controls, after being normalised against the abundance of 16S RNA (C). Plasma concentration of TNF-α was quantified using an ELISA kit from Chemico (n=5). ** p<0.01 HF/LE diet vs HF/LE diet plus adiponectin treatment. FAS, fatty acid synthase; TNF-α, tumor necrosis factor alpha.
Figure 14C:
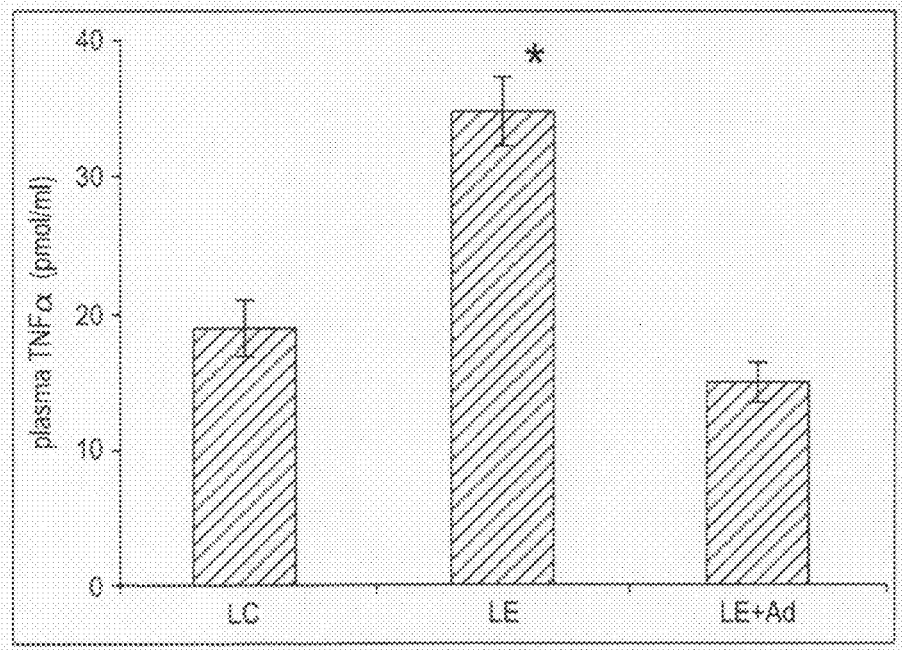

Elevated production of TNFα from Kupffer's cells within liver tissue may be a key mediator of early alcohol-induced liver injury. We believe (without wishing to be bound by the hypotheseis) that adiponectin may alleviate alcohol-induced liver injury partly by suppressing alcohol-induced elevation of TNF-α production. In testing this hypothesis, treatment of HF/LE mice with recombinant adiponectin blunted the alcohol-induced increase of circulating TNF-α as well as mRNA production of this cytokine in the liver (FIG. 14).

Without wishing to be bound by theory, in addition to suppressing TNF-α production, we believe that adiponectin may directly antagonize the damage-causing effects of TNF-α within the liver tissue. Adiponectin and TNF-α elicit many mutually opposite effects. TNF-α is reportedly a causative factor of insulin resistance while adiponectin increases insulin sensitivity[36]. Adiponectin has anti-atherogenic activity[37,38], while TNF-α contributes to the onset of atherosclerosis[39]. The antagonism between these two hormones has recently been demonstrated in muscle cells, where they impede each other's action in the regulation of glucose and lipid metabolism[40]. In hepatic tissue, TNF-α has been found to decrease insulin sensitivity and to enhance gluconeogenesis whereas adiponectin has completely opposite functions[9].

Alcohol induces lipid infiltration of liver either by inhibition of mitochondrial fatty acid β-oxidation, or by enhancing the hepatic lipogenic pathway. Ethanol oxidation increases the NADH/NAD$^+$ ratio, which in turn inhibits the NAD$^+$-requiring step in mitochondrial β-oxidation[41]. In addition, chronic ethanol consumption can increase fatty acid synthesis in humans and rodents, by inducing the expression of key enzymes in the lipogenic pathway[42,43].

We next investigated whether adiponectin suppresses hepatic lipid accumulation by interfering with any of these processes. Consistent with a previous report[41], chronic consumption of the HF/LE diet caused significant elevation of the hepatic NADH/NAD$^+$ ratio, and also significantly increased the abundance of fatty acid synthase (FAS) mRNA (FIG. 14). Adiponectin treatment had no effect on the increased NADH/NAD$^+$ ratio, but markedly decreased expression of FAS mRNA (FIG. 14). Furthermore, the expression of CD36, a fatty acid transport protein, was markedly inhibited following adiponectin treatment.

Figure 15:
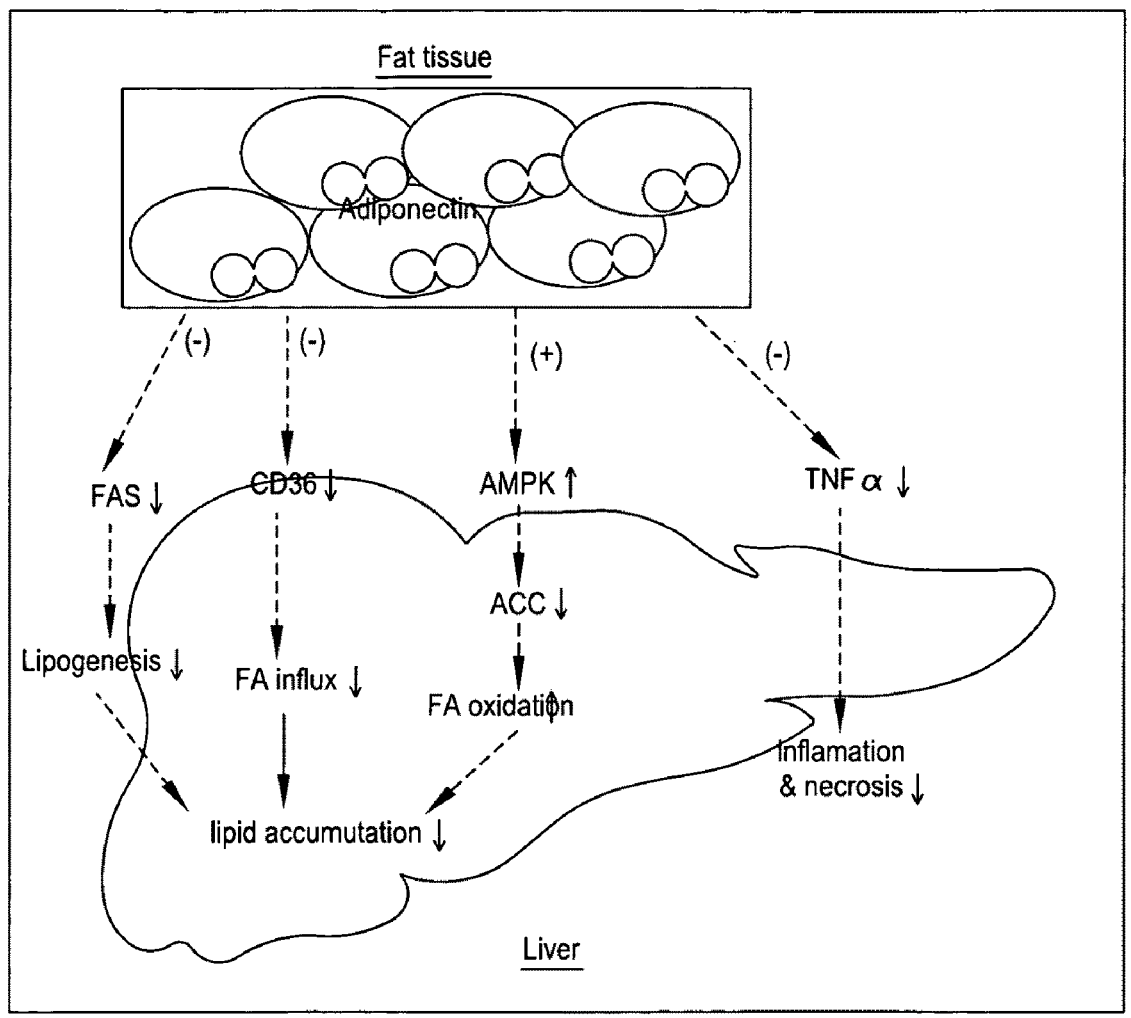
FIG. 15 Schematic representation of the potential mechanisms that underlie the hepatoprotective action of adiponectin. FA: free fatty acid; ACC: acetyl CoA carboxylase; AMPK: 5'-AMP activated kinase; FAS: fatty acid synthase; TNF-α: tumor necrosis factor alpha.
Figure 16:
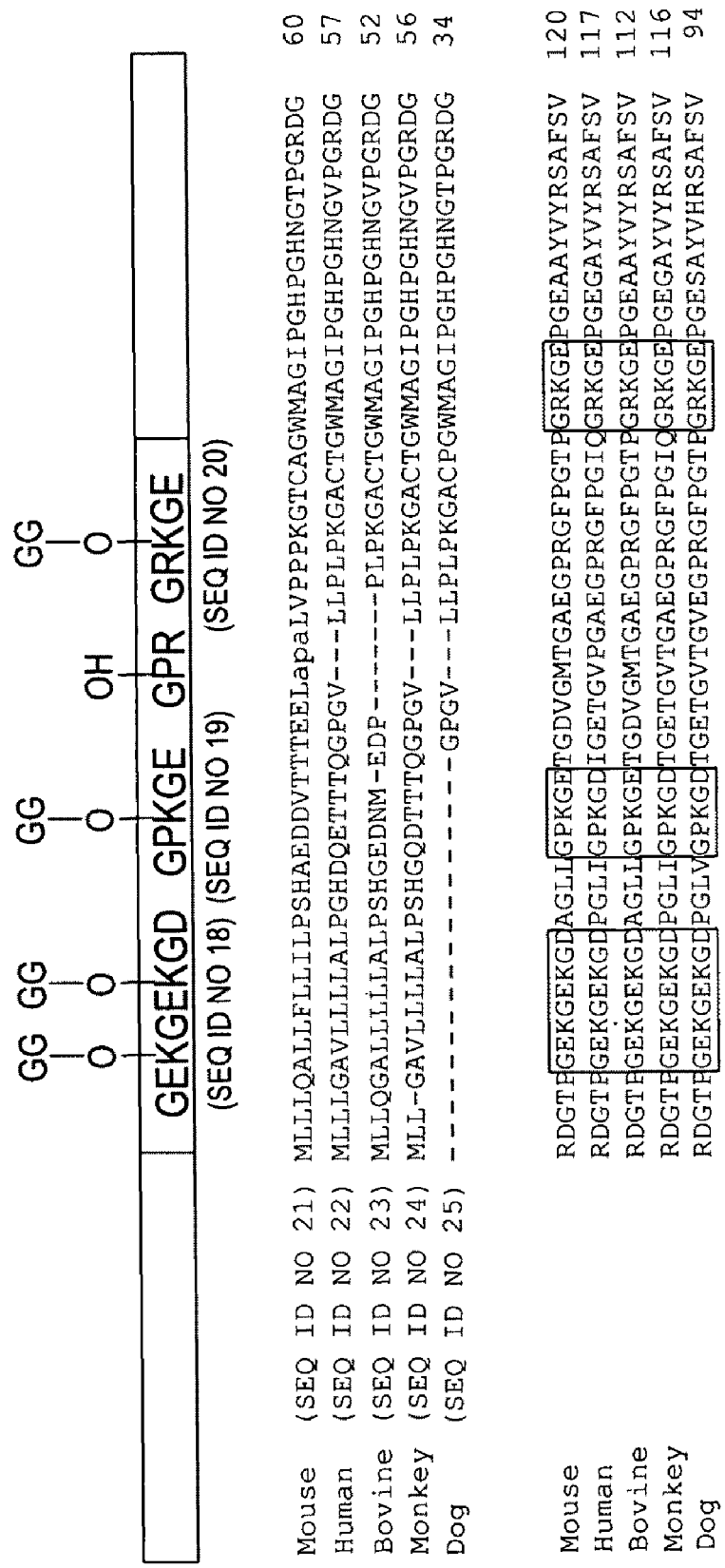
FIG. 16 Glycosylation and hydroxylation of adiponectin occurs on several conserved lysine residues (Lys 68, 71, 80 and 104 of mouse adiponectin or corresponding residues in other species or adiponectin variants) within the collagenous domain of adiponectin with the surrounding motifs of GXKGE(D).

It is important to note that other metabolic effects of adiponectin may also contribute to the suppression of alcohol-induced hepatic fat accumulation. For instance, administration of a truncated COOH-terminal globular-region fragment of adiponectin in vivo has been shown to enhance the clearance of circulating free fatty acid and triglyceride 4, which in turn will decrease the source of fatty-acid influx into the liver. Although the increased ratio of NADH/NAD+ following alcoholic injury is not affected, it is still possible that adiponectin can directly increase hepatic mitochondrial β-oxidation by other mechanisms. Indeed, a more recent study has shown that full-length adiponectin can activate 5'-AMP-activated kinase in rat hepatocytes, which in turn will phosphorylate acetyl-CoA carboxylase (ACC) and attenuate the activity of this enzyme 30. Inactivation of ACC in the liver cells will lead to decreases in the concentration of its product, malonyl-CoA, and will thus induce fatty acid β-oxidation in this tissue 31 Adiponectin may thus abrogates alcohol-induced fatty liver by regulating multiple coordinated metabolic pathways (FIG. 15).

The marked effect of adiponectin on depletion of excessive hepatic fat accumulation is consistent with adiponectin deficiency being closely correlated with hepatic lipid accumulation in patients with insulin resistance[44]. Notably, in liver from carbon tetrachloride-treated mice, large amounts of adiponectin were found to accumulate and to bind to the extracellular matrix adjacent to hepatocytes[45]. The hormone may also act as an anti-inflammatory factor that participates in the repair process in CCl4-induced liver injury.

In addition to its anti-diabetic and anti-atherogenic potential 1, adiponectin or its agonists represent novel agents for the treatment of liver diseases.

Example 7

Discussion

Several recent reports independently report on the anti-diabetic role of adiponectin. However, it is still controversial which form of adiponectin is functionally active. Studies from Lodish's and Kadowaki's groups found that a truncated fragment corresponding to the globular domain of adiponectin is effective in decreasing hyperglycemia and restoring insulin resistance. Bacterially produced full length adiponectin showed no activity [10, 11]. The physiological relevance of these finding is uncertain. The preponderance of plasma adiponectin exists as full-length protein with apparent MW of 30 kDa [5, 6]. We were unable to detect any proteolytic fragment of adiponectin in human and mouse serum, using both immunoprecipitation and Western blot analysis of the proteins separated by 2-DE (data not shown). Furthermore, amino terminal sequence analysis revealed that all the major isoforms of adiponectin secreted by adipocytes share identical N terminus (FIG. 1), indicating that this protein is not cleaved intracellularly during its secretion. Although Lodish and colleagues reported a faint band with 25 kDa, this experiment use the same antibody for both immunoprecipitation and Western blot analysis, which could also visualize the antibody light chain with MW of ~25 kDa.

In contrast with these reports, Scherer and colleagues reported that full-length adiponectin produced from mammalian cells could acutely decrease hyperglycemia in several diabetic animal models, while either full-length adiponectin or its globular region derived from *E. coli* has no such activities [9].

Our 2-DE analysis revealed that adiponectin secreted from adipocytes is extensively modified into multiple isoforms with different pI and MW, and this heterogeneity can be explained at least partly by glycosylation (FIG. 1 and FIG. 2). Comparison of the mass spectra between the unglycosylated and glycosylated isoforms allowed us to identify the four lysines (68, 71, 80 and 104) within the collagenous domain as potential glycosylation sites (FIG. 3). The conclusion that these four lysines are glycosylated was further supported by the following evidences. First, these four lysines were not able to be sequenced, and were also resistant to trypsin cleavage, indicating that they might be modified. Second, amino acid analysis revealed that all these four lysines were hydroxylated (FIG. 6). Third, the glycosylation of adiponectin was substantially decreased following substitution of these four lysines with arginines (FIG. 9), or following treatment with α,α'-dipyridyl, a hydoxylase inhibitor (unpublished observation). Notably, hydroxylysyl glycosylation on these four sites was detected on all the six major glycosylated isoforms, which account for over 85% of the total adiponectin secreted from adipocytes, suggesting this glycosylation is one of the major posttranslational modifications occurring on adiponectin. Interestingly, all these four lysine residues are located within a consensus sequence GXKGE(D), which is very conserved across all the species of adiponectin identified so far (FIG. 5).

Hydroxylation of lysine and subsequent glycosylation with galactose and glucose to form glucosylgalactosylhydroxylysine (GlcGalHyl-Lys) has been previously observed in many secretory proteins with collagen-like domain, including complement component C1q and pulmonary surfactant proteins [30]. The functional relevance of this modification is currently unknown. We have obtained evidence suggesting that the glycosides attached on the four lysines can be glucosylgalactosyl groups. Mass spectrometric analysis indicated that the mass of the glycoside group on lysine 80 and 104 was 340 Da, an expected size for a GlcGalHyl residue (FIG. 7). Radiolabelling experiments also revealed the glycosides contained both 3H-galactose and 3H-glucose (FIG. 8).

The physiological importance of glycosylation on the four hydroxylated lysines was implicated by a functional analysis using the adiponectin variant (K→R), which showed that substitution of these lysines with arginines significantly attenuated the ability of sub-physiological concentration of adiponectin to enhance the hepatic action of insulin to suppress glucose production (FIG. 10). This result also emphasized that the collagenous domain was also involved in the insulin-sensitizing function of adiponectin. The mechanisms by which glycosides attached with these four lysine residues at the collagenous domain enhance the insulin-sensitizing effect of adiponectin remains to be defined. The insulin-sensitizing ability of the adiponectin variants in which only one of the four lysine residues was replaced by arginine, was much lower than that of the wild type adiponectin, but significantly higher than that of the variant with the mutations at all four sites (data not shown), suggesting that the glycosides attached with each lysine might function in a cooperative manner. These glycosides may be directly involved in ligand-receptor interaction. Alternatively, it might be important for the proper folding and stabilization of its three dimensional structure required for the biological functions. These possibilities are currently under investigation in our laboratory.

We have also been able to demonstrate that circulating concentrations of mouse adiponectin in mice decreased significantly following chronic consumption of high fat ethanol containing food. Delivery of recombinant mouse adiponectin into these mice dramatically alleviated, hepatomegaly and steatosis (fatty liver), and also significantly attenuated inflammation and the elevated levels of serum alanine aminotransferase. Mouse adiponectin treatment was found to decrease the hepatic production of TNF-α, and the expression of fatty acid synthase and the fatty acid transport protein CD36.

DOCUMENT LIST

1. Molina, P. E. et al. *Molecular pathology and clinical aspects of alcohol-induced tissue injury*. Alcoholism: Clin. Exp. Res. 26, 120-128 (2002).
2. Stewart, S., Jones, D. & Day, C.P. Alcoholic liver disease: new insights into mechanisms and preventative strategies. Trends Mol. Med. 7, 408-413 (2001).
3. Tsukamoto, H. & Lu, S. C. Current concepts in the pathogenesis of alcoholic liver injury. FASEB J. 15, 1335-1349 (2001).
4. Diehl, A. M. Cytokine regulation of liver injury and repair. Immunol. Rev. 174, 160-171 (2000).
5. Tilg, H. & Diehl, A. M. Cytokines in alcoholic and nonalcoholic steatohepatitis. New Eng. J. Med. 343, 1467-1476 (2000).
6. Thurman, R. G. et al. Mechanisms of alcohol-induced hepatotoxicity: studies in rats. Front. Biosci. 4, e42-46 (1999).
7. McClain, C. J., Barve, S., Deaciue, J., Kugelmas, M. & Hill, D. Cytokines in alcoholic liver disease. Semin. Liver Disease 19, 205-219 (1999).
8. Adachi, Y., Bradford, B. U., Gao, W., Bojes, H. K. & Thurman, R. G. Inactivation of Kupffer cells prevents early alcohol-induced liver injury. Hepatology 20, 453-460 (1994).
9. Jarvelainen, H. A. et al, Kupffer cell inactivatin alleviates ethanol-induced steatosis and CYP2E1 induction but not inflammatory responses in rat liver. J. Hepatol. 32, 900-910 (2000).
10. Iimuro, Y., Gallucci, R. M., Luster, M. I., Kono, H. & Thurman, R. G. Antibodies to tumor necrosis factor alfa attenuate hepatic necrosis and inflammation caused by chronic exposure to ethanol in the rat. Hepatology 26, 1530-1537 (1997).
11. Yin, M. et al. Essential role of tumor necrosis factor alpha in alcohol-induced liver injury in mice. Gastroenterology 177, 942-952 (1999).
12. Enomoto, N. et al. Thalidomide prevents alcoholic liver injury in rats through suppression of Kupffer cell sensitization and TNF-alpha production. Gastroenterology 123, 291-300 (2002).
13. Berg, A. H., Combs, T. P & Scherer, P. E. ACRP30/adiponectin: an adipokine regulating glucose and lipid metabolism. Trends Endocrinol. Metab. 13, 84-89 (2002).
14. Shaprio, L. & Scherer, P. E. The crystal structure of a complement-1q family protein suggests an evolutionary link to tumor necrosis factor. Curr. Biol. 8, 335-338 (1998).
15. Maeda, N. et al. Diet-induced insulin resistance in mice lacking adiponectin/ACRP30. Nat. Med. 8, 731-737 (2002).
16. Yamauchi, T. et al. The fat-derived hormone adiponectin reverses insulin resistance associated with both lipoatrophy and obesity. Nat. Med 7, 941-946 (2001).
17. Fruebis, J. et al. Proteolytic cleavage product of 30-kDa adipocyte complement-related protein increases fatty acid oxidation in muscle and causes weight loss in mice. Proc. Nat. Acad. Sci. U.S.A. 98, 2005-2010 (2001).
18. Berg, A. H., Combs, T. P., Du, X., Brownlee, M. & Scherer, P. E. The adipocyte-secreted protein Acrp30 enhances hepatic insulin action. Nat. Med 7, 947-953 (2001).
19. Wang, Y., Xu, A., Knight, C., Xu, L. Y. & Cooper, G. J. Hydroxylation and glycosylation of the four conserved lysine residues in the collagenous domain of adiponectin. Potential role in the modulation of its insulin-sensitizing activity. J. Biol. Chem. 277, 19521-19529 (2002).
20. Yokota, T. et al. Adiponectin, a new member of the family of soluble defense collagens, negatively regulates the growth of myelomonocytic progenitors and the functions of macrophages. Blood 96, 1723-1732 (2000).
21. Hotta, K., et al., *Circulating concentrations of the adipocyte protein adiponectin are decreased in parallel with reduced insulin sensitivity during the progression to type 2 diabetes in rhesus monkeys*. Diabetes, 2001. 50(5): p. 1126-1133.
23. Lindros, K. O. & Jarvelainen, H. A. A new oral low-carbohydrate alcohol liquid diet producing liver lesions: a preliminary account. Alcohol Alcoholism 33, 347-353 (1998).
24. Fasshauer, M., Klein, J., Neumann, S., Esslinger, M. & Paschke, R. Hormonal regulation of adiponectin gene expression in 3T3-L1 adipocytes. Biochem. Biophys. Res. Commun. 290, 1084-1089 (2002).
25. Steppan, C. M. & Lazar, M. A. Resistin and obesity-associated insulin resistance. Trends Endocrinol. Metab. 13, 18-23 (2002).
26. Ouchi, N. et al. A novel adipocyte-derived plasma protein, adiponectin, suppresses scavenger receptor expression in human monocyte-derived macrophages. Circulation 100, 3967 (1999).
27. Ouchi, N. et al. Novel modulator for endothelial adhesion molecules: adipocyte-derived plasma protein adiponectin. Circulation 100, 2473-2476 (1999).
28. Ross, R. Atherosclerosis: an inflammatory disease. New Eng. J. Med. 340, 115-126 (1999).
29. Eaton, S., Record, C. O. & Bartlett, K. Multiple biochemical effects in the pathogenesis of alcoholic fatty liver. Eur. J. Clin. Invest. 27, 719-722 (1997).
30. You, M., Fischer, M., Deeg, M. A. & Crabb, D. W. Ethanol induces fatty acid synthesis pathways by activation of sterol regulatory element-binding protein (SREBP). J. Biol. Chem. 277, 29342-29347 (2002).

31. Siler, S. Q., Neese, R. A. & Hellerstein, M. K. De novo lipogenesis, lipid kinetics, and whole-body lipid balances in humans after acute alcohol consumption. Am. J. Clin. Nutr. 70, 928-936 (1999).

32. Funabiki, A., Maeda, K., Ishihara, K., Okada, Y. & Kasuga, M. Adiponectin is associated with insulin resistance in liver. Diabetes 51 (suppl 2), A32 (2002).

33. Yoda-Murakami, M. et al, Change in expression of GBP28/adiponectin in carbon tetrachloride-administrated mouse liver. Biochem. Biophys. Res. Commun. 285, 372-377 (2001).

OTHER DOCUMENTS ARE

Bradley, R. L., K. A. Cleveland, and B. Cheatham, *The adipocyte as a secretory organ: mechanisms of vesicle transport and secretory pathways*. Recent Progress in Hormone Research, 2001. 56: p. 329-58.

Fruhbeck, G., et al., *The adipocyte: a model for integration of endocrine and metabolic signaling in energy metabolism regulation*. American Journal of Physiology—Endocrinology & Metabolism, 2001. 280(6): p. E827-47.

Kim, S. and N. Moustaid-Moussa, *Secretory, endocrine and autocrine/paracrine function of the adipocyte*. Journal of Nutrition, 2000. 130(12): p. 3110S-3115S.

Steppan, C. M. and M. A. Lazar, *Resistin and obesity-associated insulin resistance*. TRENDS in endocrinology & metabolism, 2002. 13(1): p. 18-23.

Scherer, P. E., et al., *A Novel Serum-Protein Similar to C1q, Produced Exclusively in Adipocytes*. Journal of Biological Chemistry, 1995. 270(45): p. 26746-26749.

Nakano, Y., et al., *Isolation and characterization of GBP28, a novel gelatin-binding protein purified from human plasma*. Journal of Biochemistry, 1996. 120(4): p. 803-12.

Hu, E., P. Liang, and B. M. Spiegelman, *AdipoQ is a novel adipose-specific gene dysregulated in obesity*. Journal of Biological Chemistry, 1996. 271(18): p. 10697-10703.

Maeda, K., et al., *cDNA cloning and expression of a novel adipose specific collagen-like factor, apM1 (AdiPose Most abundant Gene transcript 1)*. Biochemical & Biophysical Research Communications, 1996. 221(2): p. 286-9.

Berg, A. H., et al., *The adipocyte-secreted protein Acrp30 enhances hepatic insulin action*. Nature Medicine, 2001. 7(8): p. 947-53.

Fruebis, J., et al., *Proteolytic cleavage product of 30-kDa adipocyte complement-related protein increases fatty acid oxidation in muscle and causes weight loss in mice*. Proceedings of the National Academy of Sciences of the United States of America, 2001. 9.8(4): p. 2005-10.

Yamauchi, T., et al., *The fat-derived hormone adiponectin reverses insulin resistance associated with both lipoatrophy and obesity*. Nature Medicine, 2001. 7(8): p. 941-6.

Saito, K., et al., *Organization of the gene for gelatin-binding protein (GBP28)*. Gene, 1999. 229(1-2): p. 67-73.

Das, K., et al., *Chromosomal localization, expression pattern, and promoter analysis of the mouse gene encoding adipocyte-specific secretory protein Acrp30*. Biochemical & Biophysical Research Communications, 2001. 280(4): p. 1120-9.

Takahashi, M., et al., *Genomic structure and mutations in adipose-specific gene, adiponectin*. International Journal of Obesity, 2000. 24(7): p. 861-868.

Arita, Y., et al., *Paradoxical decrease of an adipose-specific protein, adiponectin, in obesity*. Biochemical and Biophysical Research Communications, 1999. 257(1): p. 79-83.

Hotta, K., et al., *Plasma concentrations of a novel, adipose-specific protein, adiponectin, in type 2 diabetic patients*. Arteriosclerosis Thrombosis and Vascular Biology, 2000. 20(6): p. 1595-1599.

Weyer, C., et al., *Hypoadiponectinemia in obesity and type 2 diabetes: Close association with insulin resistance and hyperinsulinemia*. Journal of Clinical Endocrinology and Metabolism, 2001. 86(5): p. 1930-1935.

Statnick, M. A., et al., *Decreased expression of apM1 in omental and subcutaneous adipose tissue of humans with type 2 diabetes*. International Journal of Experimental Diabetes Research, 2000. 1(2): p. 81-8.

Hotta, K., et al., *Circulating concentrations of the adipocyte protein adiponectin are decreased in parallel with reduced insulin sensitivity during the progression to type 2 diabetes in rhesus monkeys*. Diabetes, 2001. 50(5): p. 1126-1133.

Yang, W. S., et al., *Weight reduction increases plasma levels of an adipose-derived anti-inflammatory protein, adiponectin*. Journal of Clinical Endocrinology and Metabolism, 2001. 86(8): p. 3815-3819.

Combatsiaris, T. P., et al., *Induction of Acrp30 levels by PPAR gamma agonists: A potential mechanism of insulin sensitization*. Diabetes, 2001. 50: p. A271-A272.

Maeda, N., et al., *PPAR gamma ligands increase expression and plasma concentrations of adiponectin, an adipose-derived protein*. Diabetes, 2001. 50(9): p. 2094-2099.

Shapiro, L. and P. E. Scherer, *The crystal structure of a complement-1q family protein suggests an evolutionary link to tumor necrosis factor*. Current Biology, 1998. 8(6): p.335-338.

Wang, Y., et al., *Alteration in phosphorylation of P20 is associated with insulin resistance*. Diabetes, 2001. 50(8): p. 1821-7.

Wang, Y., et al., *Insulin and insulin antagonists evoke phosphorylation of P20 at serine 157 and serine 16 respectively in rat skeletal muscle*. FEBS Letters, 1999. 462(1-2): p. 25-30.

Johnson, R. G., et al., *Biochemical analysis of rabbit articular cartilage using an amino acid analyzer*. Clinical Orthopaedics & Related Research, 1980(146): p. 282-8.

Leffert, H. L., et al., *Liver cells*. Methods Enzymol, 1979. 58: p. 536-544.

Wu, G. C., et al., *N-glycosylation and residues Asn805 and Asn890 are involved in the functional properties of type VI adenylyl cyclase*. Journal of Biological Chemistry, 2001. 276(38): p. 35450-7.

Hansen, J. E., et al., *NetOglyc: prediction of mucin type O-glycosylation sites based on sequence context and surface accessibility*. Glycoconjugate Journal, 1998. 15(2): p. 115-30.

Colley, K. J. and J. U. Baenziger, *Identification of the post-translational modifications of the core-specific lectin. The core-specific lectin contains hydroxyproline, hydroxylysine, and glucosylgalactosylhydroxylysine residues*. Journal of Biological Chemistry, 1987. 262 (21): p. 10290-5.

Shinkai, H. and K. Yonemasu, *Hydroxylysine-linked glycosides of human complement subcomponent C1q and various collagens*. Biochemical Journal, 1979. 177(3): p. 847-52.

Lindros, K. O. & Jarvelainen, H. A. *A new oral low-carbohydrate alcohol liquid diet producing liver lesions: a preliminary account*. Alcohol Alcoholism 33, 347-353 (1998).

Fasshauer, M., Klein, J., Neumann, S., Esslinger, M. & Paschke, R. *Hormonal regulation of adiponectin gene expression in 3T3-L1 adipocytes*. Biochem. Biophys. Res. Commum 290, 1084-1089 (2002).

Wang, Y., Xu, A., Knight, C., Xu, L. Y. & Cooper, G. J. *Hydroxylation and glycosylation of the four conserved lysine residues in the collagenous domain of adiponectin. Potential role in the modulation of its insulin-sensitizing activity*. J. Biol. Chem. 277, 19521-19529 (2002).

Tilg, H. & Diehl, A. M. *Cytokines in alcoholic and nonalcoholic steatohepatitis*. New Eng. J. Med 343, 1467-1476 (2000).

Steppan, C. M. & Lazar, M. A. *Resistin and obesity-associated insulin resistance*. Trends Endocrinol. Metab. 13, 18-23 (2002).

Ouchi, N. et al. *A novel adipocyte-derived plasma protein, adiponectin, suppresses scavenger receptor expression in human monocyte-derived macrophages*. Circulation 100, 3967 (1999).

Ouchi, N. et al. *Novel modulator for endothelial adhesion molecules: adipocyte-derived plasma protein adiponectin*. Circulation 100, 2473-2476 (1999).

Ross, R. *Atherosclerosis: an inflammatory disease*. New Eng. J. Med 340, 115-126 (1999).

Maeda, N. et al. *Diet-induced insulin resistance in mice lacking adiponectin/ACRP30*. Nat. Med. 8, 731-737 (2002).

Eaton, S., Record, C. O. & Brlett, K. *Multiple biochemical effects in the pathogenesis of alcoholic fatty liver*. Eur. J. Clin. Invest 27, 719-722 (1997).

You, M., Fischer, M., Deeg, M. A. & Crabb, D. W. *Ethanol induces fatty acid synthesis pathways by activation of sterol regulatory element-binding protein (SREBP)*. J. Biol. Chem. 277, 29342-29347 (2002).

Siler, S. Q., Neese, R. A. & Hellerstein, M. K. *De novo lipogenesis, lipid kinetics, and whole-body lipid balances in humans after acute alcohol consumption*. Am. J. Clin. Nutr. 70, 928-936 (1999).

Funabiki, A., Maeda, K., Ishihara, K., Okada, Y. & Kasuga, M. *Adiponectin is associated with insulin resistance in liver*. Diabetes 51 (suppl 2), A32 (2002).

Yoda-Murakami, M. et al, Change *in expression of GBP28/adiponectin in carbon tetrachloride-administrated mouse liver*. Biochem. Biophys. Res. Commun. 285, 372-377 (2001).

Yamauchi, T. et al. Adiponectin stimulates glucose utilization and fatty-acid oxidation by activating AMP-activated protein kinase. Nat. Med. 7, 1-8 (2002).

Winder, W. W. & Hardie, D. G. AMP-activated protein kinase, a metabolic master switch: possible roles in type 2 diabetes. Am. J. Physiol. 277, E1-10 (1999).

\*\*\*

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

---

What we claim is:

1. A composition which comprises a pharmaceutically acceptable carrier and substantially pure glycosylated human adiponectin in an amount effective for treating inflammation of the liver wherein the adiponectin comprises a glycosylated lysine residue at one or more positions of 65, 68, 77 and 101.

2. The composition of claim 1 wherein the adiponectin comprises glycosylated lysine residues at least two of positions 65, 68, 77, and 101.

3. The composition of claim 1 wherein at least one or more of the lysine residues at positions 65, 68, 77, and 101 comprise a glucosylgalactosyl moiety, a glucosylglucosyl moiety, a galactosylglucosyl moiety, or a galactosylgalactosyl moiety.

4. The composition of claim 1 wherein at least one or more of the lysine residues at positions 65, 68, 77, and 101 comprise a glucosylgalactosyl moiety, a glucosylglucosyl moiety, a galactosylglucosyl moiety, or a galactosylgalactosyl moiety.

5. The composition of claim 1 wherein at least one or more of the lysine residues at positions 65, 68, 77, and 101 comprise a glucosylgalactosyl moiety or a galactosylglucosyl moiety.

6. The composition of claim 1 wherein at least one or more of the lysine residues at positions 65, 68, 77, and 101 comprise a glucosylgalactosyl moiety or a galactosylglucosyl moiety.

7. A composition which comprises a pharmaceutically acceptable carrier and substantially pure glycosylated human adiponectin in an amount effective for treating inflammation of the liver wherein the human adiponectin comprises a sugar moiety attached to one or more lysine residues at positions 65, 68, 77 and 101.

8. The composition of claim 7 wherein the human adiponectin comprises a sugar moiety attached to two or more lysine residues at positions 65, 68, 77, and 101.

9. The composition of any of claim 1, 2, 7 or 8 wherein the adiponectin has the amino acid sequence of a naturally occurring human adiponectin.

10. The composition of any of claim 1, 2, 7 or 8 wherein the amino acid residue at position 91 of the glycosylated human adiponectin is hydroxyproline.

11. The composition of claim 1 wherein the glycosylated human adiponectin is recombinant.

12. The composition of claim 1 wherein the amount is effective to elicit a plasma adiponectin concentration from about 1 ug/mL to about 20 ug/mL.

13. The composition of claim 1 wherein the amount is effective to elicit a plasma adiponectin concentration from about 1.9 ug/mL to about 17 ug/mL, 14. The composition of claim 1 wherein the glycosylated human adiponectin is at least about 50% pure.

15. The composition of claim 1 wherein the glycosylated human adiponectin is at least about 80% pure.

16. The composition of claim 1 wherein the glycosylated human adiponectin is at least about 90% pure.

17. The composition of claim 1 wherein the glycosylated human adiponectin is at least about 95% pure.

18. The composition of claim 1 wherein the glycosylated human adiponectin is at least about 99% pure.

* * * * *

SEQUENCE LISTING

```
<160> NUMBER OF SEQ ID NOS: 25

<210> SEQ ID NO 1
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Putative consensus glycation motif
<220> FEATURE:
<221> NAME/KEY: MOD_RES
<222> LOCATION: (2)..(2)
<223> OTHER INFORMATION: Any amino acid

<400> SEQUENCE: 1

Gly Xaa Lys Gly Glu Asp
1               5

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atcgggatcc gaagatgacg ttactacaac t                                    31
```

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tacgaattct cagttggtat catggtagag                              30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atcgggatcc gccgcttata tgtatcgctc                              30

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gcccgcggat ccatgctact gttgcaagct ct                           32

<210> SEQ ID NO 6
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggccgcgaat tctcacttgt catcgtcgtc cttgtagtcg ttggtatcat ggtagag    57

<210> SEQ ID NO 7
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Corresponds to amino acids 18-25 of murine
      adiponectin

<400> SEQUENCE: 7

Glu Asp Asp Val Thr Thr Thr Glu
1               5

<210> SEQ ID NO 8
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: Corresponds to amino acids 104-115 of murine
      adiponectin

<400> SEQUENCE: 8
```

```
Lys Gly Glu Pro Gly Glu Ala Ala Tyr Val Tyr Arg
1               5                   10

<210> SEQ ID NO 9
<211> LENGTH: 34
<212> TYPE: PRT
<213> ORGANISM: Mus musculus
<220> FEATURE:
<221> NAME/KEY: MISC_FEATURE
<222> LOCATION: (1)..(34)
<223> OTHER INFORMATION: Corresponds to amino acids 62-95 of murine
      adiponectin

<400> SEQUENCE: 9

Asp Gly Thr Pro Gly Glu Lys Gly Glu Lys Gly Asp Ala Gly Leu Leu
1               5                   10                  15

Gly Pro Lys Gly Glu Thr Gly Asp Val Gly Met Thr Gly Ala Glu Gly
            20                  25                  30

Pro Arg

<210> SEQ ID NO 10
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Corresponds to amino acids 85-95 of murine
      adiponectin

<400> SEQUENCE: 10

Asp Val Gly Met Thr Gly Ala Glu Gly Pro Arg
1               5                   10

<210> SEQ ID NO 11
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: Corresponds to amino acids 62-72 of murine
      adiponectin

<400> SEQUENCE: 11

Asp Ala Gly Leu Leu Gly Pro Lys Gly Glu Thr Gly
1               5                   10

<210> SEQ ID NO 12
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Corresponds to amino acids 73-84 of murine
      adiponectin

<400> SEQUENCE: 12

Asp Gly Thr Pro Gly Glu Lys Gly Glu Lys Gly
1               5                   10

<210> SEQ ID NO 13
<211> LENGTH: 247
<212> TYPE: PRT
<213> ORGANISM: Mus musculus

<400> SEQUENCE: 13
```

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65              70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
            115                 120                 125

Pro Asn Val Pro Ile Arg Phe Thr Lys Ile Phe Tyr Asn Gln Gln Asn
130                 135                 140

His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245

<210> SEQ ID NO 14
<211> LENGTH: 244
<212> TYPE: PRT
<213> ORGANISM: Homo sapiens

<400> SEQUENCE: 14

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65              70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
            115                 120                 125

-continued

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 15
<211> LENGTH: 240
<212> TYPE: PRT
<213> ORGANISM: Bos taurus

<400> SEQUENCE: 15

Met Leu Leu Gln Gly Ala Leu Leu Leu Leu Ala Leu Pro Ser His
1               5                   10                  15

Gly Glu Asp Asn Met Glu Asp Pro Pro Leu Pro Lys Gly Ala Cys Ala
            20                  25                  30

Gly Trp Met Ala Gly Ile Pro Gly His Pro Gly His Asn Gly Thr Pro
        35                  40                  45

Gly Arg Asp Gly Arg Asp Gly Thr Pro Gly Glu Lys Gly Glu Lys Gly
    50                  55                  60

Asp Pro Gly Leu Val Gly Pro Lys Gly Asp Thr Gly Glu Thr Gly Ile
65                  70                  75                  80

Thr Gly Ile Glu Gly Pro Arg Gly Phe Pro Gly Thr Pro Gly Arg Lys
                85                  90                  95

Gly Glu Pro Gly Glu Ser Ala Tyr Val Tyr Arg Ser Ala Phe Ser Val
            100                 105                 110

Gly Leu Glu Arg Gln Val Thr Val Pro Asn Val Pro Ile Arg Phe Thr
        115                 120                 125

Lys Ile Phe Tyr Asn Gln Gln Asn His Tyr Asp Gly Thr Thr Gly Lys
    130                 135                 140

Phe Leu Cys Asn Ile Pro Gly Leu Tyr Tyr Phe Ser Tyr His Ile Thr
145                 150                 155                 160

Val Tyr Leu Lys Asp Val Lys Val Ser Leu Tyr Lys Asn Asp Lys Ala
                165                 170                 175

Leu Leu Phe Thr His Asp Gln Phe Gln Asp Lys Asn Val Asp Gln Ala
            180                 185                 190

Ser Gly Ser Val Leu Leu Tyr Leu Glu Lys Gly Asp Gln Val Trp Leu
        195                 200                 205

Gln Val Tyr Glu Gly Glu Asn His Asn Gly Val Tyr Ala Asp Asn Val
    210                 215                 220

Asn Asp Ser Thr Phe Thr Gly Phe Leu Leu Tyr His Asn Ile Val Glu
225                 230                 235                 240

<210> SEQ ID NO 16
<211> LENGTH: 243

<212> TYPE: PRT
<213> ORGANISM: Macaca mulatta

<400> SEQUENCE: 16

Met Leu Leu Gly Ala Val Leu Leu Leu Ala Leu Pro Ser His Gly
1               5                   10                  15

Gln Asp Thr Thr Thr Gln Gly Pro Gly Val Leu Leu Pro Leu Pro Lys
            20                  25                  30

Gly Ala Cys Thr Gly Trp Met Ala Gly Ile Pro Gly His Pro Gly His
            35                  40                  45

Asn Gly Val Pro Gly Arg Asp Gly Arg Asp Gly Thr Pro Gly Glu Lys
        50                  55                  60

Gly Glu Lys Gly Asp Pro Gly Leu Ile Gly Pro Lys Gly Asp Thr Gly
65                  70                  75                  80

Glu Thr Gly Val Thr Gly Ala Glu Gly Pro Arg Gly Phe Pro Gly Ile
                85                  90                  95

Gln Gly Arg Lys Gly Glu Pro Gly Glu Gly Ala Tyr Val Tyr Arg Ser
            100                 105                 110

Ala Phe Ser Val Gly Leu Glu Thr Tyr Val Thr Val Pro Asn Met Pro
        115                 120                 125

Ile Arg Phe Thr Lys Ile Phe Tyr Asn Gln Gln Asn His Tyr Asp Gly
    130                 135                 140

Ser Thr Gly Lys Phe His Cys Asn Ile Pro Gly Leu Tyr Tyr Phe Ala
145                 150                 155                 160

Tyr His Ile Thr Val Tyr Met Lys Asp Val Lys Val Ser Leu Phe Lys
                165                 170                 175

Lys Asp Lys Ala Met Leu Phe Thr Tyr Asp Gln Tyr Gln Glu Asn Asn
            180                 185                 190

Val Asp Gln Ala Ser Gly Ser Val Leu Leu His Leu Glu Val Gly Asp
        195                 200                 205

Gln Val Trp Leu Gln Val Tyr Gly Glu Gly Glu Arg Asn Gly Leu Tyr
    210                 215                 220

Ala Asp Asn Asp Asn Asp Ser Thr Phe Thr Gly Phe Leu Leu Tyr His
225                 230                 235                 240

Asp Thr Asn

<210> SEQ ID NO 17
<211> LENGTH: 194
<212> TYPE: PRT
<213> ORGANISM: Canis familiaris

<400> SEQUENCE: 17

Gly Pro Gly Val Leu Leu Pro Leu Pro Lys Gly Ala Cys Pro Gly Trp
1               5                   10                  15

Met Ala Gly Ile Pro Gly His Pro Gly His Asn Gly Thr Pro Gly Arg
            20                  25                  30

Asp Gly Arg Asp Gly Thr Pro Gly Glu Lys Gly Glu Lys Gly Asp Pro
            35                  40                  45

Gly Leu Val Gly Pro Lys Gly Asp Thr Gly Glu Thr Gly Val Thr Gly
        50                  55                  60

Val Glu Gly Pro Arg Gly Phe Pro Gly Thr Pro Gly Arg Lys Gly Glu
65                  70                  75                  80

Pro Gly Glu Ser Ala Tyr Val His Arg Ser Ala Phe Ser Val Gly Leu
                85                  90                  95

Glu Ser Arg Ile Thr Val Pro Asn Val Pro Ile Arg Phe Thr Lys Ile
            100                 105                 110

```
Phe Tyr Asn Leu Gln Asn His Tyr Asp Gly Thr Thr Gly Lys Phe His
            115                 120                 125

Cys Asn Ile Pro Gly Leu Tyr Tyr Phe Ser Tyr His Ile Thr Val Tyr
130                 135                 140

Leu Lys Asp Val Lys Val Ser Leu Tyr Lys Lys Asp Lys Ala Met Leu
145                 150                 155                 160

Phe Thr Tyr Asp Gln Tyr Gln Glu Lys Asn Val Asp Gln Ala Ser Gly
                165                 170                 175

Ser Val Leu Leu His Leu Glu Val Gly Asp Gln Val Trp Leu Gln Val
            180                 185                 190

Tyr Gly

<210> SEQ ID NO 18
<211> LENGTH: 8
<212> TYPE: PRT
<213> ORGANISM: Mus musculus

<400> SEQUENCE: 18

Gly Glu Lys Gly Glu Lys Gly Asp
1               5

<210> SEQ ID NO 19
<211> LENGTH: 5
<212> TYPE: PRT
<213> ORGANISM: Mus musculus

<400> SEQUENCE: 19

Gly Pro Lys Gly Glu
1               5

<210> SEQ ID NO 20
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Corresponds to amino acids 102-106 of murine
      adiponectin

<400> SEQUENCE: 20

Gly Arg Lys Gly Glu
1               5

<210> SEQ ID NO 21
<211> LENGTH: 120
<212> TYPE: PRT
<213> ORGANISM: Mus musculus

<400> SEQUENCE: 21

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
                20                  25                  30

Pro Pro Pro Lys Gly Thr Cys Ala Gly Trp Met Ala Gly Ile Pro Gly
            35                  40                  45

His Pro Gly His Asn Gly Thr Pro Gly Arg Asp Gly Arg Asp Gly Thr
        50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
```

```
                            85                  90                  95
Phe Pro Gly Thr Pro Gly Arg Lys Gly Glu Pro Gly Glu Ala Ala Tyr
                100                 105                 110

Met Tyr Arg Ser Ala Phe Ser Val
        115                 120

<210> SEQ ID NO 22
<211> LENGTH: 117
<212> TYPE: PRT
<213> ORGANISM: Homo sapiens

<400> SEQUENCE: 22

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
                100                 105                 110

Ser Ala Phe Ser Val
            115

<210> SEQ ID NO 23
<211> LENGTH: 112
<212> TYPE: PRT
<213> ORGANISM: Bos taurus

<400> SEQUENCE: 23

Met Leu Leu Gln Gly Ala Leu Leu Leu Ala Leu Pro Ser His
1               5                   10                  15

Gly Glu Asp Asn Met Glu Asp Pro Pro Leu Pro Lys Gly Ala Cys Ala
            20                  25                  30

Gly Trp Met Ala Gly Ile Pro Gly His Pro Gly His Asn Gly Thr Pro
        35                  40                  45

Gly Arg Asp Gly Arg Asp Gly Thr Pro Gly Glu Lys Gly Glu Lys Gly
    50                  55                  60

Asp Pro Gly Leu Val Gly Pro Lys Gly Asp Thr Gly Glu Thr Gly Ile
65                  70                  75                  80

Thr Gly Ile Glu Gly Pro Arg Gly Phe Pro Gly Thr Pro Gly Arg Lys
                85                  90                  95

Gly Glu Pro Gly Glu Ser Ala Tyr Val Tyr Arg Ser Ala Phe Ser Val
                100                 105                 110

<210> SEQ ID NO 24
<211> LENGTH: 116
<212> TYPE: PRT
<213> ORGANISM: Macaca mulatta

<400> SEQUENCE: 24

Met Leu Leu Gly Ala Val Leu Leu Leu Ala Leu Pro Ser His Gly
1               5                   10                  15
```

```
Gln Asp Thr Thr Thr Gln Gly Pro Gly Val Leu Leu Pro Leu Pro Lys
            20                  25                  30

Gly Ala Cys Thr Gly Trp Met Ala Gly Ile Pro Gly His Pro Gly His
        35                  40                  45

Asn Gly Val Pro Gly Arg Asp Gly Arg Asp Gly Thr Pro Gly Glu Lys
    50                  55                  60

Gly Glu Lys Gly Asp Pro Gly Leu Ile Gly Pro Lys Gly Asp Thr Gly
 65             70                  75                  80

Glu Thr Gly Val Thr Gly Ala Glu Gly Pro Arg Gly Phe Pro Gly Ile
                85                  90                  95

Gln Gly Arg Lys Gly Glu Pro Gly Glu Gly Ala Tyr Val Tyr Arg Ser
            100                 105                 110

Ala Phe Ser Val
        115

<210> SEQ ID NO 25
<211> LENGTH: 94
<212> TYPE: PRT
<213> ORGANISM: Canis familiaris

<400> SEQUENCE: 25

Gly Pro Gly Val Leu Leu Pro Leu Pro Lys Gly Ala Cys Pro Gly Trp
 1               5                  10                  15

Met Ala Gly Ile Pro Gly His Pro Gly His Asn Gly Thr Pro Gly Arg
            20                  25                  30

Asp Gly Arg Asp Gly Thr Pro Gly Glu Lys Gly Glu Lys Gly Asp Pro
            35                  40                  45

Gly Leu Val Gly Pro Lys Gly Asp Thr Gly Glu Thr Gly Val Thr Gly
     50                  55                  60

Val Glu Gly Pro Arg Gly Phe Pro Gly Thr Pro Gly Arg Lys Gly Glu
 65             70                  75                  80

Pro Gly Glu Ser Ala Tyr Val His Arg Ser Ala Phe Ser Val
                85                  90
```